(12) United States Patent
Chen et al.

(10) Patent No.: US 11,168,078 B2
(45) Date of Patent: Nov. 9, 2021

(54) SULFOXIMINE, SULFONIMIDAMIDE, SULFONDIIMINE AND DIIMIDOSULFONAMIDE COMPOUNDS AS INHIBITORS OF INDOLEAMINE 2,3-DIOXYGENASE

(71) Applicants: Shanghai Fochon Pharmaceutical Co., Ltd., Shanghai (CN); Fochon Pharmaceuticals, Ltd., Chongqing (CN)

(72) Inventors: Zhifang Chen, Chongqing (CN); Rui Tan, Chongqing (CN); Qihong Liu, Chongqing (CN); Lijun Yang, Chongqing (CN); Zhifu Li, Chongqing (CN); Haohan Tan, Chongqing (CN); Hongbin Liu, Chongqing (CN); Xingdong Zhao, Chongqing (CN); Min Lin, Chongqing (CN); Jing Sun, Chongqing (CN); Weibo Wang, Moraga, CA (US)

(73) Assignees: Shanghai Fochon Pharmaceutical Co., Ltd., Shanghai (CN); Fochon Pharmaceuticals, Ltd., Congqing (CN)

(*) Notice: Subject to any disclaimer, the term of this patent is extended or adjusted under 35 U.S.C. 154(b) by 164 days.

(21) Appl. No.: 16/464,435

(22) PCT Filed: Nov. 28, 2017

(86) PCT No.: PCT/CN2017/113254
§ 371 (c)(1),
(2) Date: May 28, 2019

(87) PCT Pub. No.: WO2018/095432
PCT Pub. Date: May 31, 2018

(65) Prior Publication Data
US 2021/0070742 A1      Mar. 11, 2021

Related U.S. Application Data

(60) Provisional application No. 62/560,193, filed on Sep. 19, 2017, provisional application No. 62/426,599, filed on Nov. 28, 2016.

(51) Int. Cl.
| | | |
|---|---|---|
| A61K 31/4245 | (2006.01) |
| C07D 411/12 | (2006.01) |
| C07D 271/08 | (2006.01) |
| C07D 409/12 | (2006.01) |

(52) U.S. Cl.
CPC ......... C07D 411/12 (2013.01); C07D 271/08 (2013.01); C07D 409/12 (2013.01)

(58) Field of Classification Search
None
See application file for complete search history.

(56) References Cited

U.S. PATENT DOCUMENTS

| | | | |
|---|---|---|---|
| 2016/0220543 A1 | 8/2016 | Combs et al. | |
| 2019/0152932 A1* | 5/2019 | Wang | ................. A61K 31/4245 |

FOREIGN PATENT DOCUMENTS

| | | |
|---|---|---|
| CN | 105481789 A | 4/2016 |
| CN | 107304191 A | 10/2017 |

OTHER PUBLICATIONS

International Search Report issued in International Patent Application No. PCT/CN2017/11254 dated Feb. 24, 2018.

* cited by examiner

*Primary Examiner* — Samantha L Shterengarts
(74) *Attorney, Agent, or Firm* — Ice Miller LLP

(57) ABSTRACT

Provided are certain IDO inhibitors or pharmaceutically acceptable salts thereof which can inhibit enzymatic activity of indoleamine 2,3-dioxygenase (IDO) and may be useful for the treatment of diseases and disorders mediated by IDO. In addition, pharmaceutical compositions thereof and methods of use thereof are also provided.

17 Claims, No Drawings

SULFOXIMINE, SULFONIMIDAMIDE, SULFONDIIMINE AND DIIMIDOSULFONAMIDE COMPOUNDS AS INHIBITORS OF INDOLEAMINE 2,3-DIOXYGENASE

CROSS-REFERENCE TO RELATED APPLICATION

This application is a Section 371 of International Application No. PCT/CN2017/113254, filed Nov. 28, 2017, which was published in the English language on May 31, 2018, under International Publication No. WO 2018/095432 A1, which claims priority under 35 U.S.C. § 119(b) to U.S. Provisional Application No. 62/426,599, filed Nov. 28, 2016 and U.S. Provisional Application No. 62/560,193, filed Sep. 19, 2017, the disclosures of which are incorporated herein by reference in their entirety.

FIELD OF THE INVENTION

Provided are certain compounds or pharmaceutically acceptable salts thereof which can inhibit enzymatic activity of indoleamine 2,3-dioxygenase (IDO) and may be useful for the treatment of diseases and disorders mediated by IDO, such as hyper-proliferative disease like cancer, immunological disease and viral infections.

BACKGROUND OF THE INVENTION

Tryptophan is an amino acid required by all forms of life for protein synthesis and other important metabolic functions and it's essential for cell proliferation and survival, but animal are incapable of synthesizing it from simpler molecules. Indoleamine-2,3-dioxygenase (IDO) is an intracellular immunoregulatory enzyme that catalyzes the first and rate-determining step of tryptophan breakdown along the kynurenine pathway. By depleting tryptophan from local microenvironments, IDO seems to block the proliferation of T lymphocytes. T lymphocytes are extremely sensitive to tryptophan shortage, which causes their arrest in G1 phase of the cell cycle (J. Exp. Med. 1999, 189, 1363).

Overexpression of IDO can lead to increased tolerance in the tumor microenvironment and IDO is found to be overexpressed in a wide variety of human tumor types, where it has been implicated in immune escape (Nature Medicine, 2005, 11, 312). As IDO has a role in the escape of malignant cells from immunological attack, blocking its activity should increase the anti-tumor response and lead to tumor regression. Several in vivo studies showed that blocking IDO can limit tumor growth in rodents (Nature Med. 2003, 9, 1269; Nature Med. 2005, 11, 312; Int. J. Cancer 2002, 101, 151). Based on studies examining serum levels of tryptophan and kynurenine, IDO appears to be chronically activated in patients with cancer, and IDO activation correlates with more extensive disease (Br J Cancer. 2002, 86, 1691; Dermatology. 2007, 214, 8).

Moreover, IDO has also been found to be implicated in neurologic and psychiatric disorders including mood disorders as well as other chronic diseases characterized by IDO activation and tryptophan depletion, such as viral infection, for example AIDS, Alzheimer's disease, cancers, autoimmune disease, diseases of eye such as cataracts, bacterial infections such as Lyme disease, and streptococcal infections.

Therefore, a compound having an inhibitory activity on IDO will be very useful for the prevention or treatment of diseases and disorders mediated by IDO, such as hyper-proliferative diseases such as hyper-proliferative disease like cancer, immunological disease and viral infections. Although IDO inhibitors were disclosed in the arts, e.g., WO2006122150, many suffer from having short half-life or toxicity. Therefore, there is a need for new IDO inhibitors that have at least one advantageous property selected from potency, stability, selectivity, toxicity, pharmacodynamic and pharmacokinetic properties as an alternative for the treatment of hyper-proliferative diseases. In this regard, a novel class of IDO inhibitors is provided herein.

DISCLOSURE OF THE INVENTION

Disclosed herein are certain novel sulfoximine, sulfonimidamide, sulfondiimine and diimidosulfonamide compounds and pharmaceutical compositions thereof, and their use as pharmaceuticals.

In one aspect, disclosed herein is a compound of formula (I):

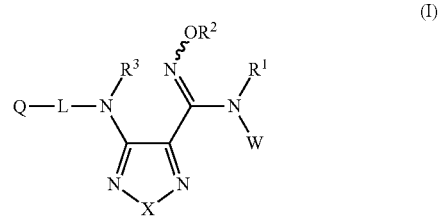

or a pharmaceutically acceptable salt thereof, wherein:
Q is selected from

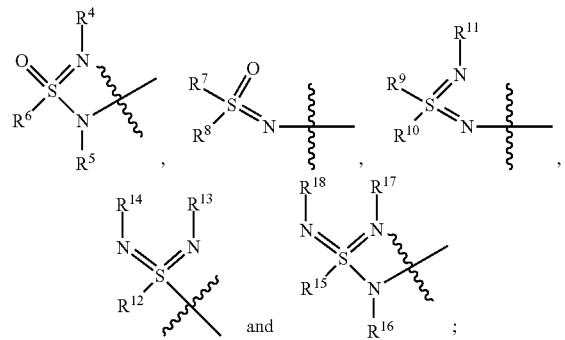

L is selected from —$(CR^{C1}R^{D1})_t$— and —$(CR^{C1}R^{D1})_tO(CR^{C1}R^{D1})_u$—;
X is selected from O and S;
W is selected from aryl and heteroaryl, wherein aryl and heteroaryl are each unsubstituted or substituted with at least one substituent, such as one, two, three or four substituents, independently selected from $R^X$;
$R^1$, $R^2$, $R^3$, $R^4$, $R^5$, $R^{11}$, $R^{13}$, $R^{14}$, $R^{16}$, $R^{17}$ and $R^{18}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, —CN, —$NO_2$, —$(CR^{C2}R^{D2})_tNR^{A2}R^{B2}$, —$(CR^{C2}R^{D2})_tOR^{A2}$, —$(CR^{C2}R^{D2})_tS(O)_rR^{A2}$, —$(CR^{C2}R^{D2})_tS(O)_2OR^{A2}$, —$(CR^{C2}R^{D2})_tOS(O)_2R^{A2}$, —$(CR^{C2}R^{D2})_tP(O)R^{A2}R^{B2}$, —$(CR^{C2}R^{D2})_tP(O)(OR^{A2})(OR^{B2})$, —$(CR^{C2}R^{D2})_tC(O)R^{A2}$, —$(CR^{C2}R^{D2})_tC(O)OR^{A2}$, —$(CR^{C2}R^{D2})_tOC(O)R^{A2}$, —(CR$^{C2}$R$^{D2}$)$_t$C(O)NR$^{A2}$R$^{B2}$, —(CR$^{C2}$R$^{D2}$)$_t$NR$^{A2}$C(O)R$^{B2}$, —(CR$^{C2}$R$^{D2}$)$_t$OC(O)NR$^{A2}$R$^{B2}$, —(CR$^{C2}$R$^{D2}$)$_t$NR$^{A2}$C(O)OR$^{B2}$, —(CR$^{C2}$R$^{D2}$)$_t$NR$^{A2}$C(O)NR$^{A2}$R$^{B2}$, —(CR$^{C2}$R$^{D2}$)$_t$NR$^{A2}$C(S)NR$^{A2}$R$^{B2}$, —(CR$^{C2}$R$^{D2}$)$_t$S(O)$_r$NR$^{A2}$R$^{B2}$, —(CR$^{C2}$R$^{D2}$)$_t$NR$^{A2}$S(O)$_r$R$^{B2}$, —(CR$^{C2}$R$^{D2}$)$_t$NR$^{A2}$S(O)$_2$NR$^{A2}$R$^{B2}$, —(CR$^{C2}$R$^{D2}$)$_t$S(O)(=NR$^{E2}$)R$^{B2}$, —(CR$^{C2}$R$^{D2}$)$_t$N=S(O)R$^{A2}$R$^{B2}$, —(CR$^{C2}$R$^{D2}$)$_t$NR$^{A2}$S(O)(=NR$^{E2}$)R$^{B2}$, —(CR$^{C2}$R$^{D2}$)$_t$S(O)(=NR$^{E2}$)NR$^{A2}$R$^{B2}$, —(CR$^{C2}$R$^{D2}$)$_t$NR$^{A2}$S(O)(=NR$^{E2}$)NR$^{A2}$R$^{B2}$, —(CR$^{C2}$R$^{D2}$)$_t$C(=NR$^{E2}$)R$^{A2}$, —(CR$^{C2}$R$^{D2}$)$_t$C(=N—OR$^{B2}$)R$^{A2}$, —(CR$^{C2}$R$^{D2}$)$_t$C(=NR$^{E2}$)NR$^{A2}$R$^{B2}$, —(CR$^{C2}$R$^{D2}$)$_t$NR$^{A2}$C(=NR$^{E2}$)R$^{B2}$, and —(CR$^{C2}$R$^{D2}$)$_t$NR$^{A2}$C(=NR$^{E2}$)NR$^{A2}$R$^{B2}$, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

R$^6$, R$^7$, R$^8$, R$^9$, R$^{10}$, R$^{12}$ and R$^{15}$ are independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^7$ and R$^8$ together with the sulfur atom to which they are attached form a 4-12 membered ring containing 0, 1 or 2 additional heteroatoms independently selected from oxygen, sulfur and nitrogen, and optionally substituted with 1, 2 or 3 R$^X$ groups;

or R$^9$ and R$^{10}$ together with the sulfur atom to which they are attached form a 4-12 membered ring containing 0, 1 or 2 additional heteroatoms independently selected from oxygen, sulfur and nitrogen, and optionally substituted with 1, 2 or 3 R$^X$ groups; each R$^{A2}$ and R$^{B2}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or R$^{A2}$ and R$^{B2}$ together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 R$^X$ groups;

each R$^{C1}$, R$^{C2}$, R$^{D1}$ and R$^{D2}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^X$;

or "R$^{C1}$ and R$^{D1}$" or "R$^{C2}$ and R$^{D2}$" together with the carbon atom(s) to which they are attached form a ring of 3 to 12 members containing 0, 1, or 2 heteroatoms independently selected from oxygen, sulfur and nitrogen, and optionally substituted with 1 2, or 3 R$^X$ groups;

each R$^{E2}$ are independently selected from hydrogen, C$_{1-10}$ alkyl, CN, NO$_2$, OR$^{a1}$, SR$^{a1}$, —S(O)$_r$R$^{a1}$, —S(O)$_r$NR$^{a1}$R$^{b1}$, —C(O)R$^{a1}$, —C(O)OR$^{a1}$ and —C(O)NR$^{a1}$R$^{b1}$;

each R$^X$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$ and —(CR$^{c1}$R$^{d1}$)$_t$NR$^{a1}$C(=NR$^{e1}$)NR$^{a1}$R$^{b1}$, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from R$^Y$;

or R$^{a1}$ and R$^{b1}$ together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from R$^Y$;

or R$^{c1}$ and R$^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 R$^Y$ groups;

each R$^{e1}$ is independently selected from hydrogen, C$_{1-10}$ alkyl, C$_{3-10}$ cycloalkyl, C$_{3-10}$ cycloalkyl-C$_{1-4}$ alkyl, CN, NO$_2$, OR$^{a2}$, SR$^{a2}$, —S(O)$_r$R$^{a2}$, —S(O)$_r$NR$^{a2}$R$^{b2}$, —C(O)R$^{a2}$, —C(O)OR$^{a2}$ and —C(O)NR$^{a2}$R$^{b2}$;

each R$^Y$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), —(CR$^{c2}$R$^{d2}$)$_t$C(O)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$C(O)NR$^{a2}$R$^{b2}$, —(CR$^{c2}$R$^{d2}$)$_t$ NR$^{a2}$C(S)NR$^{a2}$R$^{b2}$, —(CR$^{c2}$R$^{d2}$)$_t$S(O)$_r$NR$^{a2}$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$C(=NR$^{e2}$)R$^{a2}$, —(CR$^{c2}$R$^{d2}$)$_t$C(=N—OR$^{b2}$)R$^{a2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$ and —(CR$^{c2}$R$^{d2}$)$_t$NR$^{a2}$C(=NR$^{e2}$)NR$^{a2}$R$^{b2}$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, C$_{1-10}$ alkyl, C$_{2-10}$ alkenyl, C$_{2-10}$ alkynyl, C$_{3-10}$ cycloalkyl, C$_{1-10}$ alkoxy, C$_{3-10}$ cycloalkoxy, C$_{1-10}$ alkylthio, C$_{3-10}$ cycloalkylthio, C$_{1-10}$ alkylamino, C$_{3-10}$ cycloalkylamino and di(C$_{1-10}$ alkyl)amino;

each R$^{a2}$ and each R$^{b2}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, C$_{1-10}$ alkoxy, C$_{3-10}$ cycloalkoxy, C$_{1-10}$ alkylthio, C$_{3-10}$ cycloalkylthio, C$_{1-10}$ alkylamino, C$_{3-10}$ cycloalkylamino, di(C$_{1-10}$ alkyl)amino, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, C$_{1-10}$ alkyl, C$_{2-10}$ alkenyl, C$_{2-10}$ alkynyl, C$_{3-10}$ cycloalkyl, OH, C$_{1-10}$ alkoxy, C$_{3-10}$ cycloalkoxy, C$_{1-10}$ alkylthio, C$_{3-10}$ cycloalkylthio, amino, C$_{1-10}$ alkylamino, C$_{3-10}$ cycloalkylamino and di(C$_{1-10}$ alkyl)amino;

or R$^{a2}$ and R$^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from halogen, CN, C$_{1-10}$ alkyl, C$_{2-10}$ alkenyl, C$_{2-10}$ alkynyl, C$_{3-10}$ cycloalkyl, OH, C$_{1-10}$ alkoxy, C$_{3-10}$ cycloalkoxy, C$_{1-10}$ alkylthio, C$_{3-10}$ cycloalkylthio, amino, C$_{1-10}$ alkylamino, C$_{3-10}$ cycloalkylamino and di(C$_{1-10}$ alkyl)amino;

each R$^{c2}$ and each R$^{d2}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, C$_{1-10}$ alkoxy, C$_{3-10}$ cycloalkoxy, C$_{1-10}$ alkylthio, C$_{3-10}$ cycloalkylthio, C$_{1-10}$ alkylamino, C$_{3-10}$ cycloalkylamino, di(C$_{1-10}$ alkyl)amino, heterocyclyl, heterocyclyl-C$_{1-4}$ alkyl, aryl, aryl-C$_{1-4}$ alkyl, heteroaryl, and heteroaryl-C$_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, C$_{1-10}$ alkyl, C$_{2-10}$ alkenyl, C$_{2-10}$ alkynyl, C$_{3-10}$ cycloalkyl, OH, C$_{1-10}$ alkoxy, C$_{3-10}$ cycloalkoxy, C$_{1-10}$ alkylthio, C$_{3-10}$ cycloalkylthio, amino, C$_{1-10}$ alkylamino, C$_{3-10}$ cycloalkylamino and di(C$_{1-10}$ alkyl)amino;

or R$^{c2}$ and R$^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, C$_{1-10}$ alkyl, C$_{2-10}$ alkenyl, C$_{2-10}$ alkynyl, C$_{3-10}$ cycloalkyl, OH, C$_{1-10}$ alkoxy, C$_{3-10}$ cycloalkoxy, C$_{1-10}$ alkylthio, C$_{3-10}$ cycloalkylthio, amino, C$_{1-10}$ alkylamino, C$_{3-10}$ cycloalkylamino and di(C$_{1-10}$ alkyl)amino;

each R$^{e2}$ is independently selected from hydrogen, CN, NO$_2$, C$_{1-10}$ alkyl, C$_{3-10}$ cycloalkyl, C$_{3-10}$ cycloalkyl-C$_{1-4}$ alkyl, C$_{1-10}$ alkoxy, C$_{3-10}$ cycloalkoxy, —C(O)C$_{1-4}$ alkyl, —C(O)C$_{3-10}$ cycloalkyl, —C(O)OC$_{1-4}$ alkyl, —C(O)OC$_{3-10}$ cycloalkyl, —C(O)NH$_2$, —C(O)NH(C$_{1-4}$ alkyl), —C(O)N(C$_{1-4}$ alkyl)$_2$, —C(O)NH(C$_{3-10}$ cycloalkyl), —C(O)N(C$_{3-10}$ cycloalkyl)$_2$, —S(O)$_2$C$_{1-4}$ alkyl, —S(O)$_2$C$_{3-10}$ cycloalkyl, —S(O)$_2$NH$_2$, —S(O)$_2$NH(C$_{1-4}$ alkyl), —S(O)$_2$N(C$_{1-4}$ alkyl)$_2$, —S(O)$_2$NH(C$_{3-10}$ cycloalkyl) and —S(O)$_2$N(C$_{3-10}$ cycloalkyl)$_2$;

each r is independently selected from 0, 1 and 2;
each t is independently selected from 0, 1, 2, 3 and 4;
each u is independently selected from 0, 1, 2, 3 and 4.

In some embodiments, Q is

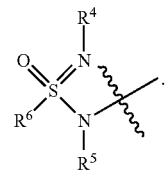

In some embodiments, Q is

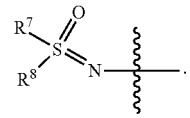

In some embodiments, Q is

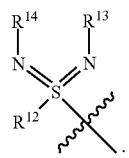

In some embodiments, Q is

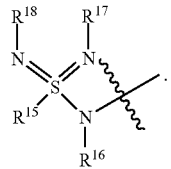

In some embodiments, Q is

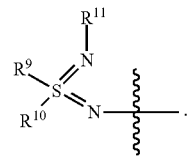

In some embodiments, L is —(CR$^{C1}$R$^{D1}$)$_t$—.
In some embodiments, t is selected from 2 and 3.
In some embodiments, L is selected from —(CH$_2$)$_2$—, —CHCH$_3$CH$_2$—, —CH$_2$CHCH$_3$— and —(CH$_2$)$_3$—.

In some embodiments, L is —(CR$^{C1}$R$^{D1}$)$_t$O(CR$^{C1}$R$^{D1}$)$_u$—.

In some embodiments, X is O.
In some embodiments, X is S.
In some embodiments, W is selected from aryl, wherein aryl is unsubstituted or substituted with at least one substituent independently selected from R$^X$.

In some embodiments, W is phenyl, wherein phenyl is unsubstituted or substituted with at least one substituent independently selected from R$^X$.

In some embodiments, W is phenyl, wherein phenyl is unsubstituted or substituted with at least one substituent independently selected from halogen, ethynyl, CN and —CF$_3$.

In some embodiments, W is heteroaryl, wherein heteroaryl is unsubstituted or substituted with at least one substituent independently selected from R$^X$.

In some embodiments, R$^1$ is hydrogen.
In some embodiments, R$^2$ is hydrogen.
In some embodiments, R$^3$ is hydrogen.
In some embodiments, R$^4$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^4$ is selected from hydrogen and methyl.

In some embodiments, R$^5$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^5$ is hydrogen.

In some embodiments, R$^6$ is selected from C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^6$ is selected from C$_{1-10}$ alkyl, wherein alkyl is unsubstituted or substituted with at least one substituent independently selected from R$^X$.

In some embodiments, R$^6$ is selected from methyl and ethyl.

In some embodiments, R$^7$ is selected from C$_{1-10}$ alkyl, wherein alkyl is unsubstituted or substituted with at least one substituent independently selected from R$^X$.

In some embodiments, R$^8$ is selected from C$_{1-10}$ alkyl, wherein alkyl is unsubstituted or substituted with at least one substituent independently selected from R$^X$.

In some embodiments, R$^7$ and R$^8$ together with the sulfur atom to which they are attached form a 4-12 membered ring containing 0, 1 or 2 additional heteroatoms independently selected from oxygen, sulfur and nitrogen, and optionally substituted with 1, 2 or 3 R$^X$ groups.

In some embodiments, R$^7$ and R$^8$ together with the sulfur atom to which they are attached form a 5-6 membered ring containing 0, 1 or 2 additional heteroatoms independently selected from oxygen, sulfur and nitrogen, and optionally substituted with 1, 2 or 3 R$^X$ groups.

In some embodiments, R$^9$ is selected from C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{10}$ is selected from C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^9$ and R$^{10}$ together with the sulfur atom to which they are attached form a 4-12 membered ring containing 0, 1 or 2 additional heteroatoms independently selected from oxygen, sulfur and nitrogen, and optionally substituted with 1, 2 or 3 R$^X$ groups.

In some embodiments, R$^{11}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{12}$ is selected from C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{12}$ is selected from C$_{1-10}$ alkyl, wherein alkyl is unsubstituted or substituted with at least one substituent independently selected from R$^X$.

In some embodiments, R$^{13}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{13}$ is hydrogen.

In some embodiments, R$^{14}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{14}$ is hydrogen.

In some embodiments, R$^{15}$ is selected from C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{16}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{17}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

In some embodiments, R$^{18}$ is selected from hydrogen, C$_{1-10}$ alkyl and C$_{3-10}$ cycloalkyl, wherein alkyl and cycloalkyl are independently unsubstituted or substituted with at least one substituent independently selected from R$^X$.

Also provided is a compound, selected from

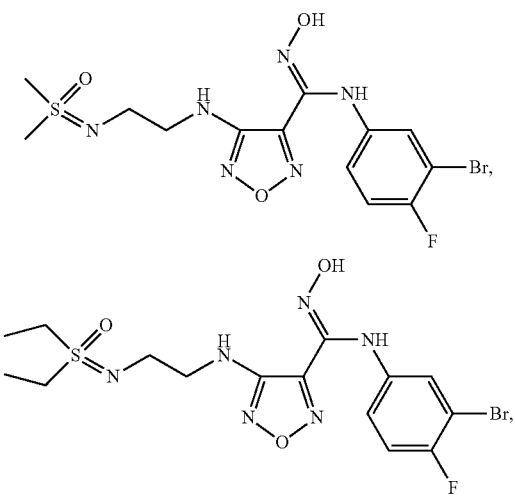

-continued

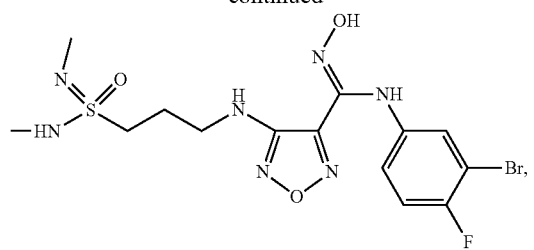
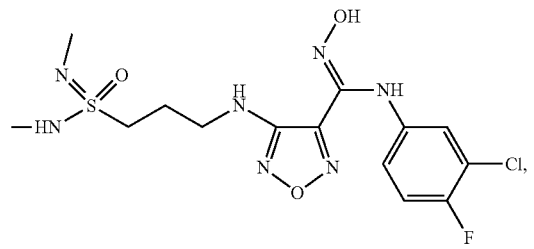
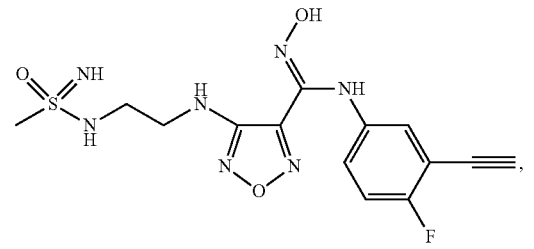
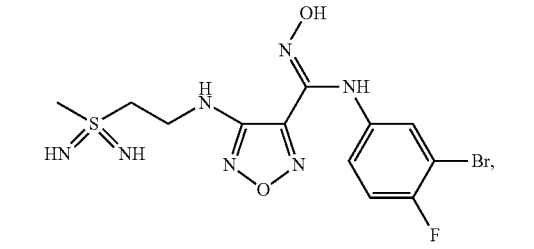
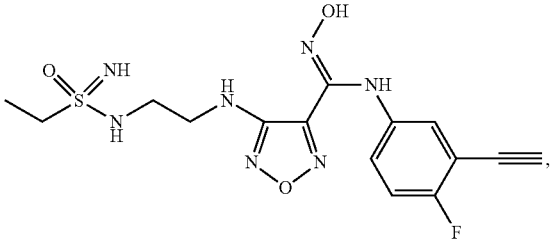
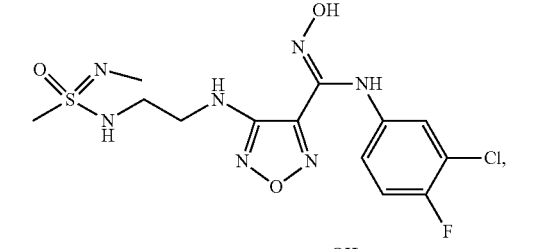
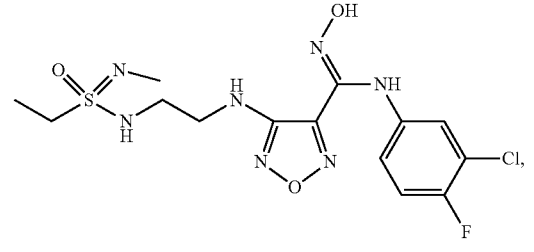
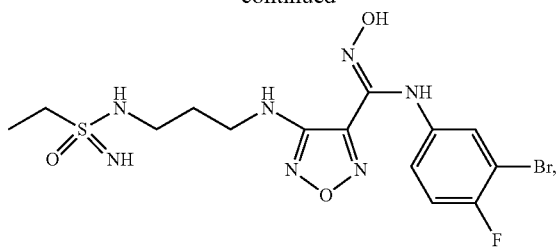
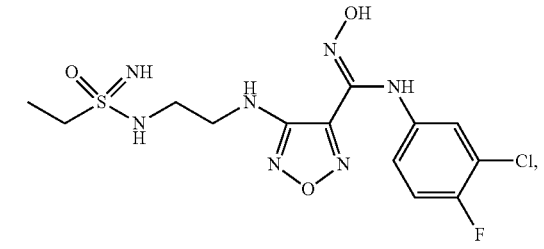
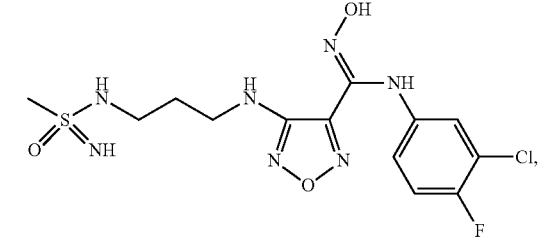
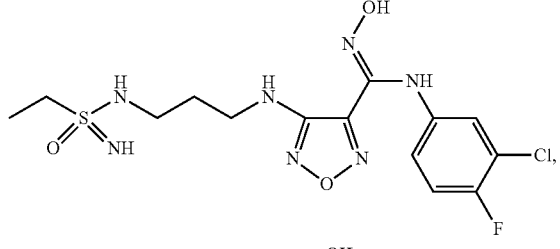
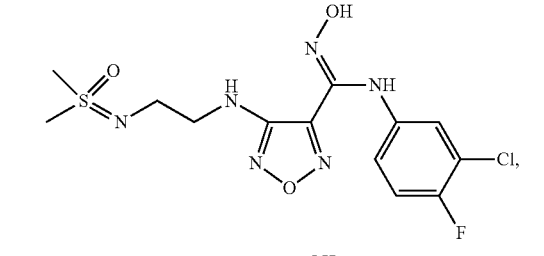
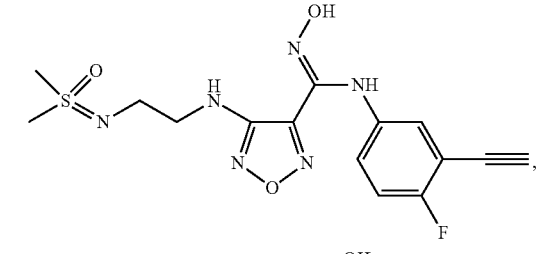
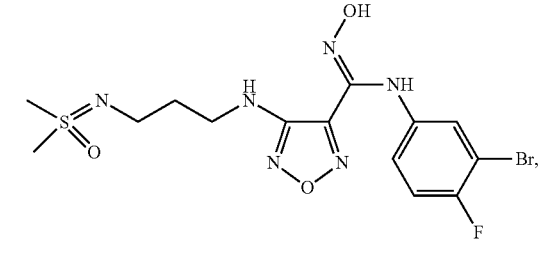

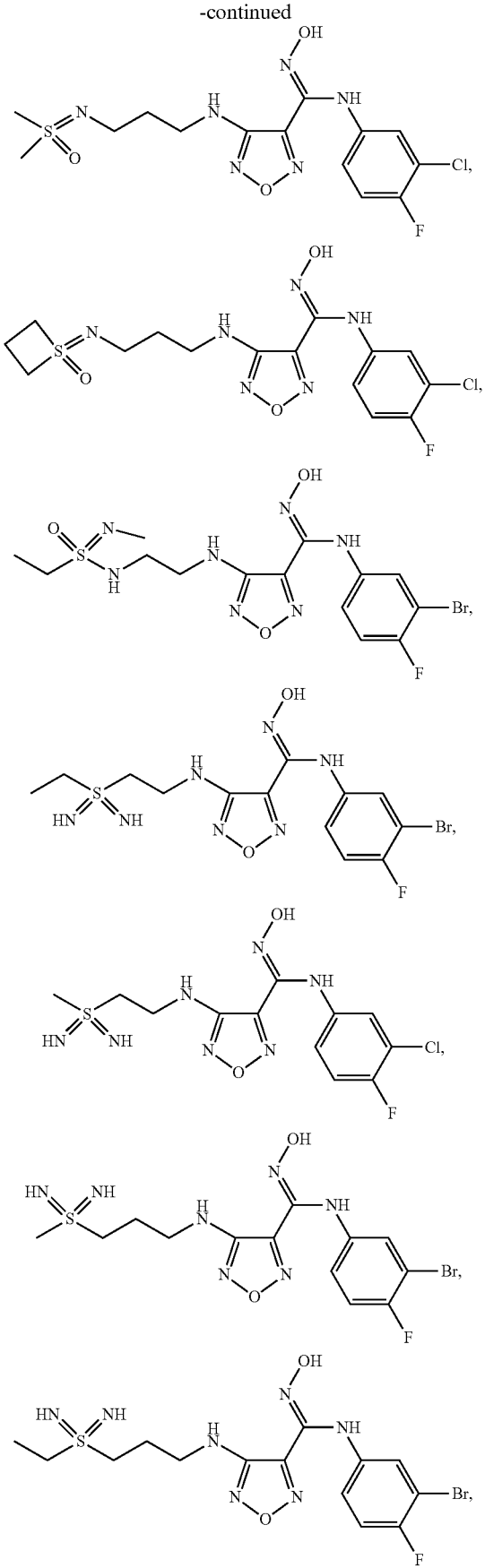
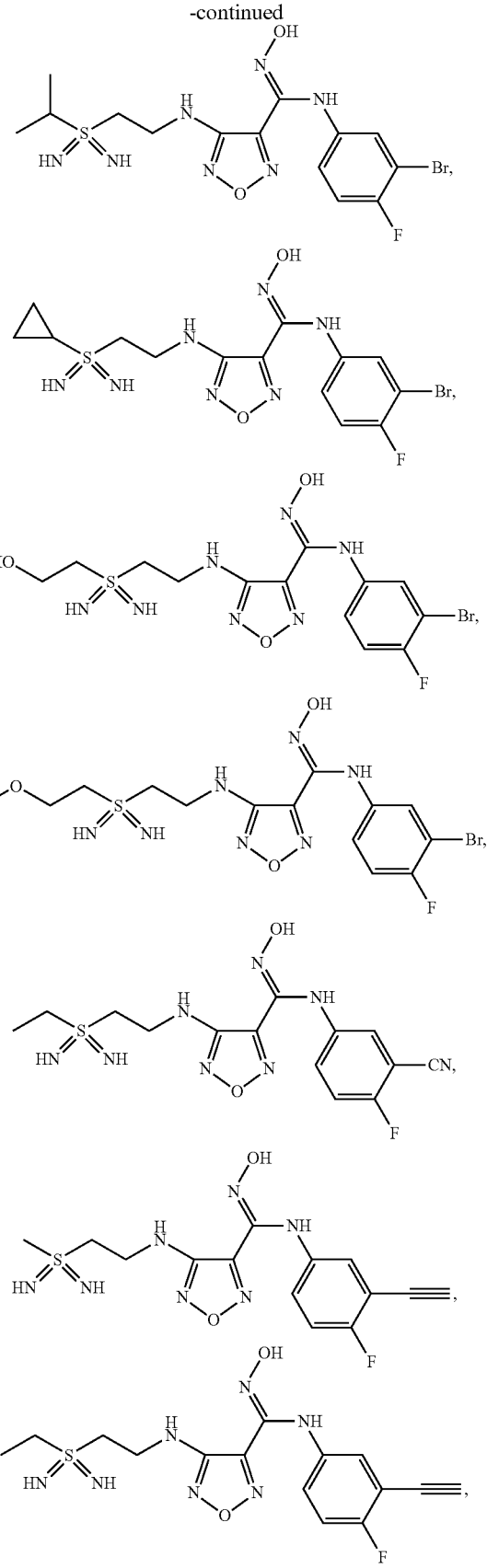
or a pharmaceutically acceptable salt thereof.

In yet another aspect, the present disclosure provides pharmaceutical compositions comprising a compound of formula (I) or at least one pharmaceutically acceptable salt thereof and a pharmaceutically acceptable excipient.

In yet another aspect, the disclosure provides methods for modulating IDO, comprising administering to a system or a subject in need thereof, a therapeutically effective amount of a compound of formula (I) or a pharmaceutically acceptable salt thereof or pharmaceutical compositions thereof, thereby modulating said IDO.

In yet another aspect, disclosed is a method to treat, ameliorate or prevent a condition which responds to inhibition of IDO comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a condition mediated by IDO. In particular embodiments, the compounds of the disclosure may be used alone or in combination with a second therapeutic agent to treat a condition mediated by IDO.

Alternatively, disclosed is a compound of formula (I) or a pharmaceutical acceptable salt thereof for treating a condition mediated by IDO.

Specifically, the condition herein includes but not limited to, is an autoimmune disease, a heteroimmune disease, an allergic disease, an inflammatory disease or a cell proliferative disorder.

Furthermore, the disclosure provides methods for treating a condition mediated by IDO, comprising administering to a system or subject in need of such treatment an effective amount of a compound of formula (I) or a pharmaceutically acceptable salt thereof or pharmaceutical compositions thereof, and optionally in combination with a second therapeutic agent, thereby treating said condition.

Alternatively, the present disclosure provides the use of a compound of formula (I) or a pharmaceutically acceptable salt thereof in the manufacture of a medicament for treating a condition mediated by IDO. In particular examples, the compounds of the disclosure may be used alone or in combination with a chemotherapeutic agent to treat said condition.

Specifically, the condition herein includes but not limited to, is an autoimmune disease, a heteroimmune disease, an allergic disease, an inflammatory disease or a cell proliferative disorder.

In certain embodiments, the condition is cell proliferative disorder. In one embodiment, the cell proliferative disorder is B-cell proliferative disorder, which includes but not limited to, B-cell chronic lymphocytic lymphoma, chronic lymphocytic leukemia, B-cell prolymphocytic leukemia, lymphoplasmacytic lymphoma, multiple sclerosis, small lymphocytic lymphoma, mantle cell lymphoma, B-cell non-Hodgkin's lymphoma, activated B-cell like diffuse large B-cell lymphoma, multiple myeloma, diffuse large B-cell lymphoma, follicular lymphoma, primary effusion lymphoma, burkitt lymphoma/leukemia, lymphomatoid granulomatosis, and plasmacytoma.

In certain embodiments, the condition is autoimmune disease, which includes but not limited to, rheumatoid arthritis, psoriatic arthritis, psoriasis, osteoarthritis, juvenile arthritis, inflammatory bowel disease, Crohn's disease, ulcerative colitis, myasthenia gravis, Hashimoto's thyroiditis, multiple sclerosis, acute disseminated encephalomyelitis, Addison's disease, ankylosing spondylitis, antiphospholipid antibody syndrome, aplastic anemia, autoimmune hepatitis, coeliac disease, Goodpasture's syndrome, idiopathic thrombocytopenic purpura, scleroderma, primary biliary cirrhosis, Reiter's syndrome, psoriasis, dysautonomia, neuromyotonia, interstitial cystitis, lupus, systemic lupus erythematosus, and lupus nephritis.

In certain embodiments, the condition is heteroimmune disease, which includes but not limited to, graft versus host disease, transplantation, transfusion, anaphylaxis, allergy, type I hypersensitivity, allergic conjunctivitis, allergic rhinitis, and atopic dermatitis.

In certain embodiments, the condition is inflammatory disease, which includes but not limited to, asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritic, phlebitis, pneumonitis, pneumonia, proctitis, prostatitis, pyelonephritis, rhinitis, salpingitis, sinusitis, stomatitis, synovitis, endonitis, tonsillitis, uveitis, vaginitis, vasculitis, and vulvitis.

In the above methods for using the compounds of the disclosure, a compound of formula (I) or a pharmaceutically acceptable salt thereof may be administered to a system comprising cells or tissues, or to a subject including a mammalian subject such as a human or animal subject.

Certain Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, $CH_2O$ is equivalent to $OCH_2$.

The term "substituted" means that a hydrogen atom is removed and replaced by a substituent. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-10}$, $C_{3-10}$, and the like.

The term "alkyl", employed alone or in combination with other terms, refers to both branched and straight-chain saturated aliphatic hydrocarbon groups having the specified number of carbon atoms. Unless otherwise specified, "alkyl" refers to $C_{1-10}$ alkyl. For example, $C_{1-6}$, as in "$C_{1-6}$ alkyl" is defined to include groups having 1, 2, 3, 4, 5, or 6 carbons in a linear or branched arrangement. For example, "$C_{1-8}$ alkyl" includes but is not limited to methyl, ethyl, n-propyl, i-propyl, n-butyl, t-butyl, i-butyl, pentyl, hexyl, heptyl, and octyl.

The term "cycloalkyl", employed alone or in combination with other terms, refers to a monocyclic or bridged hydrocarbon ring system. The monocyclic cycloalkyl is a carbocyclic ring system containing three to ten carbon atoms, zero heteroatoms and zero double bonds. Examples of monocyclic ring systems include cyclopropyl, cyclobutyl, cyclopentyl, cyclohexyl, cycloheptyl, and cyclooctyl. The monocyclic ring may contain one or two alkylene bridges, each consisting of one, two, or three carbon atoms, each linking two non-adjacent carbon atoms of the ring system. Representative examples of such bridged cycloalkyl ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.03,7]nonane, and tricyclo[3.3.1.13,7]decane (adamantane). The monocyclic and bridged cycloalkyl can be attached to the parent molecular moiety through any substitutable atom contained within the ring system.

The term "alkenyl", employed alone or in combination with other terms, refers to a non-aromatic hydrocarbon radical, straight, branched or cyclic, containing from 2 to 10 carbon atoms and at least one carbon to carbon double bond. In some embodiments, one carbon to carbon double bond is present, and up to four non-aromatic carbon-carbon double bonds may be present. Thus, "$C_{2-6}$ alkenyl" means an alkenyl radical having from 2 to 6 carbon atoms. Alkenyl groups include but are not limited to ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl", employed alone or in combination with other terms, refers to a hydrocarbon radical straight, branched or cyclic, containing from 2 to 10 carbon atoms and at least one carbon to carbon triple bond. In some embodiments, up to three carbon-carbon triple bonds may be present. Thus, "$C_{2-6}$ alkynyl" means an alkynyl radical having from 2 to 6 carbon atoms. Alkynyl groups include but are not limited to ethynyl, propynyl, butynyl, and 3-methylbutynyl. The straight, branched or cyclic portion of the alkynyl group may contain triple bonds and may be substituted if a substituted alkynyl group is indicated.

The term "halogen" (or "halo") refers to fluorine, chlorine, bromine and iodine.

The term "alkoxy", employed alone or in combination with other terms, refers to an alkyl radical that is single bonded to an oxygen atom. The attachment point of an alkoxy radical to a molecule is through the oxygen atom. An alkoxy radical may be depicted as —O-alkyl. The term "$C_{1-10}$ alkoxy" refers to an alkoxy radical containing from one to ten carbon atoms, having straight or branched moieties. Alkoxy groups, includes but is not limited to, methoxy, ethoxy, propoxy, isopropoxy, butoxy, pentyloxy, hexyloxy, and the like.

The term "cycloalkoxy", employed alone or in combination with other terms, refers to cycloalkyl radical that is single bonded to an oxygen atom. The attachment point of a cycloalkoxy radical to a molecule is through the oxygen atom. A cycloalkoxy radical may be depicted as —O-cycloalkyl. "$C_{3-10}$ cycloalkoxy" refers to a cycloalkoxy radical containing from three to ten carbon atoms. Cycloalkoxy groups, includes but is not limited to, cyclopropoxy, cyclobutoxy, cyclopentyloxy, cyclohexyloxy, and the like.

The term "alkylthio", employed alone or in combination with other terms, refers to an alkyl radical that is single bonded to a sulfur atom. The attachment point of an alkylthio radical to a molecule is through the sulfur atom. An alkylthio radical may be depicted as —S-alkyl. The term "$C_{1-10}$ alkylthio" refers to an alkylthio radical containing from one to ten carbon atoms, having straight or branched moieties. Alkylthio groups, includes but is not limited to, methylthio, ethylthio, propylthio, isopropylthio, butylthio, hexylthio, and the like.

The term "cycloalkylthio", employed alone or in combination with other terms, refers to cycloalkyl radical that is single bonded to a sulfur atom. The attachment point of a cycloalkylthio radical to a molecule is through the sulfur atom. A cycloalkylthio radical may be depicted as —S-cycloalkyl. "$C_{3-10}$ cycloalkylthio" refers to a cycloalkylthio radical containing from three to ten carbon atoms. Cycloalkylthio groups, includes but is not limited to, cyclopropylthio, cyclobutylthio, cyclohexylthio, and the like.

The term "alkylamino", employed alone or in combination with other terms, refers to an alkyl radical that is single bonded to a nitrogen atom. The attachment point of an alkylamino radical to a molecule is through the nitrogen atom. An alkylamino radical may be depicted as —NH(alkyl). The term "$C_{1-10}$ alkylamino" refers to an alkylamino radical containing from one to ten carbon atoms, having straight or branched moieties. Alkylamino groups, includes but is not limited to, methylamino, ethylamino, propylamino, isopropylamino, butylamino, hexylamoino, and the like.

The term "cycloalkylamino", employed alone or in combination with other terms, refers to cycloalkyl radical that is single bonded to a nitrogen atom. The attachment point of a cycloalkylamino radical to a molecule is through the nitrogen atom. A cycloalkylamino radical may be depicted as —NH(cycloalkyl). "$C_{3-10}$ cycloalkylamino" refers to a cycloalkylamino radical containing from three to ten carbon atoms. Cycloalkylamino groups, includes but is not limited to, cyclopropylamino, cyclobutylamino, cyclohexylamino, and the like.

The term "di(alkyl)amino", employed alone or in combination with other terms, refers to two alkyl radicals that are single bonded to a nitrogen atom. The attachment point of an di(alkyl)amino radical to a molecule is through the nitrogen atom. A di(alkyl)amino radical may be depicted as —N(alkyl)$_2$. The term "di($C_{1-10}$ alkyl)amino" refers to a di($C_{1-10}$ alkyl)amino radical wherein the alkyl radicals each independently contains from one to ten carbon atoms, having straight or branched moieties.

The term "aryl", employed alone or in combination with other terms, encompasses: 5- and 6-membered carbocyclic aromatic rings, for example, benzene; bicyclic ring systems wherein at least one ring is carbocyclic and aromatic, for example, naphthalene, indane, and 1, 2, 3, 4-tetrahydroquinoline; and tricyclic ring systems wherein at least one ring is carbocyclic and aromatic, for example, fluorene. In cases where the aryl substituent is bicyclic or tricyclic and at least one ring is non-aromatic, it is understood that attachment is via the aromatic ring.

For example, aryl includes 5- and 6-membered carbocyclic aromatic rings fused to a 5- to 7-membered heterocyclic ring containing one or more heteroatoms selected from N, O and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "heteroaryl", employed alone or in combination with other terms, refers to
  5- to 8-membered aromatic, monocyclic rings containing one or more, for example, from 1 to 4, or, in some embodiments, from 1 to 3, heteroatoms selected from N, O and S, with the remaining ring atoms being carbon;
  8- to 12-membered bicyclic rings containing one or more, for example, from 1 to 4, or, in some embodiments, from 1 to 3, heteroatoms selected from N, O and S, with the remaining ring atoms being carbon and wherein at least one heteroatom is present in an aromatic ring; and
  11- to 14-membered tricyclic rings containing one or more, for example, from 1 to 4, or in some embodiments, from 1 to 3, heteroatoms selected from N, O and S, with the remaining ring atoms being carbon and wherein at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Further heteroaryl groups include but are not limited to pyrrolyl, isothiazolyl, triazinyl, pyrazinyl, pyridazinyl, indolyl, benzotriazolyl, quinoxalinyl, and isoquinolinyl. As with the definition of heterocycle below, "heteroaryl" is also understood to include the N-oxide derivative of any nitrogen-containing heteroaryl.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In cases where the heteroaryl substituent is bicyclic or tricyclic and at least one ring is non-aromatic or contains no heteroatoms, it is understood that attachment is via the aromatic ring or via the heteroatom containing ring, respectively.

The term "heterocycle", employed alone or in combination with other terms, (and variations thereof such as "heterocyclic", or "heterocyclyl") broadly refers to a single aliphatic ring, usually with 3 to 12 ring atoms, containing at least 2 carbon atoms in addition to one or more, preferably one to three heteroatoms independently selected from oxygen, sulfur, nitrogen and phosphorus, as well as combinations comprising at least one of the foregoing heteroatoms. Alternatively, a heterocycle as defined above may be multicyclic ring system (e.g. bicyclic) in which two or more rings may be fused or bridged or spiro together, wherein at least one such ring contains one or more heteroatoms independently selected from oxygen, sulfur, nitrogen and phosphorus. "Heterocycle" also refers to 5- to 7-membered heterocyclic ring containing one or more heteroatoms selected from oxygen, sulfur, nitrogen and phosphorus fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring, provided that attachment results in the creation of a stable structure. When the heterocyclic ring has substituents, it is understood that the substituents may be attached to any atom in the ring, whether a heteroatom or a carbon atom, provided that a stable chemical structure results. Heterocycle does not overlap with heteroaryl.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl. 1,4-piperazinyl, and 2,3-pyridazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thio morpholinyl. Bicyclic heterocycles include, for example:

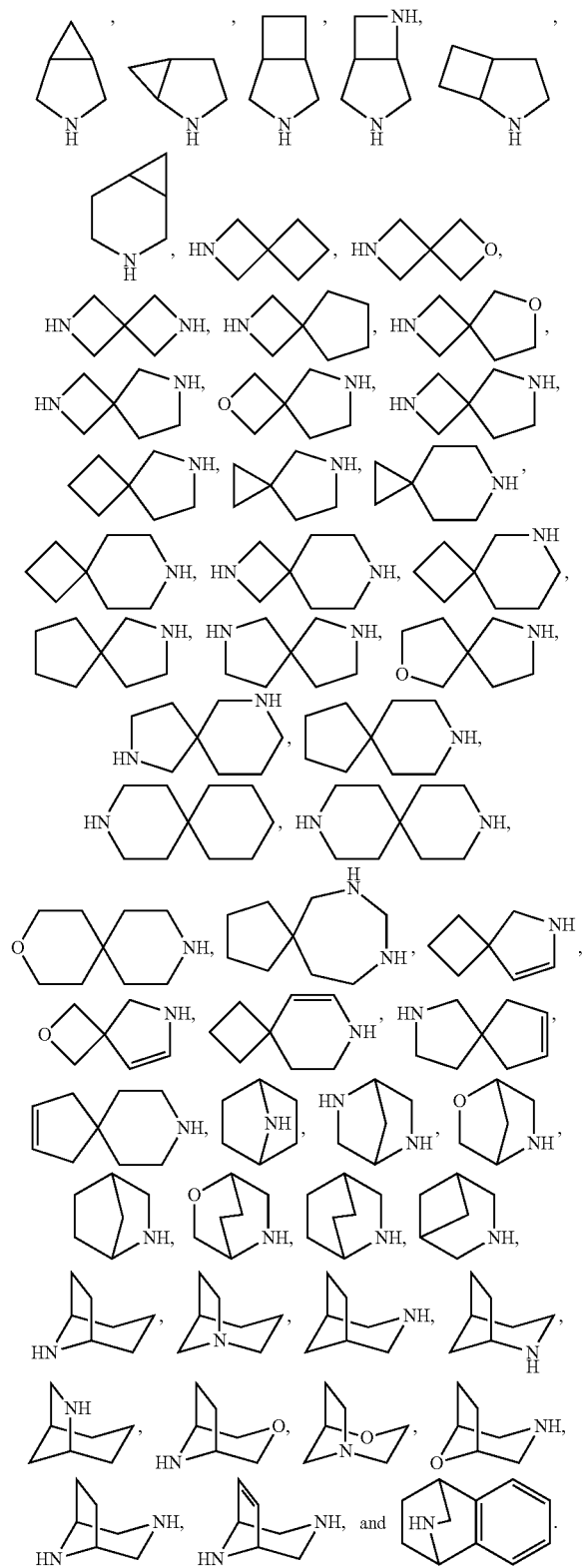

As used herein, "aryl-alkyl" refers to an alkyl moiety substituted by an aryl group. Example aryl-alkyl groups include benzyl, phenethyl, and naphthylmethyl groups. In some embodiments, aryl-alkyl groups have from 7 to 20 or 7 to 11 carbon atoms. When used in the phrase "aryl-$C_{1-4}$ alkyl", the term "CM" refers to the alkyl portion of the moiety and does not describe the number of atoms in the aryl portion of the moiety.

As used herein, "heterocyclyl-alkyl" refers to alkyl substituted by heterocyclyl. When used in the phrase "heterocyclyl-$C_{1-4}$ alkyl", the term "$C_{1-4}$" refers to the alkyl portion of the moiety and does not describe the number of atoms in the heterocyclyl portion of the moiety.

As used herein, "cycloalkyl-alkyl" refers to alkyl substituted by cycloalkyl. When used in the phrase "$C_{3-10}$ cycloalkyl-$C_{1-4}$ alkyl", the term "$C_{3-10}$" refers to the cycloalkyl portion of the moiety and does not describe the number of atoms in the alkyl portion of the moiety, and the term "$C_{1-4}$" refers to the alkyl portion of the moiety and does not describe the number of atoms in the cycloalkyl portion of the moiety.

As used herein, "heteroaryl-alkyl" refers to alkyl substituted by heteroaryl. When used in the phrase "heteroaryl-$C_{1-4}$ alkyl", the term "$C_{1-4}$" refers to the alkyl portion of the moiety and does not describe the number of atoms in the heteroaryl portion of the moiety.

For avoidance of doubt, reference, for example, to substitution of alkyl, cycloalkyl, heterocyclyl, aryl, and/or heteroaryl refers to substitution of each of those groups individually as well as to substitutions of combinations of those groups. That is, if $R^1$ is aryl-$C_{1-4}$ alkyl, the aryl portion may be unsubstituted or substituted with at least one substituent, such as one, two, three, or four substituents, independently selected from $R^X$ and the alkyl portion may also be unsubstituted or substituted with at least one substituent, such as one, two, three, or four substituents, independently selected from $R^X$.

The term "pharmaceutically acceptable salts" refers to salts prepared from pharmaceutically acceptable non-toxic bases or acids including inorganic or organic bases and inorganic or organic acids. Salts derived from inorganic bases may be selected, for example, from aluminum, ammonium, calcium, copper, ferric, ferrous, lithium, magnesium, manganic, manganous, potassium, sodium, and zinc salts. Further, for example, the pharmaceutically acceptable salts derived from inorganic bases may be selected from ammonium, calcium, magnesium, potassium, and sodium salts. Salts in the solid form may exist in one or more crystal structures, and may also be in the form of hydrates. Salts derived from pharmaceutically acceptable organic non-toxic bases may be selected, for example, from salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, and tripropylamine, tromethamine.

When the compound disclosed herein is basic, salts may be prepared using at least one pharmaceutically acceptable non-toxic acid, selected from inorganic and organic acids. Such acid may be selected, for example, from acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. In some embodiments, such acid may be selected, for example, from citric, hydrobromic, hydrochloric, maleic, phosphoric, sulfuric, fumaric, and tartaric acids.

The terms "administration of" and or "administering" a compound or a pharmaceutically acceptable salt should be understood to mean providing a compound or a pharmaceutically acceptable salt thereof to the individual in recognized need of treatment.

The term "effective amount" means the amount of the a compound or a pharmaceutically acceptable salt that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

The term "pharmaceutically acceptable" it is meant compatible with the other ingredients of the formulation and not unacceptably deleterious to the recipient thereof.

The term "subject" as used herein in reference to individuals suffering from a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition, ameliorating the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The term "protecting group" or "Pg" refers to a substituent that can be commonly employed to block or protect a certain functionality while reacting other functional groups on the compound. For example, an "amino-protecting group" is a substituent attached to an amino group that blocks or protects the amino functionality in the compound. Suitable amino-protecting groups include but are not limited to acetyl, trifluoroacetyl, t-butoxycarbonyl (BOC), benzyloxy carbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include but are not limited to acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl) ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The term "NH protecting group" as used herein includes, but not limited to, trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxy carbonyl, tert-butoxy carbonyl, para-methoxybenzyloxycarbonyl, 3,4-dimethoxybenzyl-oxy carbonyl, 4-(phenylazo)-benzyloxy carbonyl, 2-furfuryloxy carbonyl, diphenylmethoxy carbonyl, 1,1-dimethylpropoxy-carbonyl, isopropoxy carbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, M-Y-dimethylaminomethylene, benzylidene, 2-hydroxybenzylidene, 2-hydroxy-5-chlorobenzylidene, 2-hydroxy-1-naphthylmethylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclo-hexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group" as used herein includes, but not limited to, methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl) methyl, acetylmethyl, benzoylmethyl, para-nitrobenzoylmethyl, para-bromobenzoylmethyl, para-methanesulfonylbenzoylmethyl, 2-tetrahydropyranyl, 2-tetrahydrofuranyl, 2,2,2-trichloro-ethyl, 2-(trimethylsilyl) ethyl, acetoxymethyl, propionyloxymethy 1, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group" as used herein includes, but not limited to, benzyloxycarbonyl, 4-nitrobenzyloxycarbonyl, 4-bromobenzyloxy carbonyl, 4-methoxybenzyloxy carbonyl, 3,4-dimethoxybenzyloxy carbonyl, methoxy carbonyl, ethoxy carbonyl, tert-butoxy carbonyl, 1,1-dimethylpropoxy carbonyl, isopropoxy carbonyl, isobutyloxy carbonyl, diphenylmethoxycarbonyl, 2,2,2-trichloroethoxy carbonyl, 2,2,2-tribromoethoxy carbonyl, 2-(trimethylsilyl)ethoxy carbonyl, 2-(phenylsulfonyl)ethoxy carbonyl, 2-(triphenylphosphonio)ethoxy carbonyl, 2-furfuryloxy carbonyl, 1-adamantyloxycarbonyl, vinyloxy carbonyl, allyloxy carbonyl, 4-ethoxy-1-naphthyloxycarbonyl, 8-quinolyloxy carbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are designated as being of cis or trans configuration. Furthermore, the invention contemplates the various isomers and mixtures thereof resulting from the disposal of substituents around an adamantane ring system. Two substituents around a single ring within an adamantane ring system are designated as being of Z or E relative configuration. For examples, see C. D. Jones, M. Kaselj, R. N. Salvatore, W. J. le Noble J. Org. Chem. 1998, 63, 2758-2760.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85-90%, more preferably an excess of about 95-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, nitrogen, phosphorous, sulfur, fluorine, chlorine, and iodine include, but are not limited to, $^2H$, $^3H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuterated acid such as $D_2SO_4/D_2O$. In addition to the above, relevant procedures and intermediates are disclosed, for instance, in Lizondo, J et al, Drugs Put, 21(11), 1116 (1996); Brickner, S J et al., J Med Chem, 39(3), 673 (1996); Mallesham, B et al, Org Lett, 5(7), 963 (2003); PCI publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of IDO inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. J. Pharm. Sci. 64, 3, 367-391 (1975)). Such metabolic studies are important in the design of safe, effective therapeutic dmgs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al, J. Labelled Comp. Radiopharmaceut., 36(10):927-932 (1995); Kushner et al., Can. J. Physiol. Pharmacol, 77, 79-88 (1999)).

In addition, non-radioactive isotope containing drugs, such as deuterated drugs called "heavy drugs" can be used for the treatment of diseases and conditions related to IDO activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Marling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

In an Embodiment (1), this invention provides a compound of formula (I):

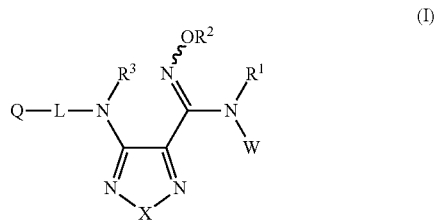

or a pharmaceutically acceptable salt thereof, wherein:
Q is selected from

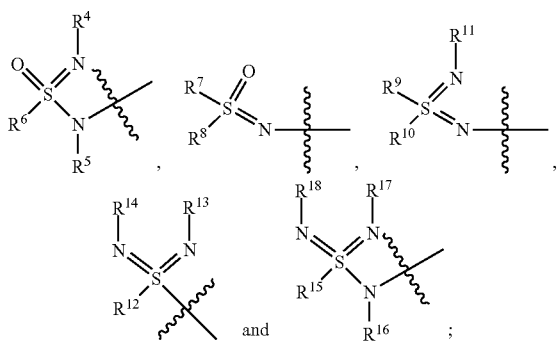

L is selected from $-(CR^{C1}R^{D1})_t-$ and $-(CR^{C1}R^{D1})_tO(CR^{C1}R^{D1})_u-$;

X is selected from O and S;

W is selected from aryl and heteroaryl, wherein aryl and heteroaryl are each unsubstituted or substituted with at least one substituent, such as one, two, three or four substituents, independently selected from $R^X$;

$R^1$, $R^2$, $R^3$, $R^4$, $R^5$, $R^{11}$, $R^{13}$, $R^{14}$, $R^{16}$, $R^{17}$ and $R^{18}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, $-CN$, $-NO_2$, $-(CR^{C2}R^{D2})_tNR^{A2}R^{B2}$, $-(CR^{C2}R^{D2})_tOR^{A2}$, $-(CR^{C2}R^{D2})_tS(O)_rR^{A2}$, $-(CR^{C2}R^{D2})_tS(O)_2OR^{A2}$, $-(CR^{C2}R^{D2})_tOS(O)_2R^{A2}$, $-(CR^{C2}R^{D2})_tP(O)R^{A2}R^{B2}$, $-(CR^{C2}R^{D2})_tP(O)(OR^{A2})(OR^{B2})$, $-(CR^{C2}R^{D2})_tC(O)R^{A2}$, $-(CR^{C2}R^{D2})_tC(O)OR^{A2}$, $-(CR^{C2}R^{D2})_tOC(O)R^{A2}$, $-(CR^{C2}R^{D2})_tC(O)NR^{A2}R^{B2}$, $-(CR^{C2}R^{D2})_tNR^{A2}C(O)R^{B2}$, $-(CR^{C2}R^{D2})_tOC(O)NR^{A2}R^{B2}$, $-(CR^{C2}R^{D2})_tNR^{A2}C(O)OR^{B2}$, $-(CR^{C2}R^{D2})_tNR^{A2}C(O)NR^{A2}R^{B2}$, $-(CR^{C2}R^{D2})_tNR^{A2}C(S)NR^{A2}R^{B2}$, $-(CR^{C2}R^{D2})_tS(O)_rNR^{A2}R^{B2}$, $-(CR^{C2}R^{D2})_tNR^{A2}S(O)_rR^{B2}$, $-(CR^{C2}R^{D2})_tNR^{A2}S(O)_2NR^{A2}R^{B2}$, $-(CR^{C2}R^{D2})_tS(O)(=NR^{E2})R^{B2}$, $-(CR^{C2}R^{D2})_tN=S(O)R^{A2}R^{B2}$, $-(CR^{C2}R^{D2})_tNR^{A2}S(O)(=NR^{E2})R^{B2}$, $-(CR^{C2}R^{D2})_tS(O)(=NR^{E2})NR^{A2}R^{B2}$, $-(CR^{C2}R^{D2})_tNR^{A2}S(O)(=NR^{E2})NR^{A2}R^{B2}$, $-(CR^{C2}R^{D2})_tC(=NR^{E2})R^{A2}$, $-(CR^{C2}R^{D2})_tC(=N-OR^{B2})R^{A2}$, $-(CR^{C2}R^{D2})_tC(=NR^{E2})NR^{A2}R^{B2}$, $-(CR^{C2}R^{D2})_tNR^{A2}C(=NR^{E2})R^{B2}$, and $-(CR^{C2}R^{D2})_tNR^{A2}C(=NR^{E2})NR^{A2}R^{B2}$, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

$R^6$, $R^7$, $R^8$, $R^9$, $R^{10}$, $R^{12}$ and $R^{15}$ are independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or $R^7$ and $R^8$ together with the sulfur atom to which they are attached form a 4-12 membered ring containing, 0, 1 or 2 additional heteroatoms independently selected from oxygen, sulfur and nitrogen, and optionally substituted with 1, 2 or 3 $R^X$ groups;

or $R^9$ and $R^{10}$ together with the sulfur atom to which they are attached form a 4-12 membered ring containing, 0, 1 or 2 additional heteroatoms independently selected from oxygen, sulfur and nitrogen, and optionally substituted with 1, 2 or 3 $R^X$ groups;

each $R^{A2}$ and $R^{B2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or $R^{A2}$ and $R^{B2}$ together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 $R^X$ groups;

each $R^{C1}$, $R^{C2}$, $R^{D1}$ and $R^{D2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^X$;

or "$R^{C1}$ and $R^{D1}$" or "$R^{C2}$ and $R^{D2}$" together with the carbon atom(s) to which they are attached form a ring of 3 to 12 members containing 0, 1, or 2 heteroatoms independently selected from oxygen, sulfur and nitrogen, and optionally substituted with 1 2, or 3 $R^X$ groups;

each $R^{E2}$ are independently selected from hydrogen, $C_{1-10}$ alkyl, CN, $NO_2$, $OR^{a1}$, $SR^{a1}$, $-S(O)_rR^{a1}$, $-S(O)_rNR^{a1}R^{b1}$, $-C(O)R^{a1}$, $-C(O)OR^{a1}$ and $-C(O)NR^{a1}R^{b1}$;

each $R^X$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-CN$, $-NO_2$, $-(CR^{c1}R^{d1})_tNR^{a1}R^{b1}$, $-(CR^{c1}R^{d1})_tOR^{b1}$, $-(CR^{c1}R^{d1})_tS(O)_rR^{b1}$, $-(CR^{c1}R^{d1})_tS(O)_2OR^{b1}$, $-(CR^{c1}R^{d1})_tOS(O)_2R^{b1}$, $-(CR^{c1}R^{d1})_tP(O)R^{a1}R^{b1}$, $-(CR^{c1}R^{d1})_tP(O)(OR^{a1})(OR^{b1})$, $-(CR^{c1}R^{d1})_tC(O)R^{a1}$, $-(CR^{c1}R^{d1})_tC(O)OR^{b1}$, $-(CR^{c1}R^{d1})_tOC(O)R^{b1}$, $-(CR^{c1}R^{d1})_tC(O)NR^{a1}R^{b1}$, $-(CR^{c1}R^{d1})_tNR^{a1}C(O)R^{b1}$, $-(CR^{c1}R^{d1})_tOC(O)NR^{a1}R^{b1}$, $-(CR^{c1}R^{d1})_tNR^{a1}C(O)OR^{b1}$, $-(CR^{c1}R^{d1})_tNR^{a1}C(O)NR^{a1}R^{b1}$, $-(CR^{c1}R^{d1})_t$ $NR^{a1}C(S)NR^{a1}R^{b1}$, $-(CR^{c1}R^{d1})_tS(O)_rNR^{a1}R^{b1}$, $-(CR^{c1}R^{d1})_tNR^{a1}S(O)_rR^{b1}$, $-(CR^{c1}R^{d1})_tNR^{a1}S(O)_2NR^{a1}R^{b1}$, $-(CR^{c1}R^{d1})_tS(O)(=NR^{e1})R^{b1}$, $-(CR^{c1}R^{d1})_tN=S(O)R^{a1}R^{b1}$, $-(CR^{c1}R^{d1})_tNR^{a1}S(O)(=NR^{e1})R^{b1}$, $-(CR^{c1}R^{d1})_tS(O)(=NR^{e1})NR^{a1}R^{b1}$, $-(CR^{c1}R^{d1})_tNR^{a1}S(O)(=NR^{e1})NR^{a1}R^{b1}$, $-(CR^{c1}R^{d1})_tC(=NR^{e1})R^{a1}$, $-(CR^{c1}R^{d1})_tC(=N-OR^{b1})R^{a1}$, $-(CR^{c1}R^{d1})_tC(=NR^{e1})NR^{a1}R^{b1}$, $-(CR^{c1}R^{d1})_tNR^{a1}C(=NR^{e1})R^{b1}$ and $-(CR^{c1}R^{d1})_tNR^{a1}C(=NR^{e1})NR^{a1}R^{b1}$, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

each $R^{a1}$ and each $R^{b1}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three or four substituents, independently selected from $R^Y$;

or $R^{a1}$ and $R^{b1}$ together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 $R^Y$ groups;

each $R^{C1}$ and each $R^{d1}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, heterocyclyl, aryl and heteroaryl are each unsubstituted or substituted with at least one substituent, such as one, two, three, or four substituents, independently selected from $R^Y$;

or $R^{c1}$ and $R^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 $R^Y$ groups;

each $R^{e1}$ is independently selected from hydrogen, $C_{1-10}$ alkyl, $C_{3-10}$ cycloalkyl, $C_{3-10}$ cycloalkyl-$C_{1-4}$ alkyl, CN, $NO_2$, $OR^{a2}$, $SR^{a2}$, $-S(O)_rR^{a2}$, $-S(O)_rNR^{a2}R^{b2}$, $-C(O)R^{a2}$, $-C(O)OR^{a2}$ and $-C(O)NR^{a2}R^{b2}$;

each $R^Y$ is independently selected from $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, heterocyclyl, heterocyclyl-$C_{1-4}$ alkyl, aryl, aryl-$C_{1-4}$ alkyl, heteroaryl, heteroaryl-$C_{1-4}$ alkyl, halogen, $-CN$, $-NO_2$, $-(CR^{c2}R^{d2})_tNR^{a2}R^{b2}$, $-(CR^{c2}R^{d2})_tOR^{b2}$, $-(CR^{c2}R^{d2})_tS(O)_rR^{b2}$, $-(CR^{c2}R^{d2})_tS(O)_2OR^{b2}$, $-(CR^{c2}R^{d2})_tOS(O)_2R^{b2}$, $-(CR^{c2}R^{d2})_tP(O)R^{a2}R^{b2}$, $-(CR^{c2}R^{d2})_tP(O)(OR^{a2})(OR^{b2})$, $-(CR^{c2}R^{d2})_tC(O)R^{a2}$, $-(CR^{c2}R^{d2})_tC(O)OR^{b2}$, $-(CR^{c2}R^{d2})_tOC(O)R^{b2}$, $-(CR^{c2}R^{d2})_tC(O)NR^{a2}R^{b2}$, $-(CR^{c2}R^{d2})_tNR^{a2}C(O)R^{b2}$, $-(CR^{c2}R^{d2})_tOC(O)NR^{a2}R^{b2}$, $-(CR^{c2}R^{d2})_tNR^{a2}C(O)OR^{b2}$, $-(CR^{c2}R^{d2})_tNR^{a2}C(O)NR^{a2}R^{b2}$, $-(CR^{c2}R^{d2})_tNR^{a2}C(S)NR^{a2}R^{b2}$, $-(CR^{c2}R^{d2})_tS(O)_rNR^{a2}R^{b2}$, $-(CR^{c2}R^{d2})_tNR^{a2}S(O)_rR^{b2}$, $-(CR^{c2}R^{d2})_tNR^{a2}S(O)_2NR^{a2}R^{b2}$, $-(CR^{c2}R^{d2})_tS(O)(=NR^{e2})R^{b2}$, $-(CR^{c2}R^{d2})_tN=S(O)R^{a2}R^{b2}$, $-(CR^{c2}R^{d2})_tNR^{a2}S(O)(=NR^{e2})R^{b2}$, $-(CR^{c2}R^{d2})_tS(O)(=NR^{e2})NR^{a2}R^{b2}$, $-(CR^{c2}R^{d2})_tNR^{a2}S(O)(=NR^{e2})NR^{a2}R^{b2}$, $-(CR^{c2}R^{d2})_tC(=NR^{e2})R^{a2}$, $-(CR^{c2}R^{d2})_tC(=N-OR^{b2})R^{a2}$, $-(CR^{c2}R^{d2})_tC(=NR^{e2})NR^{a2}R^{b2}$, $-(CR^{c2}R^{d2})_tNR^{a2}C(=NR^{e2})R^{b2}$ and $-(CR^{c2}R^{d2})_tNR^{a2}C(=NR^{e2})NR^{a2}R^{b2}$, wherein alkyl, alkenyl, alkynyl, cycloalkyl, heterocyclyl, aryl and heteroaryl are each unsubstituted or substituted with at least one substituent, such as one, two, three, or four substituents, independently selected from OH, CN, amino, halogen, $C_{1-10}$ alkyl, $C_{2-10}$ alkenyl, $C_{2-10}$ alkynyl, $C_{3-10}$ cycloalkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino and di($C_{1-10}$ alkyl)amino;

each $R^{a2}$ and each $R^{b2}$ are independently selected from hydrogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a2}$ and $R^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-10}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent, such as one, two, three, or four substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $-C(O)C_{1-4}$ alkyl, $-C(O)C_{3-10}$ cycloalkyl, $-C(O)OC_{1-4}$ alkyl, $-C(O)OC_{3-10}$ cycloalkyl, $-C(O)NH_2$, $-C(O)NH(C_{1-4}$ alkyl), $-C(O)N(C_{1-4}$ alkyl$)_2$, $-C(O)NH(C_{3-10}$ cycloalkyl), $-C(O)N(C_{3-10}$ cycloalkyl$)_2$, $-S(O)_2C_{1-4}$ alkyl, $-S(O)_2C_{3-10}$ cycloalkyl, $-S(O)_2NH_2$, $-S(O)_2NH(C_{1-4}$ alkyl), $-S(O)_2N(C_{1-4}$ alkyl$)_2$, $-S(O)_2NH(C_{3-10}$ cycloalkyl) and $-S(O)_2N(C_{3-10}$ cycloalkyl$)_2$;

each r is independently selected from 0, 1 and 2;
each t is independently selected from 0, 1, 2, 3 and 4;
each u is independently selected from 0, 1, 2, 3 and 4.

In another Embodiment (2), the invention provides a compound of Embodiment (1) or a pharmaceutically acceptable salt thereof, wherein Q is selected from

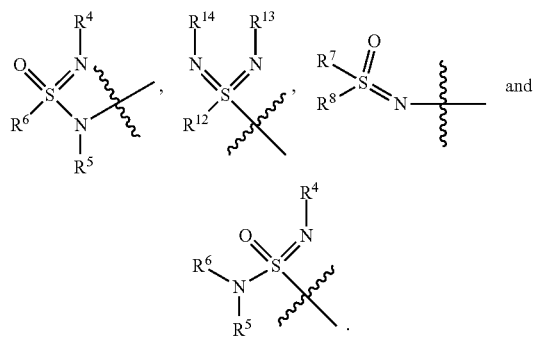

In another Embodiment (3), the invention provides a compound of any one of Embodiments (1)-(2) or a pharmaceutically acceptable salt thereof, wherein L is selected from —$(CH_2)_2$—, —$CHCH_3CH_2$—, —$CH_2CHCH_3$— and —$(CH_2)_3$—.

In another Embodiment (4), the invention provides a compound of any one of Embodiments (1)-(2) or a pharmaceutically acceptable salt thereof, wherein L is —$(CR^{C1}R^{D1})_tO(CR^{C1}R^{D1})_u$—.

In another Embodiment (5), the invention provides a compound of any one of Embodiments (1)-(4) or a pharmaceutically acceptable salt thereof, wherein X is O.

In another Embodiment (6), the invention provides a compound of any one of Embodiments (1)-(5) or a pharmaceutically acceptable salt thereof, wherein W is aryl, wherein aryl is unsubstituted or substituted with at least one substituent independently selected from $R^X$.

In another Embodiment (7), the invention provides a compound of Embodiment (6) or a pharmaceutically acceptable salt thereof, wherein W is phenyl, wherein phenyl is unsubstituted or substituted with at least one substituent independently selected from halogen, ethynyl, CN and —$CF_3$.

In another Embodiment (8), the invention provides a compound of any one of Embodiments (1)-(5) or a pharmaceutically acceptable salt thereof, wherein W is heteroaryl, wherein heteroaryl is unsubstituted or substituted with at least one substituent independently selected from $R^X$.

In another Embodiment (9), the invention provides a compound of any one of Embodiments (1)-(8) or a pharmaceutically acceptable salt thereof, wherein $R^1$ is hydrogen.

In another Embodiment (10), the invention provides a compound of any one of Embodiments (1)-(9) or a pharmaceutically acceptable salt thereof, wherein $R^2$ is hydrogen.

In another Embodiment (11), the invention provides a compound of any one of Embodiments (1)-(10) or a pharmaceutically acceptable salt thereof, wherein $R^3$ is hydrogen.

In another Embodiment (12), the invention provides a compound of any one of Embodiments (1)-(11) or a pharmaceutically acceptable salt thereof, wherein $R^4$, $R^5$, $R^{11}$, $R^{13}$, $R^{14}$, $R^{16}$, $R^{17}$ and $R^{18}$ are independently selected from hydrogen, $C_{1-10}$ alkyl and $C_{3-10}$ cycloalkyl, wherein alkyl and cycloalkyl are independently unsubstituted or substituted with at least one substituent independently selected from $R^X$.

In another Embodiment (13), the invention provides a compound of Embodiment (12) or a pharmaceutically acceptable salt thereof, wherein $R^4$ is selected from hydrogen and methyl.

In another Embodiment (14), the invention provides a compound of Embodiment (12) or a pharmaceutically acceptable salt thereof, wherein $R^5$ is hydrogen.

In another Embodiment (15), the invention provides a compound of Embodiment (12) or a pharmaceutically acceptable salt thereof, wherein $R^{13}$ and $R^{14}$ are hydrogen.

In another Embodiment (16), the invention provides a compound of any one of Embodiments (1)-(15) or a pharmaceutically acceptable salt thereof, wherein $R^6$, $R^7$, $R^8$, $R^9$, $R^{10}$, $R^{12}$ and $R^{15}$ are independently selected from $C_{1-10}$ alkyl and $C_{3-10}$ cycloalkyl, wherein alkyl and cycloalkyl are independently unsubstituted or substituted with at least one substituent independently selected from $R^X$.

In another Embodiment (17), the invention provides a compound of Embodiment (16) or a pharmaceutically acceptable salt thereof, wherein $R^6$, $R^7$ and $R^8$ are independently selected from methyl and ethyl.

In another Embodiment (18), the invention provides a compound of Embodiment (16) or a pharmaceutically acceptable salt thereof, wherein $R^{12}$ is selected from methyl, ethyl, isopropyl, cyclopropyl, hydroxyethyl and methoxyethyl.

In another Embodiment (19), the invention provides a compound of any one of Embodiments (1)-(15) or a pharmaceutically acceptable salt thereof, wherein $R^7$ and $R^8$ together with the sulfur atom to which they are attached form a 4-6 membered ring containing, 0, 1 or 2 additional heteroatoms independently selected from oxygen, sulfur and nitrogen, and optionally substituted with 1, 2 or 3 $R^X$ groups.

In another Embodiment (20), the invention provides a compound of any one of Embodiments (1)-(15) or a pharmaceutically acceptable salt thereof, wherein $R^9$ and $R^{10}$ together with the sulfur atom to which they are attached form a 4-12 membered ring containing, 0, 1 or 2 additional heteroatoms independently selected from oxygen, sulfur and nitrogen, and optionally substituted with 1, 2 or 3 $R^X$ groups.

In another Embodiment (21), the invention provides a compound selected from

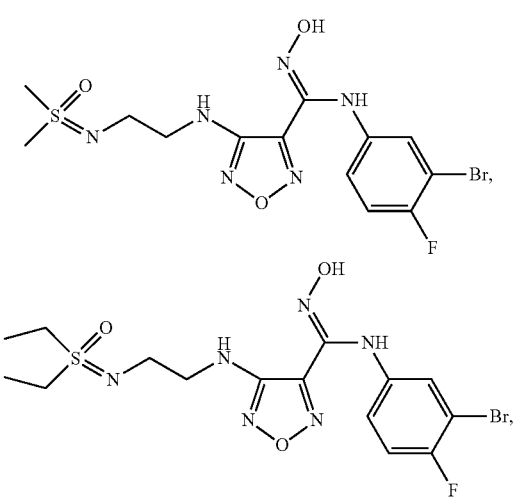

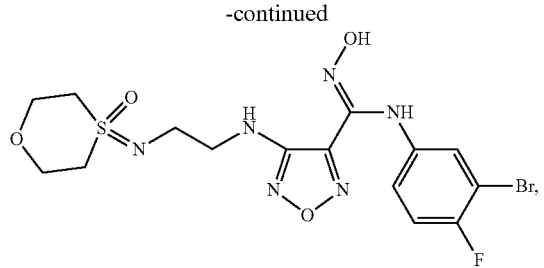
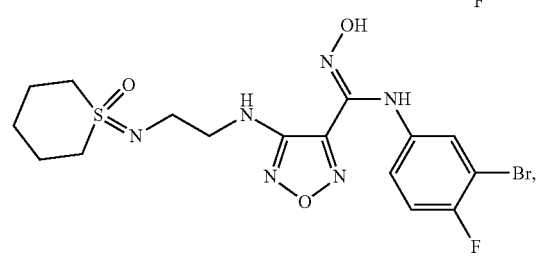
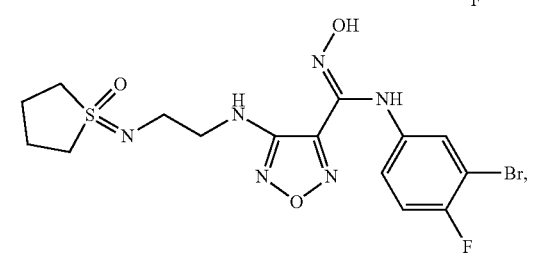
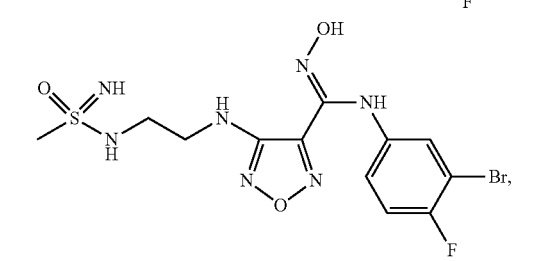
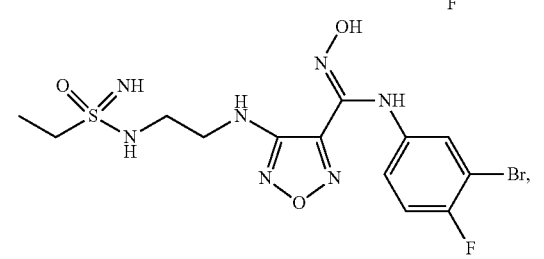
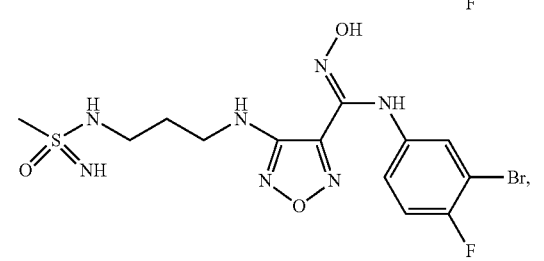
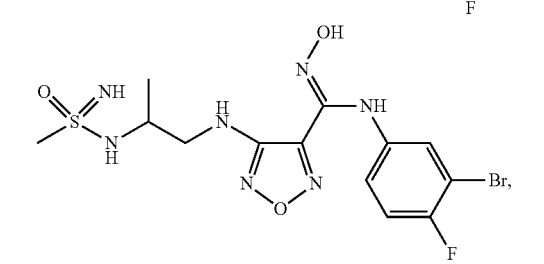
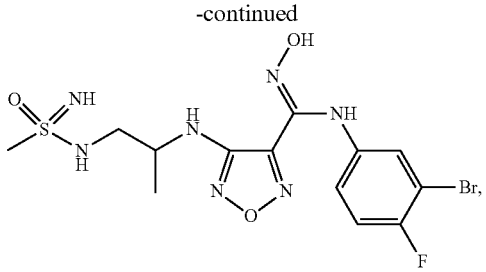
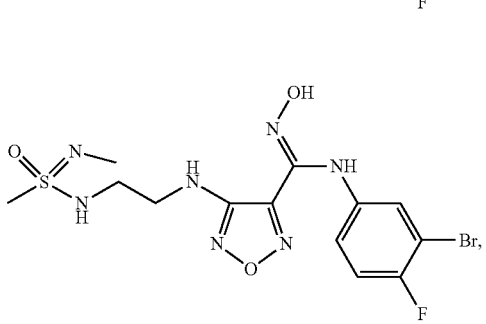
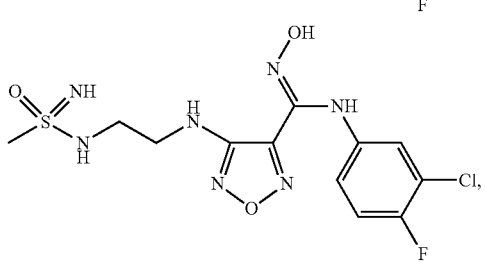
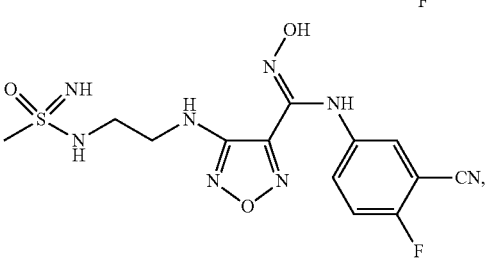
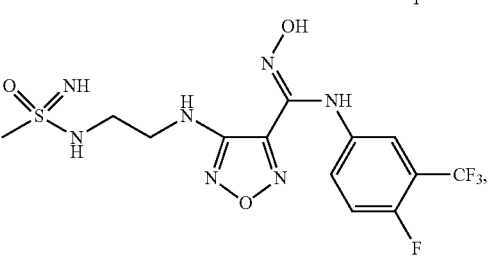
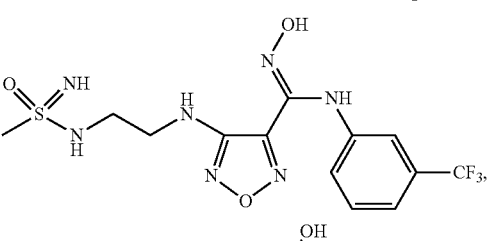
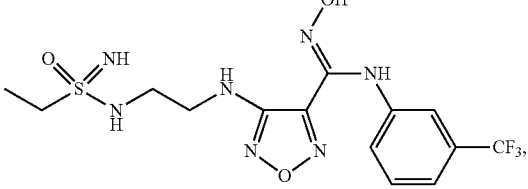

35
-continued
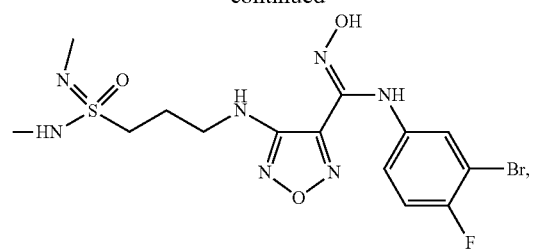
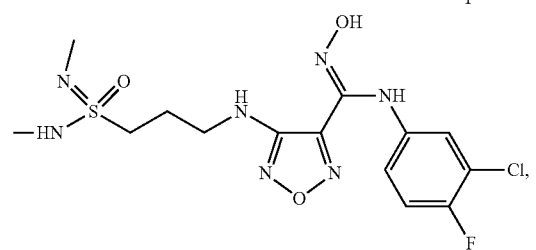
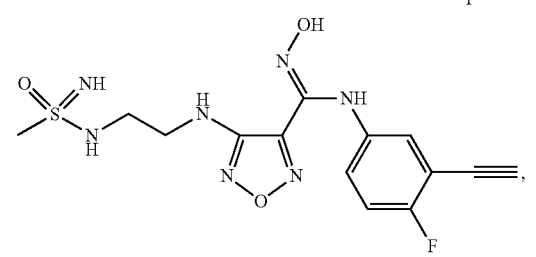
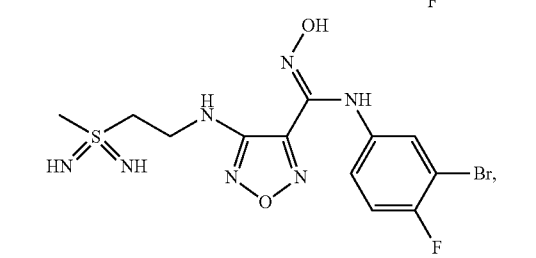
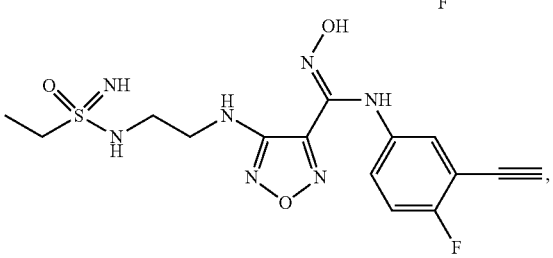 [SMILES: CCS(=N)(=O)NCCNc1nonc1/C(=N/O)Nc1ccc(F)c(Br)c1]
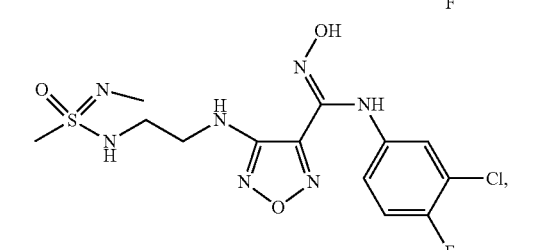
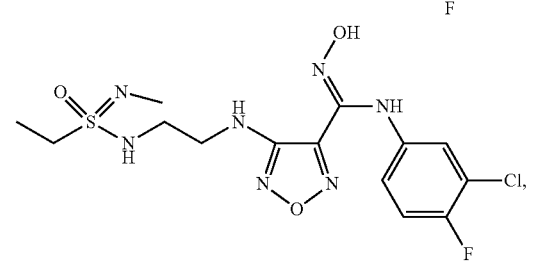
36
-continued
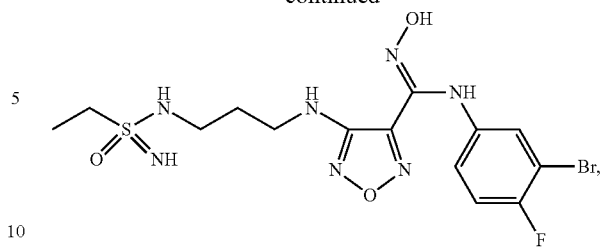
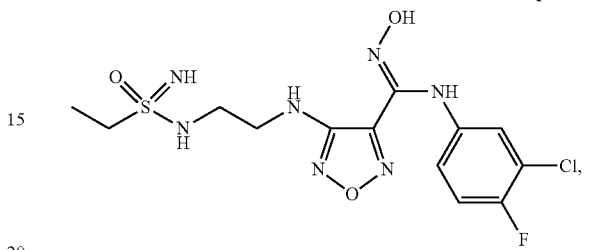
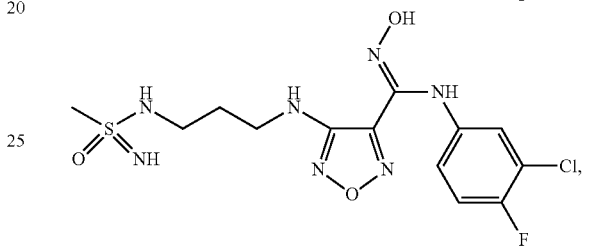
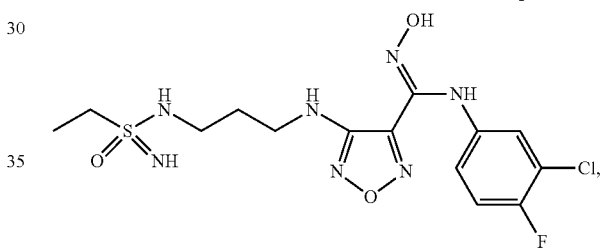
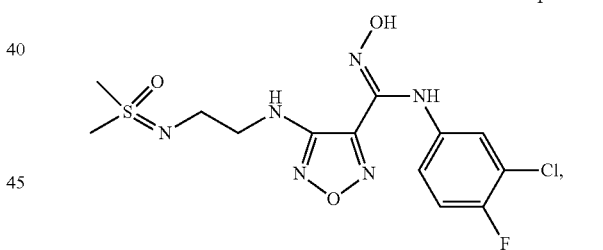
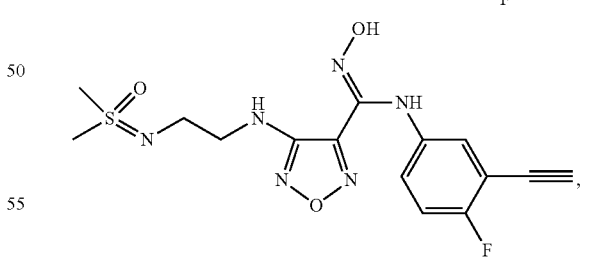
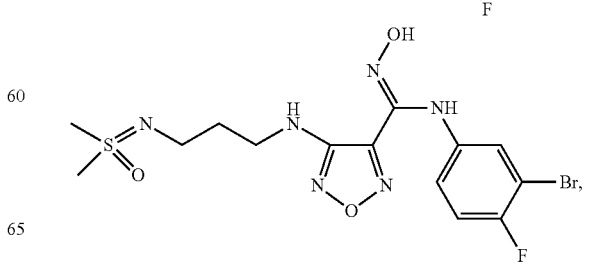

37
-continued
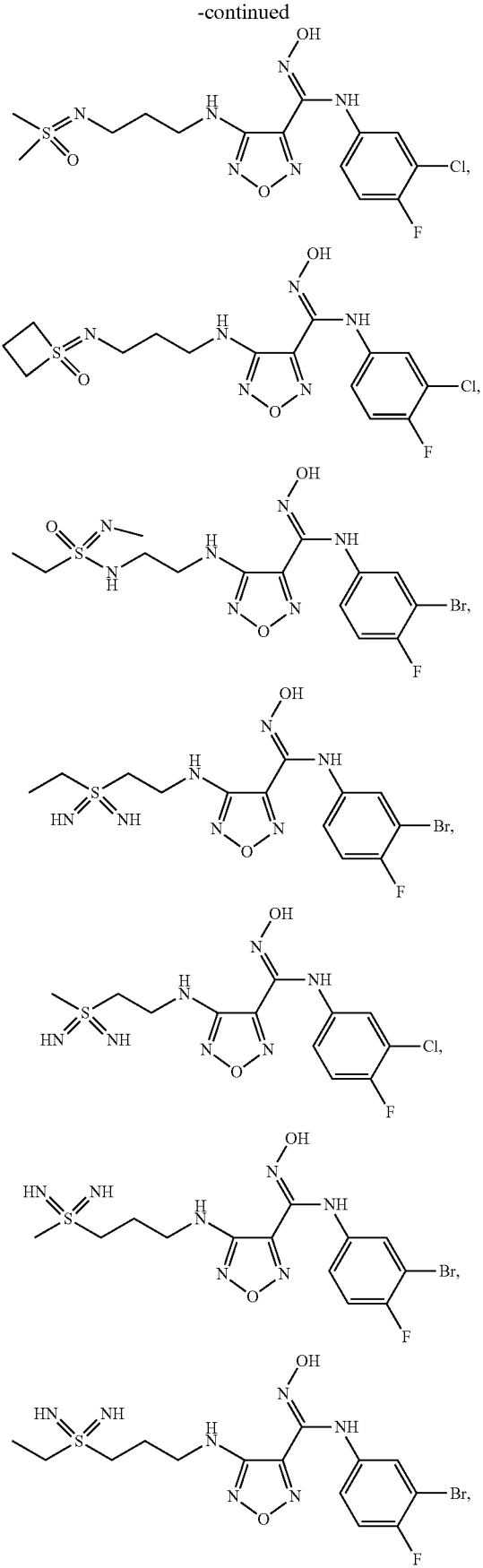
38
-continued
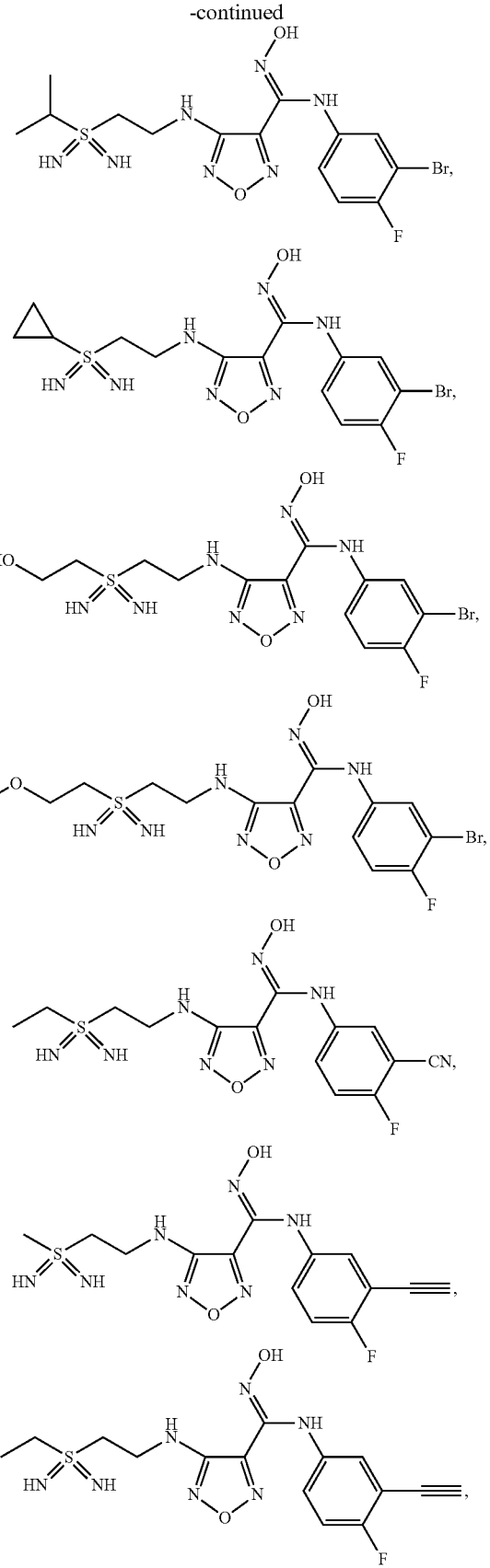
and pharmaceutically acceptable salts thereof.

In another Embodiment (22), the invention provides a pharmaceutical composition, comprising a compound of any one of Embodiments (1) to (21), or a pharmaceutically acceptable salt thereof, and at least one pharmaceutically acceptable carrier.

In another Embodiment (23), the invention provides a method of treating, ameliorating or preventing a condition, which responds to inhibition of indoleamine 2,3-dioxygenase, comprising administering to a subject in need of such treatment an effective amount of a compound of any one of Embodiments (1) to (21), or a pharmaceutically acceptable salt thereof, or of at least one pharmaceutical composition thereof, and optionally in combination with a second therapeutic agent.

In another Embodiment (24), the invention provides the use of a compound of any one of Embodiments (1) to (21) or a pharmaceutically acceptable salt thereof in the preparation of a medicament for treating a cell-proliferative disorder.

In yet another of its aspects, there is provided a kit comprising a compound disclosed herein, or a pharmaceutically acceptable salts thereof; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound disclosed herein, or a pharmaceutically acceptable salts thereof; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound disclosed herein, or a pharmaceutically acceptable salts thereof.

In another of its aspects, there is provided a method of inhibiting an IDO kinase comprising contacting the IDO with a compound disclosed herein, or a pharmaceutically acceptable salts thereof.

In yet another of its aspects, there is provided a method of inhibiting an IDO comprising causing a compound disclosed herein, or a pharmaceutically acceptable salts thereof to be present in a subject in order to inhibit the IDO in vivo.

In a further of its aspects, there is provided a method of inhibiting IDO comprising administering a first compound to a subject that is converted in vivo to a second compound wherein the second compound inhibits the IDO in vivo, the second compound being a compound according to any one of the above embodiments and variations.

In another of its aspects, there is provided a method of treating a disease state for which an IDO possesses activity that contributes to the pathology and/or symptomology of the disease state, the method comprising causing a compound disclosed herein, or a pharmaceutically acceptable salts thereof to be present in a subject in a therapeutically effective amount for the disease state.

In a further of its aspects, there is provided a method of treating a disease state for which an IDO possesses activity that contributes to the pathology and/or symptomology of the disease state, the method comprising administering a first compound to a subject that is converted in vivo to a second compound wherein the second compound inhibits the IDO in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, exzema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; chronic obstructive pulmonary disease (COPD) and other diseases.

In another of its aspects, there is provided a method of treating a disease state for which a mutation in the IDO gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament. In yet another of its aspects, the present invention relates to the use of a compound according to any one of the above embodiments and variations in the manufacture of a medicament for inhibiting IDO.

In a further of its aspects, the present invention relates to the use of a compound according to any one of the above embodiments and variations in the manufacture of a medicament for treating a disease state for which an IDO possesses activity that contributes to the pathology and/or symptomology of the disease state.

Administration and Pharmaceutical Compositions

In general, compounds of the disclosure will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors known to those of ordinary skill in the art. For example, for the treatment of neoplastic diseases and immune system disorders, the required dosage will also vary depending on the mode of administration, the particular condition to be treated and the effect desired.

In general, satisfactory results are indicated to be obtained systemically at daily dosages of from about 0.001 to about 100 mg/kg per body weight, or particularly, from about 0.03 to 2.5 mg/kg per body weight. An indicated daily dosage in the larger mammal, e.g. humans, may be in the range from about 0.5 mg to about 2000 mg, or more particularly, from about 0.5 mg to about 1000 mg, conveniently administered, for example, in divided doses up to four times a day or in retard form. Suitable unit dosage forms for oral administration comprise from ca. 1 to 50 mg active ingredient.

Compounds of the disclosure may be administered as pharmaceutical compositions by any conventional route; for example, enterally, e.g., orally, e.g., in the form of tablets or capsules; parenterally, e.g., in the form of injectable solutions or suspensions; or topically, e.g., in the form of lotions, gels, ointments or creams, or in a nasal or suppository form.

Pharmaceutical compositions comprising a compound of the present disclosure in free form or in a pharmaceutically acceptable salt form in association with at least one pharmaceutically acceptable carrier or diluent may be manufactured in a conventional manner by mixing, granulating, coating, dissolving or lyophilizing processes. For example, pharmaceutical compositions comprising a compound of the disclosure in association with at least one pharmaceutical acceptable carrier or diluent may be manufactured in conventional manner by mixing with a pharmaceutically acceptable carrier or diluent. Unit dosage forms for oral administration contain, for example, from about 0.1 mg to about 500 mg of active substance.

In one embodiment, the pharmaceutical compositions are solutions of the active ingredient, including suspensions or dispersions, such as isotonic aqueous solutions. In the case of lyophilized compositions comprising the active ingredient alone or together with a carrier such as mannitol, dispersions or suspensions can be made up before use. The pharmaceutical compositions may be sterilized and/or contain adjuvants, such as preserving, stabilizing, wetting or emulsifying agents, solution promoters, salts for regulating the osmotic pressure and/or buffers. Suitable preservatives include but are not limited to antioxidants such as ascorbic acid, or microbicides, such as sorbic acid or benzoic acid. The solutions or suspensions may further comprise viscosity-increasing agents, including but not limited to, sodium carboxymethylcellulose, carboxymethylcellulose, dextran, polyvinylpyrrolidone, gelatins, or solubilizers, e.g. Tween 80 (polyoxyethylene(20)sorbitan mono-oleate).

Suspensions in oil may comprise as the oil component the vegetable, synthetic, or semi-synthetic oils customary for injection purposes. Examples include liquid fatty acid esters that contain as the acid component a long-chained fatty acid having from 8 to 22 carbon atoms, or in some embodiments, from 12 to 22 carbon atoms. Suitable liquid fatty acid esters include but are not limited to lauric acid, tridecylic acid, myristic acid, pentadecylic acid, palmitic acid, margaric acid, stearic acid, arachidic acid, behenic acid or corresponding unsaturated acids, for example oleic acid, elaidic acid, emcic acid, brassidic acid and linoleic acid, and if desired, may contain antioxidants, for example vitamin E, 3-carotene or 3,5-di-tert-butyl-hydroxytoluene. The alcohol component of these fatty acid esters may have six carbon atoms and may be monovalent or polyvalent, for example a mono-, di- or trivalent, alcohol. Suitable alcohol components include but are not limited to methanol, ethanol, propanol, butanol or pentanol or isomers thereof; glycol and glycerol.

Other suitable fatty acid esters include but are not limited ethyl-oleate, isopropyl myristate, isopropyl palmitate, LABRAFIL® M 2375, (polyoxyethylene glycerol), LABRAFIL® M 1944 CS (unsaturated polyglycolized glycerides prepared by alcoholysis of apricot kernel oil and comprising glycerides and polyethylene glycol ester), LABRASOL™ (saturated polyglycolized glycerides prepared by alcoholysis of TCM and comprising glycerides and polyethylene glycol ester; all available from GaKefosse, France), and/or MIGLYOL® 812 (triglyceride of saturated fatty acids of chain length C8 to C12 from Hüls AG, Germany), and vegetable oils such as cottonseed oil, almond oil, olive oil, castor oil, sesame oil, soybean oil, or groundnut oil.

Pharmaceutical compositions for oral administration may be obtained, for example, by combining the active ingredient with one or more solid carriers, and if desired, granulating a resulting mixture, and processing the mixture or granules by the inclusion of additional excipients, to form tablets or tablet cores.

Suitable carriers include but are not limited to fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, carboxymethyl starch, crosslinked polyvinylpyrrolidone, alginic acid or a salt thereof, such as sodium alginate. Additional excipients include flow conditioners and lubricants, for example silicic acid, talc, stearic acid or salts thereof, such as magnesium or calcium stearate, and/or polyethylene glycol, or derivatives thereof.

Tablet cores may be provided with suitable, optionally enteric, coatings through the use of, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or tablet coatings, for example for identification purposes or to indicate different doses of active ingredient.

Pharmaceutical compositions for oral administration may also include hard capsules comprising gelatin or soft-sealed capsules comprising gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient may be dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories comprising a combination of the active ingredient and a suppository base. Suitable suppository bases are, for example, natural or synthetic triglycerides, paraffin hydrocarbons, polyethylene glycols or higher alkanols.

Pharmaceutical compositions suitable for parenteral administration may comprise aqueous solutions of an active ingredient in water-soluble form, for example of a water-soluble salt, or aqueous injection suspensions that contain viscosity-increasing substances, for example sodium carboxymethylcellulose, sorbitol and/or dextran, and, if desired, stabilizers.

The active ingredient, optionally together with excipients, can also be in the form of a lyophilizate and can be made into a solution before parenteral administration by the addition of suitable solvents. Solutions such as are used, for example, for parenteral administration can also be employed as infusion solutions. The manufacture of injectable preparations is usually carried out under sterile conditions, as is the filling, for example, into ampoules or vials, and the sealing of the containers.

The disclosure also provides for a pharmaceutical combinations, e.g. a kit, comprising a) a first agent which is a compound of the disclosure as disclosed herein, in free form or in pharmaceutically acceptable salt form, and b) at least one co-agent. The kit can comprise instructions for its administration.

Combination Therapies

The compounds or pharmaceutical acceptable salts of the disclosure may be administered as the sole therapy, or together with other therapeutic agent or agents.

For example, the therapeutic effectiveness of one of the compounds described herein may be enhanced by administration of an adjuvant (i.e. by itself the adjuvant may only have minimal therapeutic benefit, but in combination with another therapeutic agent, the overall therapeutic benefit to the individual is enhanced). Or, by way of example only, the benefit experienced by an individual may be increased by administering one of the compounds described herein with another therapeutic agent that also has therapeutic benefit. By way of example only, in a treatment for gout involving administration of one of the compounds described herein, increased therapeutic benefit may result by also providing the individual with another therapeutic agent for gout. Or, by way of example only, if one of the side effects experienced by an individual upon receiving one of the compounds described herein is nausea, then it may be appropriate to administer an anti-nausea agent in combination with the compound. Or, the additional therapy or therapies include, but are not limited to physiotherapy, psychotherapy, radiation therapy, application of compresses to a diseased area, rest, altered diet, and the like. Regardless of the disease, disorder or condition being treated, the overall benefit experienced by the individual may be additive of the two therapies or the individual may experience a synergistic benefit.

In the instances where the compounds described herein are administered in combination with other therapeutic agents, the compounds described herein may be administered in the same pharmaceutical composition as other therapeutic agents, or because of different physical and chemical characteristics, be administered by a different route. For example, the compounds described herein may be administered orally to generate and maintain good blood levels thereof, while the other therapeutic agent may be administered intravenously. Thus the compounds described herein may be administered concurrently, sequentially or dosed separately to other therapeutic agents.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, programmed death-1/programmed death ligand-1 (PD-1/PD-L1) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

EXAMPLES

Various methods may be developed for synthesizing a compound of formula (I) or a pharmaceutically acceptable salt thereof. Representative methods for synthesizing a compound of formula (I) or a pharmaceutically acceptable salt thereof are provided in the Examples. It is noted, however, that a compound of formula (I) or a pharmaceutically acceptable salt thereof may also be synthesized by other synthetic routes that others may devise.

It will be readily recognized that certain compounds of formula (I) have atoms with linkages to other atoms that confer a particular stereochemistry to the compound (e.g., chiral centers). It is recognized that synthesis of a compound of formula (I) or a pharmaceutically acceptable salt thereof may result in the creation of mixtures of different stereoisomers (enantiomers, diastereomers). Unless a particular stereochemistry is specified, recitation of a compound is intended to encompass all of the different possible stereoisomers.

A compound of formula (I) can also be prepared as a pharmaceutically acceptable acid addition salt by, for example, reacting the free base form of the at least one compound with a pharmaceutically acceptable inorganic or organic acid. Alternatively, a pharmaceutically acceptable base addition salt of the at least one compound of formula (I) can be prepared by, for example, reacting the free acid form of the at least one compound with a pharmaceutically acceptable inorganic or organic base. Inorganic and organic acids and bases suitable for the preparation of the pharmaceutically acceptable salts of compounds of formula (I) are set forth in the definitions section of this Application. Alternatively, the salt forms of the compounds of formula (I) can be prepared using salts of the starting materials or intermediates.

The free acid or free base forms of the compounds of formula (I) can be prepared from the corresponding base addition salt or acid addition salt form. For example, a compound of formula (I) in an acid addition salt form can be converted to the corresponding free base thereof by treating with a suitable base (e.g., ammonium hydroxide solution, sodium hydroxide, and the like). A compound of formula (I) in a base addition salt form can be converted to the corresponding free acid thereof by, for example, treating with a suitable acid (e.g., hydrochloric acid, etc).

The N-oxides of the a compound of formula (I) or a pharmaceutically acceptable salt thereof can be prepared by methods known to those of ordinary skill in the art. For example, N-oxides can be prepared by treating an unoxidized form of the compound of formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0 to 80° C. Alternatively, the N-oxides of the compounds of formula (I) can be prepared from the N-oxide of an appropriate starting material.

Compounds of formula (I) in an unoxidized form can be prepared from N-oxides of compounds of formula (I) by, for example, treating with a reducing agent (e.g., sulfur, sulfur dioxide, triphenyl phosphine, lithium borohydride, sodium borohydride, phosphorus trichloride, tribromide, and the like) in an suitable inert organic solvent (e.g., acetonitrile, ethanol, aqueous dioxane, and the like) at 0 to 80° C.

Protected derivatives of the compounds of formula (I) can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. For example, the following abbreviations may be used in the examples and throughout the specification: g (grams); mg (milligrams); L (liters); mL (milliliters); μL (microliters); psi (pounds per square inch); M (molar); mM (millimolar); i.v. (intravenous); Hz (Hertz); MHz (megahertz); mol (moles); mmol (millimoles); RT (room temperature); min (minutes); h (hours); mp (melting point); TLC (thin layer chromatography); Rt (retention time); RP (reverse phase); MeOH (methanol); i-PrOH (isopropanol); TEA (triethylamine); TEA (trifluoroacetic acid); TFAA (trifluoroacetic anhydride); THF (tetrahydrofuran); DMSO (dimethyl sulfoxide); EtOAc (ethyl acetate); DME (1,2-dimethoxy ethane); DCM (dichloromethane); DCE (dichloroethane); DMF (N,N-dimethylformamide); DMPU (N,N'-dimethylpropyleneurea); CDI (1,1-carbonyldiimidazole); IBCF (isobutyl chloroformate); HOAc (acetic acid); HOSu (N-hydroxysuccinimide); HOBT (1-hydroxybenzotriazole); Et$_2$O (diethyl ether); EDCI (1-(3-dimethylaminopropyl)-3-ethylcarbodiimide hydrochloride); BOC (tert-butyloxycarbonyl); FMOC (9-fluorenylmethoxycarbonyl); DCC (dicyclohexylcarbodiimide); CBZ (benzyloxycarbonyl); Ac (acetyl); atm (atmosphere); TMSE (2-(trimethylsilyl)ethyl); TMS (trimethylsilyl); TIPS (triisopropylsilyl); TBS (t-butyldimethylsilyl); DMAP (4-dimethylaminopyridine); Me (methyl); OMe (methoxy); Et (ethyl); tBu (tert-butyl); HPLC (high pressure liquid chromatography); BOP (bis(2-oxo-3-oxazolidinyl) phosphinic chloride); TBAF (tetra-n-butylammonium fluoride); m-CPBA (meta-chloroperbenzoic acid).

References to ether or Et$_2$O are to diethyl ether; brine refers to a saturated aqueous solution of NaCl. Unless otherwise indicated, all temperatures are expressed in ° C. (degrees Centigrade). All reactions were conducted under an inert atmosphere at RT unless otherwise noted.

$^1$H NMR spectra were recorded on a Varian Mercury Plus 400. Chemical shifts are expressed in parts per million (ppm). Coupling constants are in units of hertz (Hz). Splitting patterns describe apparent multiplicities and are designated as s (singlet), d (doublet), t (triplet), q (quartet), m (multiplet), and br (broad).

Low-resolution mass spectra (MS) and compound purity data were acquired on a Shimadzu LC/MS single quadrapole system equipped with electrospray ionization (ESI) source, UV detector (220 and 254 nm), and evaporative light scattering detector (ELSD). Thin-layer chromatography was performed on 0.25 mm Superchemgroup silica gel plates (60F-254), visualized with UV light, 5% ethanolic phosphomolybdic acid, ninhydrin, or p-anisaldehyde solution Flash column chromatography was performed on silica gel (200-300 mesh, Branch of Qingdao Haiyang Chemical Co., Ltd).

Synthetic Schemes

A compound of formula I or pharmaceutically acceptable salt thereof may be synthesized according to a variety of reaction schemes. Some illustrative schemes are provided below and in the examples. Other reaction schemes could be readily devised by those skilled in the art in view of the present disclosure.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Synthetic methods for preparing the compounds of the present invention are illustrated in the following Schemes and Examples. Starting materials are commercially available or may be made according to procedures known in the art or as illustrated herein.

The intermediates shown in the following schemes are either known in the literature or may be prepared by a variety of methods familiar to those skilled in the art.

As an illustration, one of the synthetic approach the compound of formula IA of the present disclosure is outlined in Scheme 1. As shown in the Scheme, the compound of formula IA can be prepared from IA-a via a sequence of manipulations. Reductive amination of IA-a with acetal IA-b leads to bromide IA-c which undergo nucleophilic displacement reaction on treatment with thio compound IA-d to give IA-e. Oxidative amination of thioether IA-e finally provides compounds of formula IA.

Scheme 1

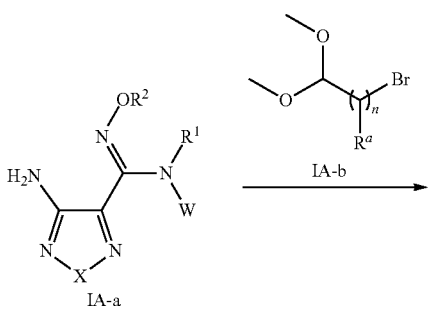

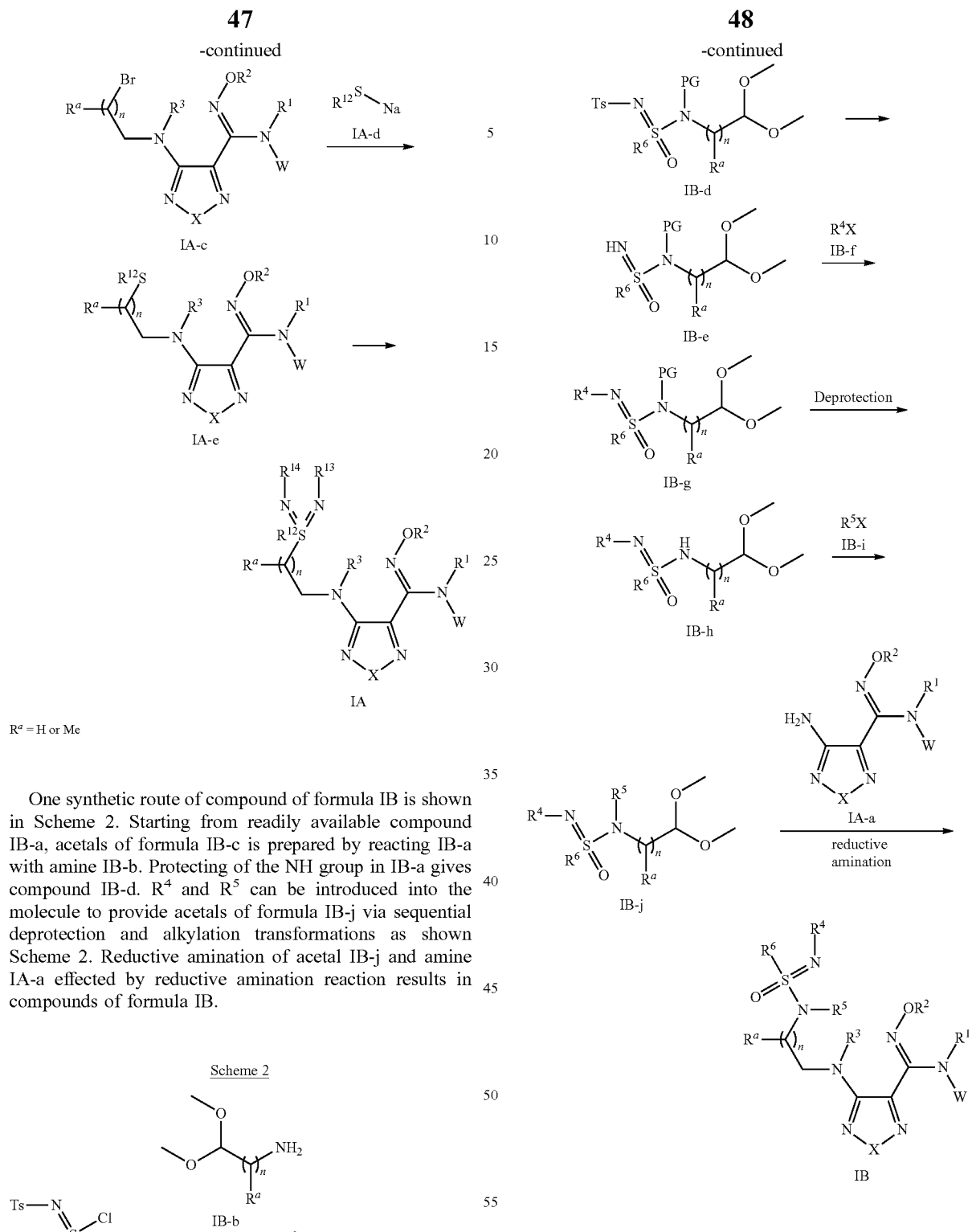

One synthetic route of compound of formula IB is shown in Scheme 2. Starting from readily available compound IB-a, acetals of formula IB-c is prepared by reacting IB-a with amine IB-b. Protecting of the NH group in IB-a gives compound IB-d. $R^4$ and $R^5$ can be introduced into the molecule to provide acetals of formula IB-j via sequential deprotection and alkylation transformations as shown Scheme 2. Reductive amination of acetal IB-j and amine IA-a effected by reductive amination reaction results in compounds of formula IB.

As a further illustration of compounds of formula I, the synthesis of compounds of formula IC is provided in Scheme 3. Reaction of sulfoxide IC-a with Chloramine-T gives IC-b which can be converted into IC-d through cleavage of the Tosyl group and N-alkylation with IA-b. Compounds of formula IC can be prepared from the reductive amination of acetal IC-d with amine IA-a.

Scheme 3

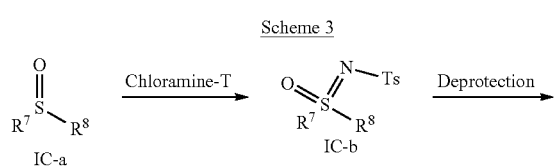

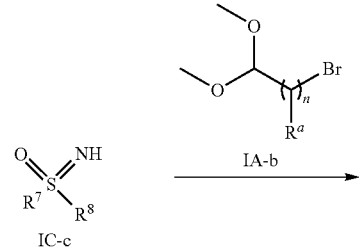

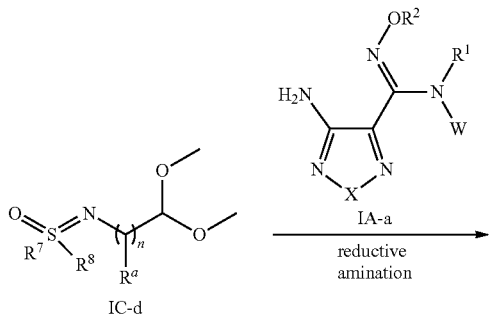

$R^a$ = H or Me

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Preparation of Intermediates

Intermediate A 3-(4-amino-1,2,5-oxadiazol-3-yl)-4-(3-bromo-4-fluorophenyl)-1,2,4-oxadiazol-5(4H)-one (Intermediate A)

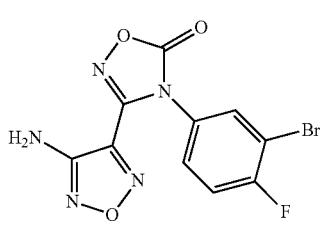

A

The title compound 3-(4-amino-1,2,5-oxadiazol-3-yl)-4-(3-bromo-4-fluorophenyl)-1,2,4-oxadiazol-5(4H)-one (Intermediate A) was prepared according to the method described in WO 2015070007.

Intermediate B 3-(4-amino-1,2,5-oxadiazol-3-yl)-4-(3-chloro-4-fluorophenyl)-1,2,4-oxadiazol-5(4H)-one (Intermediate B)

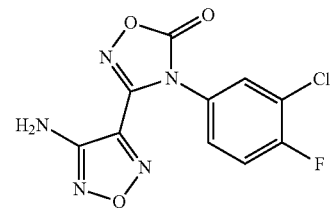

B (Z)-4-amino-N-hydroxy-1,2,5-oxadiazole-3-carbimidoyl chloride (B1)

The title compound (Z)-4-amino-N-hydroxy-1,2,5-oxadiazole-3-carbimidoyl chloride (B1) was prepared according to the method described in WO 2015070007.

(Z)-4-amino-N-(3-chloro-4-fluorophenyl)-N'-hydroxy-1,2,5-oxadiazole-3-carboximidamide (B2)

To a suspension of (Z)-4-amino-N-hydroxy-1,2,5-oxadiazole-3-carbimidoyl chloride (B1) (200 mg, 1.23 mmol) and 3-chloro-4-fluoroaniline (197 mg, 1.35 mmol) in water (4 ml) at 60° C. was added saturated NaHCO$_3$ aqueous solution (2 ml), followed by EA (2 ml). The resulting mixture was stirred at 60° C. for 30 min. After cooling to room temperature, the mixture was extracted with EA (2×5 mL). The organic phase was washed sequentially with 1 N HCl (2×5 mL) and brine (5 mL), dried and evaporated to give the title compound (Z)-4-amino-N-(3-chloro-4-fluorophenyl)-N'-hydroxy-1,2,5-oxadiazole-3-carboximidamide (B2). MS-ESI (m/z): 272 [M+1]$^+$.

3-(4-amino-1,2,5-oxadiazol-3-yl)-4-(3-chloro-4-fluorophenyl)-1,2,4-oxadiazol-5(4H)-one (B1)

A solution of (Z)-4-amino-N-(3-chloro-4-fluorophenyl)-N'-hydroxy-1,2,5-oxadiazole-3-carboximidamide (B2) (310 mg, 1.14 mmol) and CDI (277 mg, 1.71 mmol) in EA (4 ml) was stirred at 60° C. for 0.5 h. After cooling to room temperature, the mixture was diluted EA (20 ml), washed sequentially with 1 N HCl (2×5 mL) and brine (5 mL), dried and evaporated to give the title compound 3-(4-amino-1,2,5-oxadiazol-3-yl)-4-(3-chloro-4-fluorophenyl)-1,2,4-oxadiazol-5(4H)-one (Intermediate B).

Intermediate C 5-(3-(4-amino-1,2,5-oxadiazol-3-yl)-5-oxo-1,2,4-oxadiazol-4(5H)-yl)-2-fluorobenzonitrile (Intermediate C)

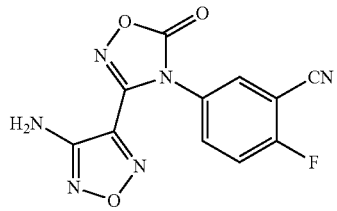

C

The title compound 5-(3-(4-amino-1,2,5-oxadiazol-3-yl)-5-oxo-1,2,4-oxadiazol-4(5H)-yl)-2-fluorobenzonitrile (Intermediate C) was prepared according to the synthetic method of B by replacing 3-chloro-4-fluoroaniline with 5-amino-2-fluorobenzonitrile.

Intermediate D 3-(4-amino-1,2,5-oxadiazol-3-yl)-4-(4-fluoro-3-(trifluoromethyl)phenyl)-1,2,4-oxadiazol-5(4H)-one (Intermediate D)

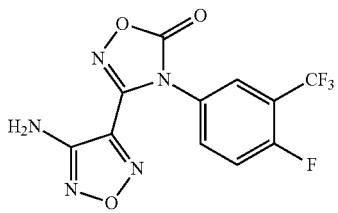

D

The title compound 3-(4-amino-1,2,5-oxadiazol-3-yl)-4-(4-fluoro-3-(trifluoro-methyl)phenyl)-1,2,4-oxadiazol-5 (4H)-one (Intermediate D) was prepared according to the synthetic method of B by replacing 3-chloro-4-fluoroaniline with 4-fluoro-3-(trifluoromethyl) aniline.

Intermediate E 3-(4-amino-1,2,5-oxadiazol-3-yl)-4-(3-(trifluoromethyl)phenyl)-1,2,4-oxadiazol-5(4H)-one (Intermediate E)

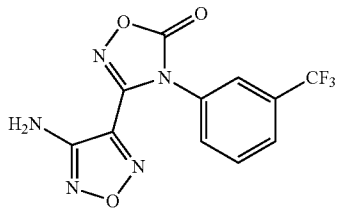

E

The title compound 3-(4-amino-1,2,5-oxadiazol-3-yl)-4-(3-(trifluoromethyl)-phenyl)-1,2,4-oxadiazol-5(4H)-one (Intermediate E) was prepared according to the synthetic method of B by replacing 3-chloro-4-fluoroaniline with 3-(trifluoromethyl)aniline.

Intermediate F 3-(4-amino-1,2,5-oxadiazol-3-yl)-4-(3-ethynyl-4-fluorophenyl)-1,2,4-oxadiazol-5 (4H)-one (Intermediate F)

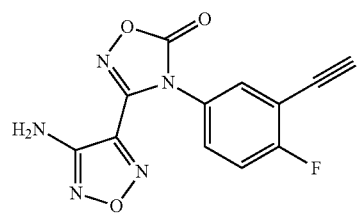

F

The title compound 3-(4-amino-1,2,5-oxadiazol-3-yl)-4-(3-ethynyl-4-fluoro-phenyl)-1,2,4-oxadiazol-5(4H)-one (Intermediate F) was prepared according to the synthetic method of B by replacing 3-chloro-4-fluoroaniline with 3-ethynyl-4-fluoroaniline.

Example 1

(Z)—N-(3-bromo-4-fluorophenyl)-4-((2-((dimethyl (oxo)-$\lambda^6$-sulfanylidene)amino)ethyl)amino)-N'-hydroxy-1,2,5-oxadiazole-3-carboximidamide (1)

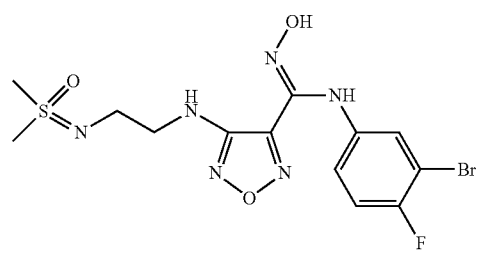

1

N-(dimethyl(oxo)-$\lambda^6$-sulfanylidene)-4-methylbenzenesulfonamide (1a)

The title compound N-(dimethyl(oxo)-$\lambda^6$-sulfanylidene)-4-methylbenzenesulfonamide (1a) was prepared according to the method described in Tetrahedron, 2014, 70, 6613.

Iminodimethyl-$\lambda^6$-sulfanone (1b)

To a suspension of N-(dimethyl(oxo)-$\lambda^6$-sulfanylidene)-4-methylbenzenesulfonamide (1a) (500 mg, 2.02 mmol) in DME (20 mL) at −50° C. was added naphthalen-1-ylsodium in DME (7.0 ml, 7.7 mmol) dropwise. After stirred at −50° C. for 30 min, the reaction was quenched with 1 N HCl (0.5 mL) at −30° C., and the mixture was concentrated. The residue was purified by flash column chromatography on silica gel eluting with DCM/MeOH/NH$_3$H$_2$O (20:1:0.05) to give the title compound iminodimethyl-λ$^6$-sulfanone (1b). MS-ESI (m/z): 94 [M+1]$^+$.

((2,2-dimethoxyethyl)imino)dimethyl-λ$^6$-sulfanone (1c)

The solution of iminodimethyl-λ$^6$-sulfanone (1b) (101 mg, 1.09 mmol) in 2-bromo-1,1-dimethoxyethane (1 mL) at room temperature was added NaHCO$_3$ (184 mg, 2.19 mmol), followed by NaI (163 mg, 1.09 mmol), and the resulting mixture was stirred at 120° C. for 24 h. Then the mixture was filtered, and the filtrate was purified by flash column chromatography on silica gel eluting with DCM/MeOH (100:1) to give the title compound ((2,2-dimethoxyethyl)imino)dimethyl-λ$^6$-sulfanone (1c). MS-ESI (m/z): 182 [M+1]$^+$.

4-(3-bromo-4-fluorophenyl)-3-(4-((2-((dimethyl(oxo)-λ$^6$-sulfanylidene)amino)ethyl)amino)-1,2,5-oxadiazol-3-yl)-1,2,4-oxadiazol-5(4H)-one (1d)

To a suspension of ((2,2-dimethoxyethyl)imino)dimethyl-λ$^6$-sulfanone (1c) (72.1 mg, 0.398 mmol) and 3-(4-amino-1,2,5-oxadiazol-3-yl)-4-(3-bromo-4-fluorophenyl)-1,2,4-oxadiazol-5(4H)-one (Intermediate A) (136 mg, 0.398 mmol) in DCM (1 mL) at room temperature was added MeSO$_3$H (1 ml), followed by Et$_3$SiH (1 ml), and the resulting solution was stirred at room temperature for 30 min. Then the mixture was poured into saturated NaHCO$_3$ aqueous solution (10 ml). The resulting mixture was extracted with DCM (3×10 mL), washed with brine, dried over Na$_2$SO$_4$ and concentrated. The residue was purified by flash column chromatography on silica gel eluting with DCM/MeOH (20:1) to give the title compound 4-(3-bromo-4-fluorophenyl)-3-(4-((2-((dimethyl(oxo)-λ$^6$-sulfanylidene)amino)ethyl)amino)-1,2,5-oxadiazol-3-yl)-1,2,4-oxadiazol-5(4H)-one (1d). MS-ESI (m/z): 461 [M+1]$^+$.

(Z)—N-(3-bromo-4-fluorophenyl)-4-((2-((dimethyl(oxo)-λ$^6$-sulfanylidene)amino)ethyl)amino)-N'-hydroxy-1,2,5-oxadiazole-3-carboximidamide (1)

To a solution of 4-(3-bromo-4-fluorophenyl)-3-(4-((2-((dimethyl(oxo)-λ$^6$-sulfanylidene)amino)ethyl)amino)-1,2,5-oxadiazol-3-yl)-1,2,4-oxadiazol-5(4H)-one (1d) (43 mg, 0.093 mmol) in THF (3 mL) at room temperature was added 5% NaOH aqueous solution (1.5 ml). The mixture was stirred at room temperature for 40 min. Then, the mixture was adjusted to pH=3 using 10% H$_3$PO$_4$ aqueous solution, and diluted with water (10 ml), extracted with DCM (3×10 mL), washed with brine, dried over Na$_2$SO$_4$, and evaporated. The residue was purified by column chromatography on silica gel eluting with DCM/MeOH (10:1) to give the title compound (Z)—N-(3-bromo-4-fluorophenyl)-4-((2-((dimethyl(oxo)-λ$^6$-sulfanylidene)amino)ethyl)amino)-N'-hydroxy-1,2,5-oxadiazole-3-carboximidamide (1). MS-ESI (m/z): 435 [M+1]$^+$.

Example 2

(Z)—N-(3-bromo-4-fluorophenyl)-4-((2-((diethyl(oxo)-N-sulfanylidene)amino)ethyl)amino)-N'-hydroxy-1,2,5-oxadiazole-3-carboximidamide (2)

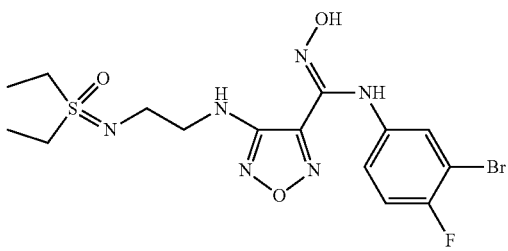

N-(diethyl-λ$^4$-sulfanylidene)cyanamide (2a)

To a solution of diethylsulfane (2.90 g, 30.0 mmol), NH$_2$CN (1.64 g, 39.0 mmol), and t-BuOK (4.04 g, 36.0 mmol) in MeOH (180 mL) at room temperature was added NBS (8.01 g, 45.0 mmol). The resulting mixture was stirred at room temperature overnight, diluted with saturated Na$_2$S$_2$O$_3$ aqueous solution (200 mL), and extracted with DCM (3×50 mL). The organic phase was washed brine (50 mL), dried over Na$_2$SO$_4$ and evaporated. The residue was purified by column chromatography on silica gel eluting with DCM/Acetone (20:1-5:1) to give title compound N-(diethyl-λ$^4$-sulfanylidene)cyanamide (2a). MS-ESI (m/z): 131 [M+1]$^+$.

N-(diethyl(oxo)-λ$^6$-sulfanylidene)cyanamide (2b)

To a solution of N-(diethyl-λ$^4$-sulfanylidene)cyanamide (2a) (1.31 g, 10.0 mmol) in EtOH (100 mL) at 0° C., was added K$_2$CO$_3$ (4.14 g, 30.0 mmol), followed by m-CPBA (3.45 g, 15.0 mmol). The resulting mixture was stirred at room temperature for 1 h. The solvent was removed under reduced pressure, diluted with water (100 ml), and extracted with DCM (4×50 mL). The organic phase was washed brine (50 mL), dried over Na$_2$SO$_4$ and evaporated. The residue was purified by column chromatography on silica gel eluting with PE/EA (1:1-1:3) to give title compound N-(diethyl(oxo)-λ$^6$-sulfanylidene)cyanamide (2b). MS-ESI (m/z): 147 [M+1]$^+$.

Diethyl(imino)-λ$^6$-sulfanone (2c)

To a solution of N-(diethyl(oxo)-λ$^6$-sulfanylidene)cyanamide (2b) (620 mg, 4.22 mmol) in DCM (76 mL) at 0° C., was added TFAA (1.8 ml, 12.7 mmol). The resulting mixture was stirred at room temperature for 1 h. Then the solvent was removed under reduced pressure. The residue was diluted in MeOH (30 ml), and K$_2$CO$_3$ (2.91 g, 21.1 mmol) was added. The resulting mixture was stirred at room temperature overnight. The solvent was removed under reduced pressure, and the residue was purified by column chromatography on silica gel eluting with EA/Acetone (2:1) to give title compound diethyl(imino)-λ$^6$-sulfanone (2c). MS-ESI (m/z): 122 [M+1]$^+$.

(Z)—N-(3-bromo-4-fluorophenyl)-4-((2-((diethyl(oxo)-λ⁶-sulfanylidene)amino)ethyl)amino)-N'-hydroxy-1,2,5-oxadiazole-3-carboximidamide (2)

The title compound (Z)—N-(3-bromo-4-fluorophenyl)-4-((2-((diethyl(oxo)-λ⁶-sulfanylidene)amino)ethyl)amino)-N'-hydroxy-1,2,5-oxadiazole-3-carboximidamide (2) was prepared according to the synthetic method of 1 by replacing iminodimethyl-λ⁶-sulfanone (1b) with diethyl(imino)-λ⁶-sulfanone (2c). MS-ESI (m/z): 463 [M+1]⁺.

Example 3

(Z)—N-(3-bromo-4-fluorophenyl)-N'-hydroxy-4-(#2-((4-oxido-1,4λ⁶-oxathian-4-ylidene)amino)ethyl)amino)-1,2,5-oxadiazole-3-carboximidamide (3)

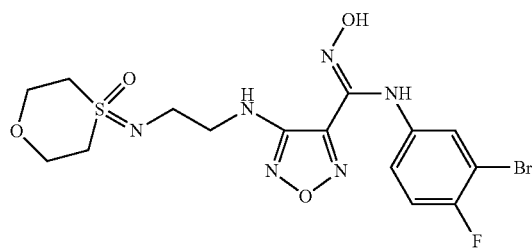

The title compound (Z)—N-(3-bromo-4-fluorophenyl)-N'-hydroxy-4-((2-((4-oxido-1,4λ⁶-oxathian-4-ylidene)amino)ethyl)amino)-1,2,5-oxadiazole-3-carboximidamide (3) was prepared according to the synthetic method of 2 by replacing diethylsulfane with 1,4-oxathiane. MS-ESI (m/z): 477 [M+1]⁺.

Example 4

(Z)—N-(3-bromo-4-fluorophenyl)-N'-hydroxy-4-((2-((1-oxidotetrahydro-2H-1λ⁶-thiopyran-1-ylidene)amino)ethyl)amino)-1,2,5-oxadiazole-3-carboximidamide (4)

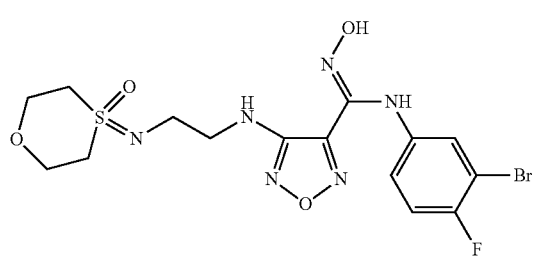

The title compound (Z)—N-(3-bromo-4-fluorophenyl)-N-hydroxy-4-((2-((1-oxidotetrahydro-2H-1λ⁶-thiopyran-1-ylidene)amino)ethyl)amino)-1,2,5-oxadiazole-3-carboximidamide (4) was prepared according to the synthetic method of 2 by replacing diethylsulfane with tetrahydro-2H-thiopyran. MS-ESI (m/z): 475 [M+1]⁺.

Example 5

(Z)—N-(3-bromo-4-fluorophenyl)-N'-hydroxy-4-((2-((1-oxidotetrahydro-1λ⁶-thiophen-1-ylidene)amino)ethyl)amino)-1,2,5-oxadiazole-3-carboximidamide (5)

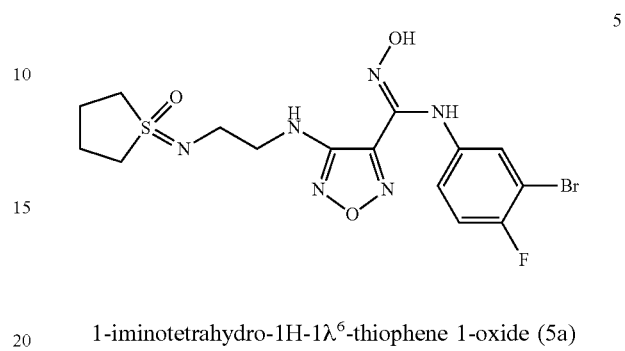

1-iminotetrahydro-1H-1λ⁶-thiophene 1-oxide (5a)

The title compound 1-iminotetrahydro-1H-1λ⁶-thiophene 1-oxide (5a) was prepared according to the method described in *Angew. Chem. Int. Ed.* 2016, 55, 7203.

(Z)—N-(3-bromo-4-fluorophenyl)-N'-hydroxy-4-((2-((1-oxidotetrahydro-1λ⁶-thiophen-1-ylidene)amino)ethyl)amino)-1,2,5-oxadiazole-3-carboximidamide (5)

The title compound (Z)—N-(3-bromo-4-fluorophenyl)-N'-hydroxy-4-((2-((1-oxidotetrahydro-1λ⁶-thiophen-1-ylidene)amino)ethyl)amino)-1,2,5-oxadiazole-3-carboximidamide (5) was prepared according to the synthetic method of 1 by replacing iminodimethyl-λ⁶-sulfanone (1b) with 1-iminotetrahydro-1H-1λ⁶-thiophene 1-oxide (5a). MS-ESI (m/z): 461 [M+1]⁺.

Example 6

(Z)—N-(3-bromo-4-fluorophenyl)-N'-hydroxy-4-((2-(methylsulfonoimidamido)ethyl)amino)-1,2,5-oxadiazole-3-carboximidamide (6)

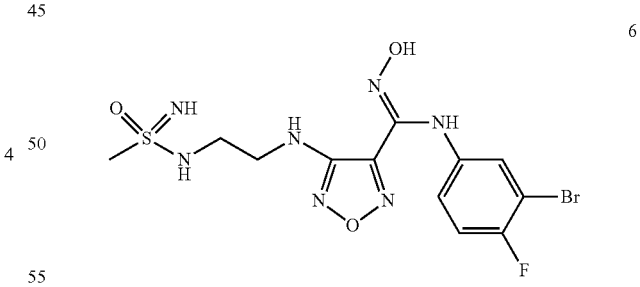

N-Tosylmethanesulfonimidoyl Chloride (6a)

The title compound N-tosylmethanesulfonimidoyl chloride (6a) was prepared according to the method described in WO2014/018355.

N-(((2,2-dimethoxyethyl)amino)(methyl)(oxo)-λ⁶-sulfanylidene)-4-methylbenzene sulfonamide (6b)

To a solution of 2,2-dimethoxyethan-1-amine (2.1 g, 20 mmol) and N-tosylmethanesulfonimidoyl chloride (6a)

(6.43 g, 24 mmol) in DCM (40 ml) at 0° C., was added TEA (4.2 ml, 30 mmol) dropwise. The resulting mixture was stirred at 0° C. for 1 h. Then, the mixture was quenched with cold water (100 ml), and extracted with DCM (3×50 mL). The organic phase was washed brine (50 mL), dried over $Na_2SO_4$ and evaporated. The residue was purified by column chromatography on silica gel eluting with PE/EA (4:1-1:1) to give title compound N-(((2,2-dimethoxyethyl)amino)(methyl)(oxo)-$\lambda^6$-sulfanylidene)-4-methylbenzenesulfonamide (6b). MS-ESI (m/z): 337 [M+1]$^+$.

N-(2,2-dimethoxyethyl)methanesulfonimidamide (6c)

The title compound N-(2,2-dimethoxyethyl)methanesulfonimidamide (6c) was prepared according to the synthetic method of 1b by replacing N-(dimethyl(oxo)-$\lambda^6$-sulfanylidene)-4-methylbenzenesulfonamide (1a) with N-(((2,2-dimethoxyethyl)amino)(methyl)(oxo)-$\lambda^6$-sulfanylidene)-4-methylbenzenesulfonamide (6b). MS-ESI (m/z): 183 [M+1]$^+$.

N-(2-((4-(4-(3-bromo-4-fluorophenyl)-5-oxo-4,5-dihydro-1,2,4-oxadiazol-3-yl)-1,2,5-oxadiazol-3-yl)amino)ethyl)methanesulfonimidamide (6d)

To a suspension of N-(2,2-dimethoxyethyl)methanesulfonimidamide (6c) (28 mg, 0.15 mmol) and 3-(4-amino-1,2,5-oxadiazol-3-yl)-4-(3-bromo-4-fluorophenyl)-1,2,4-oxadiazol-5(4H)-one (Intermediate A) (73 mg, 0.23 mmol) in DCM (1 mL) at room temperature was added $MeSO_3H$ (1 ml), followed by $Et_3SiH$ (1 ml), and the resulting solution was stirred at room temperature for 30 min. Then the mixture was poured into saturated $NaHCO_3$ aqueous solution (10 ml), extracted with DCM (3×10 mL), washed with brine (10 ml), dried over $Na_2SO_4$ and concentrated. The residue was purified by flash column chromatography on silica gel eluting with DCM/MeOH (20:1) to give the title compound N-(2-((4-(4-(3-bromo-4-fluorophenyl)-5-oxo-4,5-dihydro-1,2,4-oxadiazol-3-yl)-1,2,5-oxadiazol-3-yl)amino)ethyl)methanesulfonimidamide (6d). MS-ESI (m/z): 462 [M+1]$^+$.

(Z)—N-(3-bromo-4-fluorophenyl)-N'-hydroxy-4-((2-(methylsulfonoimidamido)eth yl)amino)-1,2,5-oxadiazole-3-carboximidamide (6)

To a solution of N-(2-((4-(4-(3-bromo-4-fluorophenyl)-5-oxo-4,5-dihydro-1,2,4-oxadiazol-3-yl)-1,2,5-oxadiazol-3-yl)amino)ethyl)methanesulfonimidamide (6d) (5 mg, 0.011 mmol) in THF (1 mL) at room temperature was added 5% NaOH aqueous solution (0.5 ml). The mixture was stirred at room temperature for 40 min. Then, the mixture was adjusted to pH=3 using 10% $H_3PO_4$ aqueous solution, and diluted with water (10 ml), extracted with DCM (3×10 mL), washed with brine (10 ml), dried over $Na_2SO_4$, and evaporated, and The residue was purified by column chromatography on silica gel eluting with DCM/MeOH (10:1) to give the title compound (Z)—N-(3-bromo-4-fluorophenyl)-N'-hydroxy-4-((2-(methylsulfonoimidamido)ethyl)-amino)-1,2,5-oxadiazole-3-carboximidamide (6). MS-ESI (m/z): 436 [M+1]$^+$.

Example 7

(Z)—N-(3-bromo-4-fluorophenyl)-4-((2-(ethylsulfonoimidamido)ethyl)amino)-N'-hydroxy-1,2,5-oxadiazole-3-carboximidamide (7)

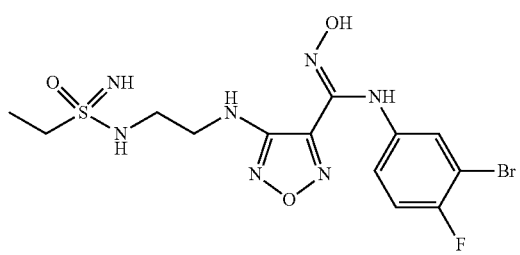

N-tosylethanesulfonimidoyl chloride (7a)

The title compound N-tosylethanesulfonimidoyl chloride (7a) was prepared according to the method described in WO 2014018355.

(Z)—N-(3-bromo-4-fluorophenyl)-4-((2-(ethylsulfonoimidamido)ethyl)amino)-N'-hydroxy-1,2,5-oxadiazole-3-carboximidamide (7)

The title compound (Z)—N-(3-bromo-4-fluorophenyl)-4-((2-(ethylsulfonoimidamido)ethyl)amino)-N'-hydroxy-1,2,5-oxadiazole-3-carboximidamide (7) was prepared according to the synthetic method of 6 by replacing N-tosylmethanesulfonimidoyl chloride (6a) with N-tosylethanesulfonimidoyl chloride (7a). MS-ESI (m/z): 450 [M+1]$^+$.

Example 8

(Z)—N-(3-bromo-4-fluorophenyl)-N'-hydroxy-4-((3-(methylsulfonoimidamido)propyl)amino)-1,2,5-oxadiazole-3-carboximidamide 18)

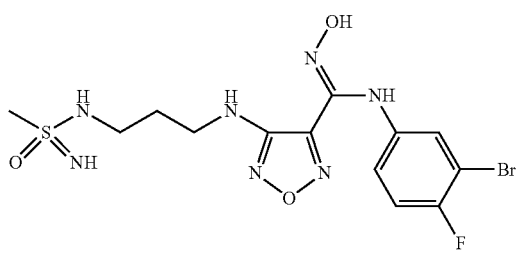

3,3-dimethoxypropan-1-amine (8a)

The title compound 3,3-dimethoxypropan-1-amine (8a) was prepared according to the method described in Advanced Synthesis and Catalysis, 2016, 358; 380.

(Z)—N-(3-bromo-4-fluorophenyl)-N'-hydroxy-4-((3-(methylsulfonoimidamido)propyl)amino)-1,2,5-oxadiazole-3-carboximidamide (8)

The title compound (Z)—N-(3-bromo-4-fluorophenyl)-N'-hydroxy-4-((3-(methyl-sulfonoimidamido)propyl)amino)-1,2,5-oxadiazole-3-carboximidamide (8) was prepared according to the synthetic method of 6 by replacing 2,2-dimethoxyethan-1-amine with 3,3-dimethoxypropan-1-amine (8a). MS-ESI (m/z): 450 [M+1]+.

Example 9

(Z)—N-(3-bromo-4-fluorophenyl)-N'-hydroxy-4-((2-(methylsulfonoimidamido)propyl)amino)-1,2,5-oxadiazole-3-carboximidamide (9)

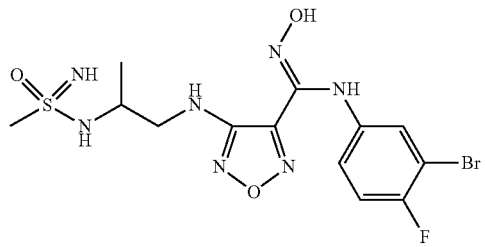

1,1-dimethoxypropan-2-amine (9a)

The title compound 1,1-dimethoxypropan-2-amine (9a) was prepared according to the method described in Advanced Synthesis and Catalysis, 2016, 358: 380.

(Z)—N-(3-bromo-4-fluorophenyl)-N'-hydroxy-4-((2-(methylsulfonoimidamido)propyl)amino)-1,2,5-oxadiazole-3-carboximidamide (9)

The title compound (Z)—N-(3-bromo-4-fluorophenyl)-N'-hydroxy-4-((2-(methyl-sulfonoimidamido)propyl)amino)-1,2,5-oxadiazole-3-carboximidamide (9) was prepared according to the synthetic method of 6 by replacing 2,2-dimethoxyethan-1-amine with 1,1-dimethoxypropan-2-amine (9a). MS-ESI (m/z): 450 [M+1]+.

Example 10

(Z)—N-(3-bromo-4-fluorophenyl)-N'-hydroxy-4-((1-(methylsulfonoimidamido)propan-2-yl)amino)-1,2,5-oxadiazole-3-carboximidamide (10)

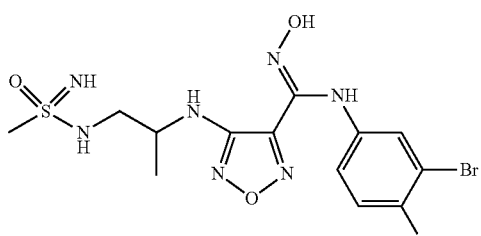

2,2-dimethoxypropan-1-amine (10a)

The title compound 2,2-dimethoxypropan-1-amine (10a) was prepared according to the method described in Advanced Synthesis and Catalysis, 2016, 358: 380.

(Z)—N-(3-bromo-4-fluorophenyl)-N'-hydroxy-4-((1-(methylsulfonoimidamido)propan-2-yl)amino)-1,2,5-oxadiazole-3-carboximidamide (10)

The title compound (Z)—N-(3-bromo-4-fluorophenyl)-N-hydroxy-4-((1-(methyl-sulfonoimidamido)propan-2-yl)amino)-1,2,5-oxadiazole-3-carboximidamide (10) was prepared according to the synthetic method of 6 by replacing 2,2-dimethoxyethan-1-amine with 2,2-dimethoxypropan-1-amine (10a). MS-ESI (m/z): 450 [M+1]+.

Example 11

(Z)—N-(3-bromo-4-fluorophenyl)-N'-hydroxy-4-((2-(N'-methylmethylsulfonoamidimidamido)ethyl)amino)-1,2,5-oxadiazole-3-carboximidamide (11)

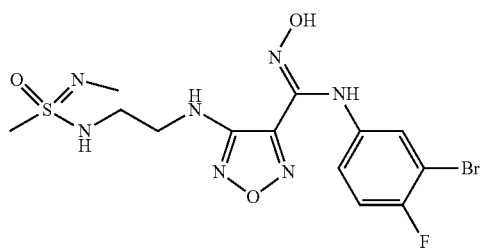

N-(2,4-dimethoxybenzyl)-2,2-dimethoxyethan-1-amine (11a)

To a solution of 2,2-dimethoxyethan-1-amine (1.0 g, 9.5 mmol) and 2,4-dimethoxybenzaldehyde (1.6 g, 9.6 mmol) in DCM (100 ml) at room temperature was added NaBH(OAc)$_3$ (6.0 g, 28.3 mmol). The resulting mixture was stirred at room temperature overnight. Then, the reaction was quenched with saturated NaHCO$_3$ aqueous solution (300 ml), and the mixture was extracted with DCM (3×100 ml), washed with brine (100 ml), dried over Na$_2$SO$_4$ and concentrated. The residue was purified by flash column chromatography on silica gel eluting with PE/EA (5:1) to give the title compound N-(2,4-dimethoxybenzyl)-2,2-dimethoxyethan-1-amine (11a). MS-ESI (m/z): 256 [M+1]+.

N-(2,4-dimethoxybenzyl)-N-(2,2-dimethoxyethyl)methanesulfonimidamide (11b)

The title compound N-(2,4-dimethoxybenzyl)-N-(2,2-dimethoxyethyl)methane-sulfonimidamide (11b) was prepared according to the synthetic method of 6c by replacing 2,2-dimethoxyethan-1-amine with N-(2,4-dimethoxybenzyl)-2,2-dimethoxyethan-1-amine (11a). MS-ESI (m/z): 333 [M+1]+.

N-(2,4-dimethoxybenzyl)-N-(2,2-dimethoxyethyl)-N'-methylmethanesulfonimidamide (11c)

To a solution of N-(2,4-dimethoxybenzyl)-N-(2,2-dimethoxyethyl)methane-sulfonimidamide (11b) (160 mg, 0.48 mmol) and iodomethane (75 g, 0.53 mmol) in DMF (2 ml)

at 0° C. was added NaH (30 mg, 0.75 mmol). The resulting mixture was stirred at room temperature for 30 min. Then, the reaction was quenched with saturated NH₄Cl aqueous solution (20 ml), and mixture was extracted with EA (3×10 ml), washed with brine (10 ml), dried over Na₂SO₄ and concentrated. The residue was purified by flash column chromatography on silica gel eluting with PE/EA (5:1-1:2) to give the title compound N-(2,4-dimethoxybenzyl)-N-(2,2-dimethoxyethyl)-N-methylmethanesulfonimidamide (11c). MS-ESI (m/z): 347 [M+1]⁺.

(Z)—N-(3-bromo-4-fluorophenyl)-N'-hydroxy-4-((2-(N'-methylmethylsulfonoamidimidamido)ethyl)amino)-1,2,5-oxadiazole-3-carboximidamide (11)

The title compound (Z)—N-(3-bromo-4-fluorophenyl)-N'-hydroxy-4-((2-(N-methylmethylsulfonoamidimidamido)ethyl)amino)-1,2,5-oxadiazole-3-carboximidamide (11) was prepared according to the synthetic method of 6 by replacing N-(2,2-dimethoxyethyl) methane-sulfonimidamide (6c) with N-(2,4-dimethoxybenzyl)-N-(2,2-dimethoxyethyl)-N-methylmethane-sulfonimidamide (11c). MS-ESI (m/z): 450 [M+1]⁺.

Example 12

(Z)—N-(3-chloro-4-fluorophenyl)-N'-hydroxy-4-((2-(methylsulfonoimidamido)-ethyl)amino)-1,2,5-oxadiazole-3-carboximidamide (12)

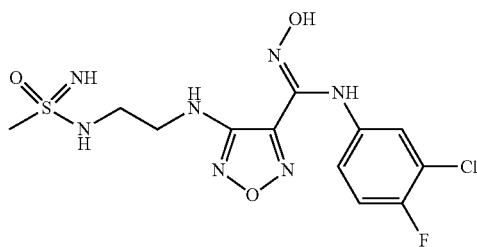

The title compound (Z)—N-(3-chloro-4-fluorophenyl)-N-hydroxy-4-((2-(methyl-sulfonoimidamido)ethyl)amino)-1,2,5-oxadiazole-3-carboximidamide (12) was prepared according to the synthetic method of 6 by replacing 3-(4-amino-1,2,5-oxadiazol-3-yl)-4-(3-bromo-4-fluorophenyl)-1,2,4-oxadiazol-5(4H)-one (Intermediate A) with 3-(4-amino-1,2,5-oxadiazol-3-yl)-4-(3-chloro-4-fluorophenyl)-1,2,4-oxadiazol-5 (4H)-one (Intermediate B). MS-ESI (m/z): 392 [M+1]⁺.

Example 13

(Z)—N-(3-cyano-4-fluorophenyl)-N'-hydroxy-4-((2-(methylsulfonoimidamido)-ethyl)amino)-1,2,5-oxadiazole-3-carboximidamide (13)

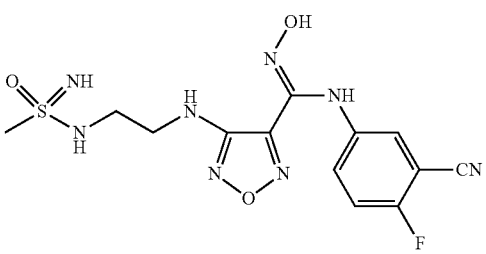

The title compound (Z)—N-(3-cyano-4-fluorophenyl)-N-hydroxy-4-((2-(methyl-sulfonoimidamido)ethyl)amino)-1,2,5-oxadiazole-3-carboximidamide (13) was prepared according to the synthetic method of 6 by replacing 3-(4-amino-1,2,5-oxadiazol-3-yl)-4-(3-bromo-4-fluorophenyl)-1,2,4-oxadiazole-5(4H)-one (Intermediate A) with 5-(3-(4-amino-1,2,5-oxadiazol-3-yl)-5-oxo-1,2,4-oxadiazol-4(5H)-yl)-2-fluorobenzonitrile (Intermediate C). MS-ESI (m/z): 383 [M+1]⁺.

Example 14

(Z)—N-(4-fluoro-3-(trifluoromethyl)phenyl)-N'-hydroxy-4-((2-(methylsulfonoamidimidamido)ethyl)amino)-1,2,5-oxadiazole-3-carboximidamide (14)

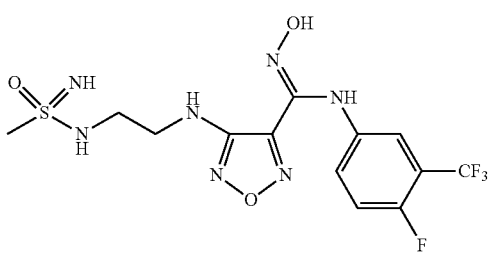

The title compound (Z)—N-(4-fluoro-3-(trifluoromethyl)phenyl)-N'-hydroxy-4-((2-(methylsulfonoamidimidamido)ethyl)amino)-1,2,5-oxadiazole-3-carboximidamide (14) was prepared according to the synthetic method of 6 by replacing 3-(4-amino-1,2,5-oxadiazol-3-yl)-4-(3-bromo-4-fluorophenyl)-1,2,4-oxadiazol-5(4H)-one (Intermediate A) with 3-(4-amino-1,2,5-oxadiazol-3-yl)-4-(4-fluoro-3-(trifluoromethyl)-phenyl)-1,2,4-oxadiazol-5(4H)-one (Intermediate D). MS-ESI (m/z): 426 [M+1]⁺.

Example 15

(Z)—N'-hydroxy-4-((2-(methylsulfonoamidimidamido)ethyl)amino)-N-(3-(trifluoromethyl)phenyl)-1,2,5-oxadiazole-3-carboximidamide (15)

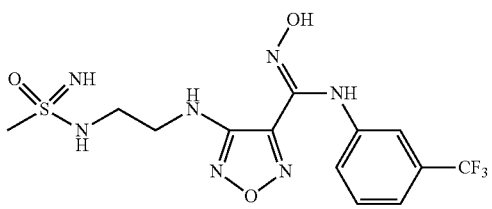

The title compound (Z)—N-hydroxy-4-((2-(methyl-sulfonoamidimidamido)ethyl)-amino)-N-(3-(trifluoromethyl)phenyl)-1,2,5-oxadiazole-3-carboximidamide (15) was prepared according to the synthetic method of 6 by replacing 3-(4-amino-1,2,5-oxadiazol-3-yl)-4-(3-bromo-4-fluorophenyl)-1,2,4-oxadiazol-5(4H)-one (Intermediate A) with 3-(4-amino-1,2,5-oxadiazol-3-yl)-4-(3-(trifluoromethyl)phenyl)-1,2,4-oxadiazol-5(4H)-one (Intermediate E). MS-ESI (m/z): 408 [M+1]⁺.

Example 16

(Z)-4-((2-(ethylsulfonoimidamido)ethyl)amino)-N'-hydroxy-N-(3-(trifluoromethyl)phenyl)-1,2,5-oxadiazole-3-carboximidamide (16)

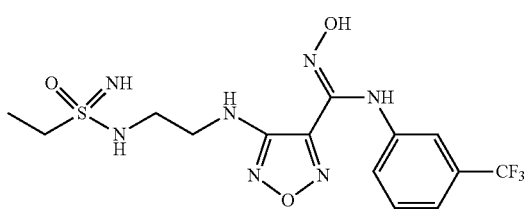

The title compound (Z)-4-((2-(ethyl sulfonoimidamido)ethyl)amino)-N'-hydroxy- N-(3-(trifluoromethyl)phenyl)-1,2,5-oxadiazole-3-carboximidamide (16) was prepared according to the synthetic method of 6 by replacing N-tosylmethanesulfonimidoyl chloride (6a) with N-tosylethanesulfonimidoyl chloride (7a) and replacing 3-(4-amino-1,2,5-oxadiazol-3-yl)- 4-(3-bromo-4-fluorophenyl)-1,2,4-oxadiazol-5(4H)-one (Intermediate A) with 3-(4-amino- 1,2,5-oxadiazol-3-yl)-4-(3-(trifluoromethyl)phenyl)-1,2,4-oxadiazol-5(4H)-one (Intermediate E). MS-ESI (m/z): 422 [M +1]+.

Example 17

(Z)—N-(3-bromo-4-fluorophenyl)-4-((3-(N,N'-dimethylsulfamidimidoyl)propyl)amino)-N'-hydroxy-1,2,5-oxadiazole-3-carboximidamide (17)

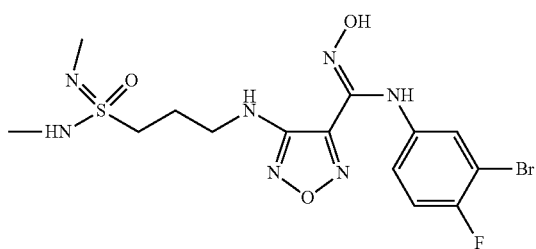

4-(3-bromo-4-fluorophenyl)-3-(4-((3-bromopropyl)amino)-1,2,5-oxadiazol-3-yl)-1,2,4-oxadiazol-5(4H)-one (17a)

To a solution of 3-(4-amino-1,2,5-oxadiazol-3-yl)-4-(3-bromo-4-fluorophenyl)-1,2,4-oxadiazol-5(4H)-one (Intermediate A) (1.5 g, 4.39 mmol) and 3-bromo-1,1-dimethoxypropane (2.8 g, 15.35 mmol) in DCM (30 mL) at 0° C. was added 2,2,2-trifluoroacetic acid (9.0 ml), followed by the addition of triethylsilane (4.2 ml, 26.32 mmol) dropwise at 0° C. for 10 min. The resulting solution was stirred at room temperature for 1 h. Then the mixture was poured into saturated NaHCO₃ aqueous solution (100 ml), extracted with DCM (3×50 mL), washed with brine (100 ml), dried over Na₂SO₄ and concentrated. The residue was purified by flash column chromatography on silica gel eluting with EA/PE (1:10) to give the title compound 4-(3-bromo-4-fluorophenyl)-3-(4-((3-bromopropyl)amino)-1,2,5-oxadiazol-3-yl)-1,2,4-oxadiazol-5(4H)-one (17a). MS-ESI (m/z): 462/464 [M+1]+.

S-(3-((4-(4-(3-bromo-4-fluorophenyl)-5-oxo-4,5-dihydro-1,2,4-oxadiazol-3-yl)-1,2,5-oxadiazol-3-yl)amino)propyl) ethanethioate (17b)

To a solution of 4-(3-bromo-4-fluorophenyl)-3-(4-((3-bromopropyl)amino)-1,2,5-oxadiazol-3-yl)-1,2,4-oxadiazol-5 (4H)-one (17a) (1.8 g, 3.89 mmol) in acetone (20 mL) was added potassium ethanethioate (0.66 g, 5.83 mmol) at room temperature. The resulting solution was stirred at room temperature for 2 h. Then the mixture was poured into water (50 ml), extracted with EA (3×30 mL), washed with water (2×30 mL) and brine (30 ml), dried over Na₂SO₄ and concentrated. The crude product S-(3-((4-(4-(3-bromo-4-fluorophenyl)-5-oxo-4,5-dihydro-1,2,4-oxadiazol-3-yl)-1,2,5-oxadiazol-3-yl)amino)propyl) ethanethioate (17b) was used directly for the next step. MS-ESI (m/z): 458/460 [M+1]+.

S-(3-((4-(4-(3-bromo-4-fluorophenyl)-5-oxo-4,5-dihydro-1,2,4-oxadiazol-3-yl)-1,2,5-oxadiazol-3-yl)(tert-butoxycarbonyl)amino)propyl) ethanethioate (17c)

To a solution of S-(3-((4-(4-(3-bromo-4-fluorophenyl)-5-oxo-4,5-dihydro-1,2,4-oxadiazol-3-yl)-1,2,5-oxadiazol-3-yl)amino)propyl) ethanethioate (17b) (1.8 g, 3.89 mmol) and di-tert-butyl dicarbonate (1.3 g, 5.84 mmol) in MeCN (30 mL) was added NEt₃ (0.79 g, 7.78 mmol) and DMAP (0.47 g, 3.89 mmol) at room temperature. The resulting solution was stirred at room temperature for 2 h. Then the mixture was poured into water (50 ml), extracted with EA (3×30 mL), washed with water (2×30 mL) and brine (30 ml), dried over Na₂SO₄ and concentrated. The residue was purified by flash column chromatography on silica gel eluting with EA/PE (1:10) to give the title compound S-(3-((4-(4-(3-bromo-4-fluorophenyl)-5-oxo-4,5-dihydro-1,2,4-oxadiazol-3-yl)-1,2,5-oxadiazol-3-yl)(tert-butoxycarbonyl)amino)propyl) ethanethioate (17c), MS-ESI (m/z): 558/560 [M+1]+.

tert-butyl (4-(4-(3-bromo-4-fluorophenyl)-5-oxo-4,5-dihydro-1,2,4-oxadiazol-3-yl)-1,2,5-oxadiazol-3-yl)(3-((methylamino)sulfinyl)propyl)carbamate (17d)

To a solution of S-(3-((4-(4-(3-bromo-4-fluorophenyl)-5-oxo-4,5-dihydro-1,2,4-oxadiazol-3-yl)-1,2,5-oxadiazol-3-yl)(tert-butoxycarbonyl)amino)propyl) ethanethioate (17c) (106.0 mg, 0.19 mmol) in DCM (2.0 mL) was added acetic anhydride (19.4 mg, 0.19 mmol) at −30° C., followed by the addition of sulfuryl chloride (51.0 mg, 0.38 mmol) at −30° C. The resulting solution was stirred to room temperature. The solvent was evaporated under vacuum and the residue was dissolved in THF (2 mL), methylamine (2 M in THF, 0.2 mL, 0.38 mmol) was added at 0° C. The resulting solution was stirred at room temperature for 2 h. The mixture was poured into water (10 ml), extracted with EA (3×10 mL), washed with water (2×10 mL) and brine (10 ml), dried over Na₂SO₄ and concentrated. The residue was purified by flash column chromatography on silica gel eluting with EA/PE (1:1) to give the title compound tert-butyl (4-(4-(3-bromo-4-fluorophenyl)-5-oxo-4,5-dihydro-1,2,4-oxadiazol- 3-yl)-1,2,5-oxadiazol-3-yl)(3-((methylamino)sulfinyl)pro-pyl)carbamate (17d). MS-ESI (m/z): 561/563 [M+1]⁺.

tert-butyl (4-(4-(3-bromo-4-fluorophenyl)-5-oxo-4, 5-dihydro-1,2,4-oxadiazol-3-yl)-1,2,5-oxadiazol-3-yl)(3-(N,N'-dimethylsulfamidimidoyl)propyl)carbamate (17e)

To a solution of tert-butyl (4-(4-(3-bromo-4-fluorophenyl)-5-oxo-4,5-dihydro-1,2,4-oxadiazol-3-yl)-1,2,5-oxadiazol-3-yl)(3-((methylamino)sulfinyl)propyl)carbamate (17d) (56.0 mg, 0.10 mmol) in THF (2.0 mL) was added 1-chloro-1H-benzo[<d][1,2,3]triazole (16.0 mg, 0.11 mmol) at room temperature. The resulting solution was stirred at room temperature for 30 min. Then methylamine (2M in THF, 0.06 mL, 0.12 mmol) was added at −78° C., the resulting solution was warmed up to room temperature naturally and stirred at room temperature for 3 h. The mixture was poured into water (10 ml), extracted with EA (3×10 mL), washed with water (2×10 mL) and brine (10 ml), dried over Na₂SO₄ and concentrated. The residue was purified by flash column chromatography on silica gel eluting with MeOH/DCM (1:20) to give the title compound tert-butyl (4-(4-(3-bromo-4-fluorophenyl)-5-oxo-4,5-dihydro-1, 2,4-oxadiazol-3-yl)-1,2,5-oxadiazol-3-yl)(3-(N,N'-dimethylsulfamidimidoyl)propyl)carbamate (17e). MS-ESI (m/z): 590/592 [M+1]⁺.

3-((4-(4-(3-bromo-4-fluorophenyl)-5-oxo-4,5-dihydro-1,2,4-oxadiazol-3-yl)-1,2,5-oxadiazol-3-yl)amino)-N,N'-dimethylpropane-1-sulfonimidamide (17f)

To a solution of tert-butyl (4-(4-(3-bromo-4-fluorophenyl)-5-oxo-4,5-dihydro-1,2,4-oxadiazol-3-yl)-1,2,5-oxadiazol-3-yl)(3-(N,N'-dimethylsulfamidimidoyl)propyl)carbamate (17e) (26.0 mg, 0.044 mmol) in DCM (2.0 mL) was added trifluoroacetic acid (1.0 mL) at 0° C. The resulting solution was stirred at room temperature for 1 h. The solvent was evaporated under vacuum and the residue was dissolved in EA (30 mL), washed with saturated NaHCO₃ aqueous solution, water (10 mL) and brine (10 ml), dried over Na₂SO₄ and concentrated. The crude product 3-((4-(4-(3-bromo-4-fluorophenyl)-5-oxo-4,5-dihydro-1,2,4-oxadiazol-3-yl)-1,2,5-oxadiazol-3-yl)amino)-N,N'-dimethylpropane-1-sulfonimidamide (17f) was used directly for the next step. MS-ESI (m/z): 490/492 [M+1]⁺.

(Z)—N-(3-bromo-4-fluorophenyl)-4-((3-(N,N'-dimethylsulfamidimidoyl)propyl)amino)-N'-hydroxy-1, 2,5-oxadiazole-3-carboximidamide (17)

To a solution of 3-((4-(4-(3-bromo-4-fluorophenyl)-5-oxo-4,5-dihydro-1,2,4-oxadiazol-3-yl)-1,2,5-oxadiazol-3-yl)amino)-N,N'-dimethylpropane-1-sulfonimidamide (17f) (16.0 mg, 0.033 mmol) in THF (2.0 mL) was added 5% NaOH aqueous solution (1.0 mL) at room temperature. The resulting solution was stirred at room temperature for 20 min. The mixture was poured into water (5 ml), extracted with EA (3×5 mL), washed with water (2×5 mL) and brine (5 ml), dried over Na₂SO₄ and concentrated. The residue was purified by flash column chromatography on silica gel eluting with MeOH/DCM (1:15) to give the title compound (Z)—N-(3-bromo-4-fluorophenyl)-4-((3-(N,N-dimethylsulfamidimidoyl)propyl)amino)-N'-hydroxy-1,2,5-oxadiazole-3-carboximidamide (17). MS-ESI (m/z): 464/466 [M+1]⁺.

Example 18

(Z)—N-(3-chloro-4-fluorophenyl)-4-((3-(N,N'-dimethylsulfamidimidoyl)propyl)amino)-N'-hydroxy-1, 2,5-oxadiazole-3-carboximidamide (18)

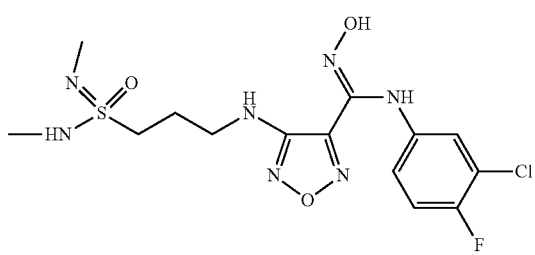

18

The title compound (Z)—N-(3-chloro-4-fluorophenyl)-4-((3-(N,N'-dimethyl-sulfamidimidoyl)propyl)amino)-N'-hydroxy-1,2,5-oxadiazole-3-carboximidamide (18) was prepared according to the synthetic method of example 17 by replacing 3-(4-amino-1,2,5-oxadiazol-3-yl)-4-(3-bromo-4-fluorophenyl)-1,2,4-oxadiazol-5 (4H)-one (Intermediate A) with 3-(4-amino-1,2,5-oxadiazol-3-yl)-4-(3-chloro-4-fluorophenyl)-1,2,4-oxadiazol-5(4H)-one (Intermediate B). MS-ESI (m/z): 420 [M+1]⁺.

Example 19

(Z)—N-(3-ethynyl-4-fluorophenyl)-N'-hydroxy-4-((2-(methylsulfonoamidimidamido)ethyl)amino)-1,2, 5-oxadiazole-3-carboximidamide (19)

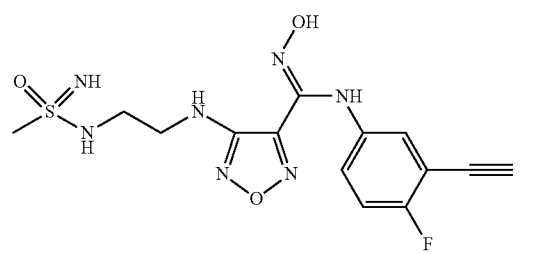

19

The title compound (Z)—N-(3-ethynyl-4-fluorophenyl)-N'-hydroxy-4-((2-(methyl-sulfonoamidimidamido)ethyl) amino)-1,2,5-oxadiazole-3-carboximidamide (19) was prepared according to the synthetic method of 6 by replacing 3-(4-amino-1,2,5-oxadiazol-3-yl)-4-(3-bromo-4-fluorophenyl)-1,2,4-oxadiazol-5(4H)-one (Intermediate A) with 3-(4-amino-1,2,5-oxadiazol-3-yl)-4-(3-ethynyl-4-fluorophenyl)-1,2,4-oxadiazol-5(4H)-one (Intermediate F). MS-ESI (m/z): 381 [M+1]⁺.

Example 20

(Z)—N-(3-bromo-4-fluorophenyl)-4-({2-[diimino(methyl)-N-sulfanyl]ethyl}amino)-N'-hydroxy-1,2,5-oxadiazole-3-carboximidamide (20)

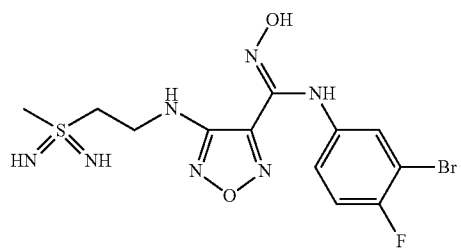

4-(3-bromo-4-fluorophenyl)-3-(4-((2-bromoethyl)amino)-1,2,5-oxadiazol-3-yl)-1,2,4-oxadiazol-5(4H)-one (20a)

The title compound 4-(3-bromo-4-fluorophenyl)-3-(4-((2-bromoethyl)amino)-1,2,5-oxadiazol-3-yl)-1,2,4-oxadiazol-5 (4H)-one (20a) was prepared according to the synthetic method of 17a by replacing 3-bromo-1,1-dimethoxypropane with 2-bromo-1,1-dimethoxyethane.

4-(3-bromo-4-fluorophenyl)-3-(4-((2-(methylthio)ethyl)amino)-1,2,5-oxadiazol-3-yl)-1,2,4-oxadiazol-5(4H)-one (20b)

To a solution of 4-(3-bromo-4-fluorophenyl)-3-(4-((2-bromoethyl)amino)-1,2,5-oxadiazol-3-yl)-1,2,4-oxadiazol-5(4H)-one (20a) (129 mg, 0.29 mmol) in DMF (2 mL) was added MeSNa (30 mg, 0.43 mmol) at 0-5° C. The resulting solution was stirred at room temperature for 2.5 h. Then the mixture was poured into saturated NH$_4$Cl aqueous solution (20 ml), extracted with EA (10 ml×3), dried over Na$_2$SO$_4$ and concentrated. The residue was purified by flash column chromatography on silica gel eluting with EA/PE (4:1) to give the title compound 4-(3-bromo-4-fluorophenyl)-3-(4-((2-(methylthio)ethyl)amino)-1,2,5-oxadiazol-3-yl)-1,2,4-oxadiazol-5(4H)-one (20b). MS-ESI (m/z): 414 [M-1]$^-$.

(Z)—N-(3-bromo-4-fluorophenyl)-4-({2-[diimino(methyl)-λ$^6$-sulfanyl]ethyl}amino)-N'-hydroxy-1,2,5-oxadiazole-3-carboximidamide (20)

To a solution of 4-(3-bromo-4-fluorophenyl)-3-(4-((2-(methylthio)ethyl)amino)-1,2,5-oxadiazol-3-yl)-1,2,4-oxadiazol-5(4H)-one (20b) (41 mg, 0.1 mmol) in MeCN (1.5 mL) was added 7 M ammonia methanol solution (1 mL) at −40~−20° C. followed by hypochlorous acid tert-butyl ester (107 mg, 0.98 mmol). The resulting mixture was stirred at room temperature overnight. The mixture was diluted with DCM (10 ml) and filtrated. The filtrate was concentrated and purified by prep-TLC eluting with DCM/MeOH (10:1) to give the title compound (Z)—N-(3-bromo-4-fluorophenyl)-4-({2-[diimino(methyl)-λ$^6$-sulfanyl]ethyl}amino)-N'-hydroxy-1,2,5-oxadiazole-3-carboximidamide (20). MS-ESI (m/z): 420 [M+1]$^+$.

Following essentially the same procedures described for Examples 1-20, or using similar synthetic strategies or methods, Examples 21-37 listed in Table 1 were prepared from appropriate starting materials which are commercially available or known in the literature. The structures and names of Examples 21-37 are given in Table 1.

TABLE 1

| EXAMPLE | STRUCTURE | NAME | DATA |
| --- | --- | --- | --- |
| 21 | 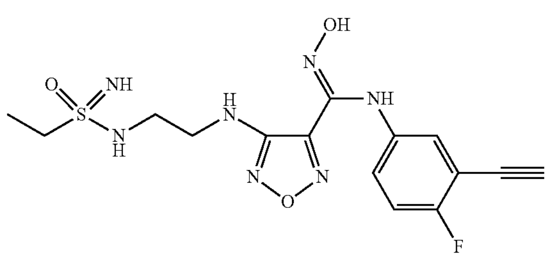 [SMILES: C#Cc1cc(N/C(=N\O)c2nonc2NCCNS(=N)(=O)CC)ccc1F] | (Z)-4-((2-(ethylsulfonoamidimidamido)ethyl)amino)-N-(3-ethynyl-4-fluorophenyl)-N'-hydroxy-1,2,5-oxadiazole-3-carboximidamide | MS-ESI (m/z): 396 [M + 1]$^+$ |
| 22 | 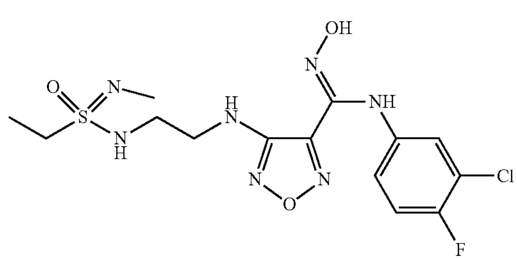 | (Z)-N-(3-chloro-4-fluorophenyl)-N'-hydroxy-4-((2-(N'-methylmethylsulfonoamidimidamido)ethyl)amino)-1,2,5-oxadiazole-3-carboximidamide | MS-ESI (m/z): 406 [M + 1]$^+$ |

TABLE 1-continued

| EXAMPLE | STRUCTURE | NAME | DATA |
|---|---|---|---|
| 23 | 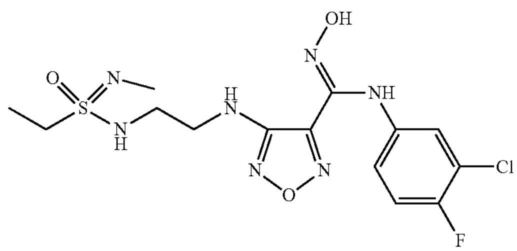 [SMILES: CCS(=O)(=NC)NCCNc1nonc1/C(=N/O)Nc1ccc(F)c(Cl)c1] | (Z)-N-(3-chloro-4-fluorophenyl)-N'-hydroxy-4-((2-(N'-methylethylsulfonoamidimidamido)ethyl)amino)-1,2,5-oxadiazole-3-carboximidamide | MS-ESI (m/z): 420 [M + 1]+ |
| 24 | 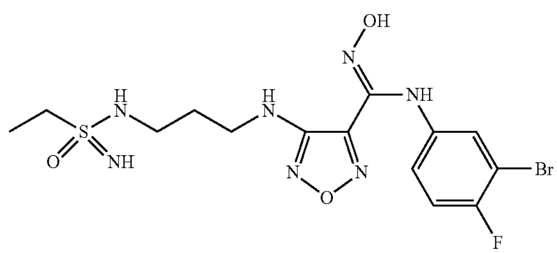 [SMILES: CCS(=N)(=O)NCCCNc1nonc1/C(=N/O)Nc1ccc(F)c(Br)c1] | (Z)-N-(3-bromo-4-fluorophenyl)-4-[(3-ethanesulfonoimidamidopropyl)amino]-N'-hydroxy-1,2,5-oxadiazole-3-carboximidamide | MS-ESI (m/z): 464 [M + 1]+ |
| 25 | 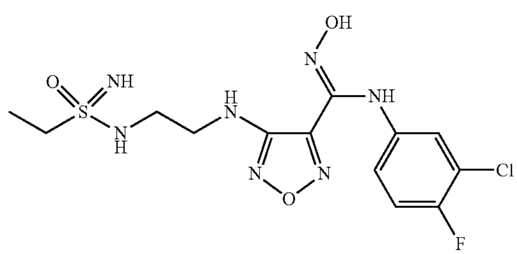 [SMILES: CCS(=N)(=O)NCCNc1nonc1/C(=N/O)Nc1ccc(F)c(Cl)c1] | (Z)-N-(3-chloro-4-fluorophenyl)-4-((2-(ethylsulfonoamidimidamido)ethyl)amino)-N'-hydroxy-1,2,5-oxadiazole-3-carboximidamide | MS-ESI (m/z): 406 [M + 1]+ |
| 26 | 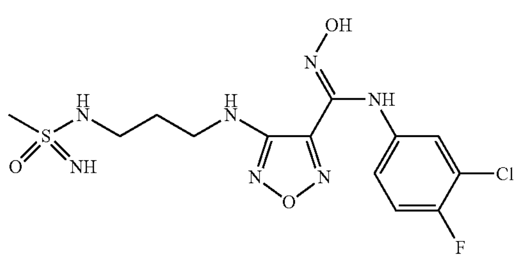 [SMILES: CS(=N)(=O)NCCCNc1nonc1/C(=N/O)Nc1ccc(F)c(Cl)c1] | (Z)-N-(3-chloro-4-fluorophenyl)-N'-hydroxy-4-[(3-methanesulfonoimidamidopropyl)amino]-1,2,5-oxadiazole-3-carboximidamide | MS-ESI (m/z): 406 [M + 1]+ |
| 27 | 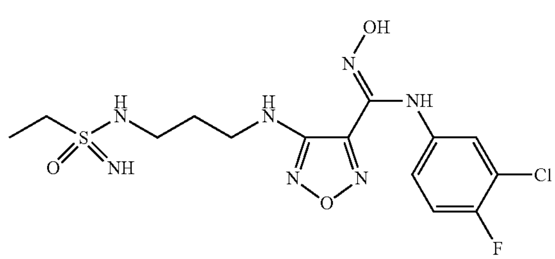 [SMILES: CCS(=N)(=O)NCCCNc1nonc1/C(=N/O)Nc1ccc(F)c(Cl)c1] | (Z)-N-(3-chloro-4-fluorophenyl)-4-[(3-ethanesulfonoimidamidopropyl)amino]-N'-hydroxy-1,2,5-oxadiazole-3-carboximidamide | MS-ESI (m/z): 420 [M + 1]+ |
| 28 | 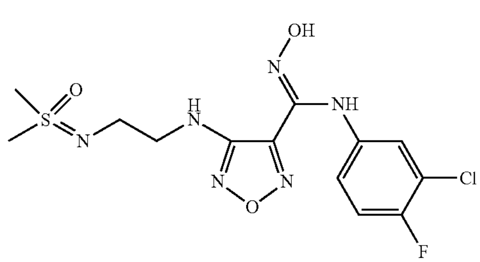 [SMILES: CS(C)(=O)=NCCNc1nonc1/C(=N/O)Nc1ccc(F)c(Cl)c1] | (Z)-N-(3-chloro-4-fluorophenyl)-4-((2-((dimethyl(oxo)-$\lambda^6$-sulfanylidene)amino)ethyl)amino)-N'-hydroxy-1,2,5-oxadiazole-3-carboximidamide | MS-ESI (m/z): 391 [M + 1]+ |

TABLE 1-continued

| EXAMPLE | STRUCTURE | NAME | DATA |
|---|---|---|---|
| 29 | 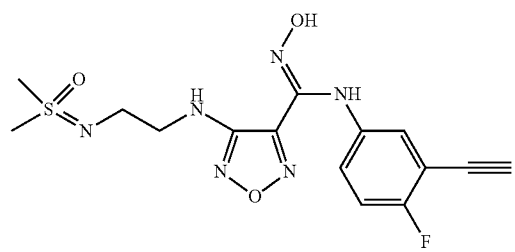 [SMILES: C#Cc1cc(N/C(=N\O)c2nonc2NCCN=S(C)(C)=O)ccc1F] | (Z)-4-((2-((dimethyl(oxo)-λ⁶-sulfanylidene)amino)ethyl)amino)-N-(3-ethynyl-4-fluorophenyl)-N'-hydroxy-1,2,5-oxadiazole-3-carboximidamide | MS-ESI (m/z): 381 [M + 1]⁺ |
| 30 | 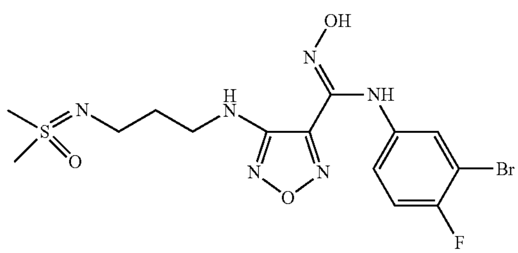 [SMILES: CS(C)(=O)=NCCCNc1nonc1/C(=N/O)Nc1ccc(F)c(Br)c1] | (Z)-N-(3-bromo-4-fluorophenyl)-4-((3-((dimethyl(oxo)-λ⁶-sulfanylidene)amino)propyl)amino)-N'-hydroxy-1,2,5-oxadiazole-3-carboximidamide | MS-ESI (m/z): 449 [M + 1]⁺ |
| 31 | 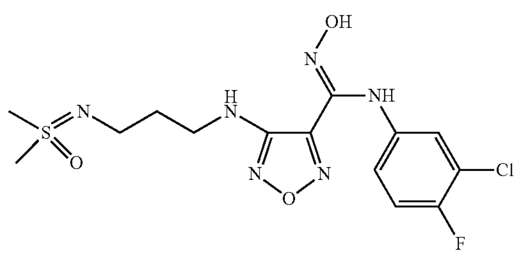 [SMILES: CS(C)(=O)=NCCCNc1nonc1/C(=N/O)Nc1ccc(F)c(Cl)c1] | (Z)-N-(3-chloro-4-fluorophenyl)-4-((3-((dimethyl(oxo)-λ⁶-sulfanylidene)amino)propyl)amino)-N'-hydroxy-1,2,5-oxadiazole-3-carboximidamide | MS-ESI (m/z): 405 [M + 1]⁺ |
| 32 | 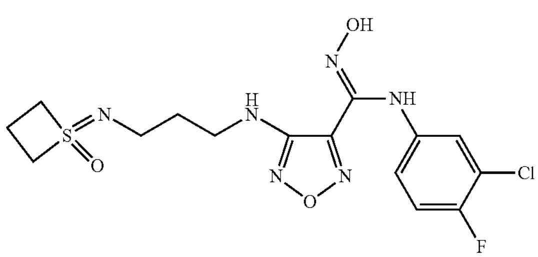 [SMILES: O=S1(=NCCCNc2nonc2/C(=N/O)Nc2ccc(F)c(Cl)c2)CCC1] | (Z)-N-(3-chloro-4-fluorophenyl)-N'-hydroxy-4-((3-((1-oxido-1λ⁶-thietan-1-ylidene)amino)propyl)amino)-1,2,5-oxadiazole-3-carboximidamide | MS-ESI (m/z): 417 [M + 1]⁺ |
| 33 | 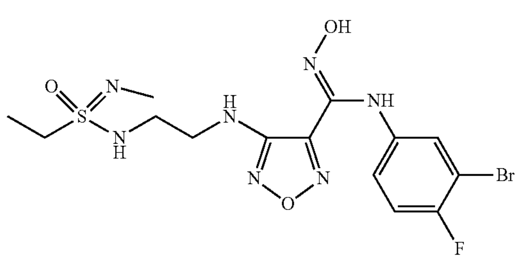 [SMILES: CCS(=O)(=NC)NCCNc1nonc1/C(=N/O)Nc1ccc(F)c(Br)c1] | (Z)-N-(3-bromo-4-fluorophenyl)-N'-hydroxy-4-((2-(N'-methylethylsulfonoamidimidamido)ethyl)amino)-1,2,5-oxadiazole-3-carboximidamide | MS-ESI (m/z): 464 [M + 1]⁺ |
| 34 | 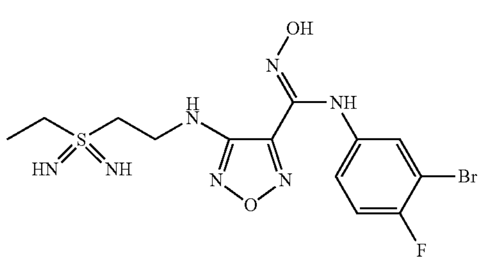 [SMILES: CCS(=N)(=N)CCNc1nonc1/C(=N/O)Nc1ccc(F)c(Br)c1] | (Z)-N-(3-bromo-4-fluorophenyl)-4-{[2-(ethyldiimino-λ⁶-sulfanyl)ethyl]amino}-N'-hydroxy-1,2,5-oxadiazole-3-carboximidamide | MS-ESI (m/z): 434 [M + 1]⁺ |

TABLE 1-continued

| EXAMPLE | STRUCTURE | NAME | DATA |
|---|---|---|---|
| 35 | 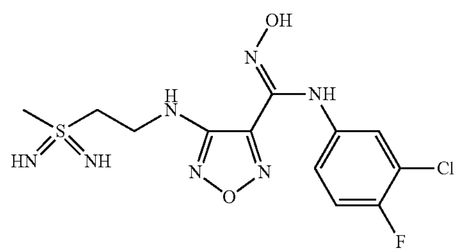 [SMILES: CS(=N)(=N)CCNc1nonc1/C(=N/O)Nc1ccc(F)c(Cl)c1] | (Z)-N-(3-chloro-4-fluorophenyl)-4-({2-[diimino(methyl)-$\lambda^6$-sulfanyl]ethyl}amino)-N'-hydroxy-1,2,5-oxadiazole-3-carboximidamide | MS-ESI (m/z): 376 [M + 1]$^+$ |
| 36 | 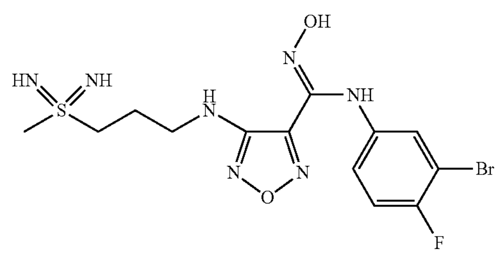 [SMILES: CS(=N)(=N)CCCNc1nonc1/C(=N/O)Nc1ccc(F)c(Br)c1] | (Z)-N-(3-bromo-4-fluorophenyl)-4-({3-[diimino(methyl)-$\lambda^6$-sulfanyl]propyl}amino)-N'-hydroxy-1,2,5-oxadiazole-3-carboximidamide | MS-ESI (m/z): 434 [M + 1]$^+$ |
| 37 | 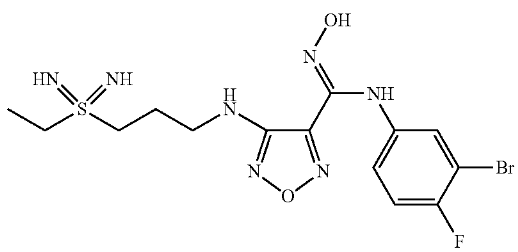 [SMILES: CCS(=N)(=N)CCCNc1nonc1/C(=N/O)Nc1ccc(F)c(Br)c1] | (Z)-N-(3-bromo-4-fluorophenyl)-4-{[3-(ethyldiimino-$\lambda^6$-sulfanyl)propyl]amino}-N'-hydroxy-1,2,5-oxadiazole-3-carboximidamide | MS-ESI (m/z): 448 [M + 1]$^+$ |
| 38 | 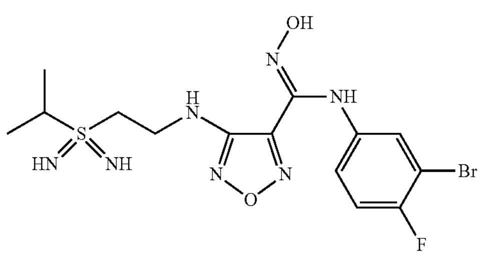 [SMILES: CC(C)S(=N)(=N)CCNc1nonc1/C(=N/O)Nc1ccc(F)c(Br)c1] | (Z)-N-(3-bromo-4-fluorophenyl)-4-({2-[diimino(propan-2-yl)-$\lambda^6$-sulfanyl]ethyl}amino)-N'-hydroxy-1,2,5-oxadiazole-3-carboximidamide | MS-ESI (m/z): 448 [M + 1]$^+$ |
| 39 | 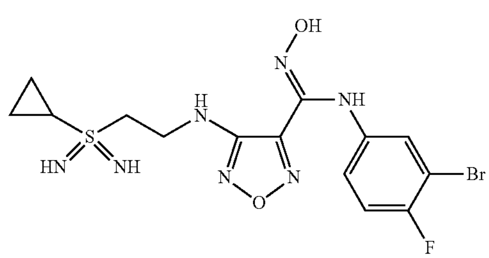 [SMILES: N=S(=N)(CCNc1nonc1/C(=N/O)Nc1ccc(F)c(Br)c1)C1CC1] | (Z)-N-(3-bromo-4-fluorophenyl)-4-{[2-(cyclopropyldiimino-$\lambda^6$-sulfanyl)ethyl]amino}-N'-hydroxy-1,2,5-oxadiazole-3-carboximidamide | MS-ESI (m/z): 446 [M + 1]$^+$ |
| 40 | 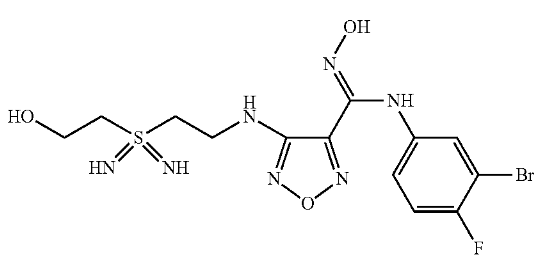 [SMILES: N=S(=N)(CCO)CCNc1nonc1/C(=N/O)Nc1ccc(F)c(Br)c1] | (Z)-N-(3-bromo-4-fluorophenyl)-N'-hydroxy-4-({2-[(2-hydroxyethyl)diimino-$\lambda^6$-sulfanyl]ethyl}amino)-1,2,5-oxadiazole-3-carboximidamide | MS-ESI (m/z): 450 [M + 1]$^+$ |

TABLE 1-continued

| EXAMPLE | STRUCTURE | NAME | DATA |
|---|---|---|---|
| 41 | 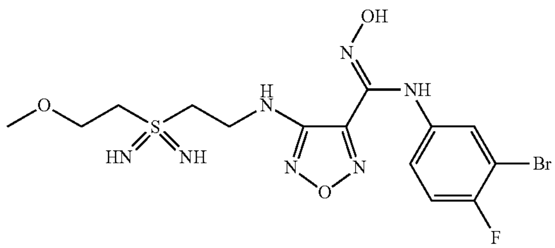 [SMILES: COCCS(=N)(=N)CCNc1nonc1/C(=N/O)Nc1ccc(F)c(Br)c1] | (Z)-N-(3-bromo-4-fluorophenyl)-4-({2-[diimino(2-methoxyethyl)-λ$^6$-sulfanyl]ethyl}amino)-N'-hydroxy-1,2,5-oxadiazole-3-carboximidamide | MS-ESI (m/z): 464 [M + 1]$^+$ |
| 42 | 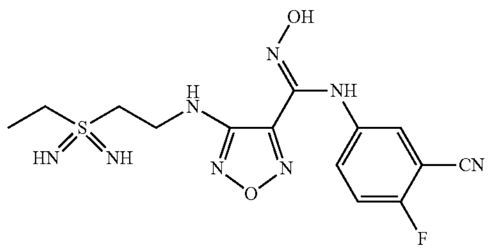 [SMILES: CCS(=N)(=N)CCNc1nonc1/C(=N/O)Nc1ccc(F)c(C#N)c1] | (Z)-N-(3-cyano-4-fluorophenyl)-4-{[2-(ethyldiimino-λ$^6$-sulfanyl)ethyl]amino}-N'-hydroxy-1,2,5-oxadiazole-3-carboximidamide | MS-ESI (m/z): 381 [M + 1]$^+$ |
| 43 | 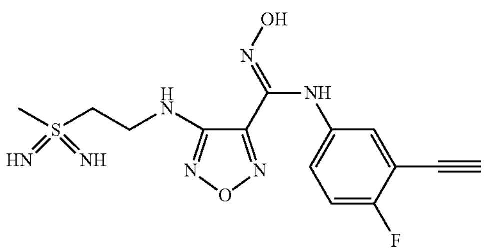 [SMILES: C#Cc1cc(N/C(=N\O)c2nonc2NCCS(C)(=N)=N)ccc1F] | (Z)-4-({2-[diimino(methyl)-λ$^6$-sulfanyl]ethyl}amino)-N-(3-ethynyl-4-fluorophenyl)-N'-hydroxy-1,2,5-oxadiazole-3-carboximidamide | MS-ESI (m/z): 366 [M + 1]$^+$ |
| 44 | 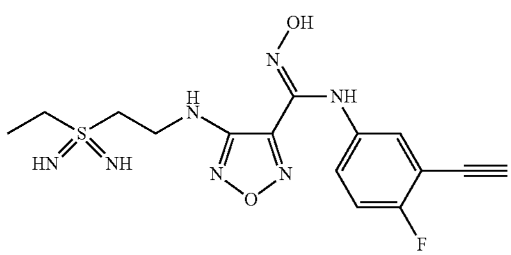 [SMILES: C#Cc1cc(N/C(=N\O)c2nonc2NCCS(=N)(=N)CC)ccc1F] | (Z)-4-{[2-(ethyldiimino-λ$^6$-sulfanyl)ethyl]amino}-N-(3-ethynyl-4-fluorophenyl)-N'-hydroxy-1,2,5-oxadiazole-3-carboximidamide | MS-ESI (m/z): 380 [M + 1]$^+$ |

Reference Compound I (Z)—N-(3-bromo-4-fluorophenyl)-N'-hydroxy-4-((2-(sulfamoylamino)ethyl)amino)-1,2,5-oxadiazole-3-carboximidamide (Reference compound 1I Reference compound 1 was disclosed and prepared following essentially the same procedures outlined in WO 2015070007.

Cell Proliferation Assays
IDO Cell-Based LC/MS Assay

Materials: RPMI 1640 (phenol red free) (Invitrogen Cat. No. 11835030), Fetal Bovine Serum (Invitrogen Cat. No. 10099141), Penicillin-Streptomycin (Invitrogen Gibco Cat. No. 15140-122), recombinant human interferon-gamma (R&D system, Cat. No. 285-IF-100), 5% (w/v) trichloroacetic acid (Alfa Aesar Cat. No. All 156), DMSO (Sigma, Cat. No. D2650), 96 wells_compound plate (Axygen, Cat. No. WIPP02280), 96 wells_assay plate (Greiner, Cat. No. 655090)

The concentrations of test compounds varied from 5 μM to 0.76 nM with 3-fold dilution, 9 points, in duplicates.

Hela cells were seeded at 40,000 cells per well with RPMI/phenol red free media containing 10% FBS in a 96-well tissue culture plate. After adding compound to cells, 100 ng/mL of recombinant human interferon-gamma was added to activate IDO signaling. The cells were incubated for 20 hours in 37° C. incubator with 5% CO$_2$. Compound treatment was stopped by adding 5% trichloroacetic acid. Subsequently, the cell plate was further incubated at 50° C. for 30 minutes. After precipitation, the supernatant was collected and measured by triple quadrupole mass spectrometer (AB Sciex 4000), coupled with HPLC Shimadzu EC 20 AD and autosampler CTC PAL. Curves are fit by XLFIT5 as % inhibition vs. log [compound concentration] using a 4 parameters logistic model 205.

Select compounds prepared as described above were assayed according to the biological procedures described herein. The results are given in the table 2.

TABLE 2

| Example | IC$_{50}$ (nM) |
| --- | --- |
| 1 | 54 |
| 2 | 270 |
| 3 | 153 |
| 4 | 477 |
| 5 | 195 |
| 6 | 63.7 |
| 7 | 6.6 |
| 8 | 18.6 |
| 9 | 123 |
| 10 | 244 |
| 11 | 40 |
| 12 | 12.3 |
| 13 | 311 |
| 14 | 20.1 |
| 15 | 54.3 |
| 16 | 298 |

IDO Cell-Based NEK Green Assay

Materials: RPMI 1640 (phenol red free) (Invitrogen Cat. No. 11835030), Fetal Bovine Serum (Invitrogen Cat. No. 10099141), Penicillin-Streptomycin (Invitrogen Gibco Cat. No. 15140-122), Cellular assay kit (NTRC, Cat. No. NTRC-GSCell-1K), DMSO (Sigma, Cat. No. D2650), 384 wells_compound plate (Greiner, Cat. No. 781280), 384 wells_assay plate (Greiner, Cat. No. 781091)

The concentrations of test compounds varied from 5 μM to 0.76 nM with 3-fold dilution, 10 points, in duplicates.

Hela cells were seeded at 8,000 cells per well with RPMI/phenol red free media containing 10% FBS in a 384-well tissue culture plate. Mixture of compounds and 1 mM L-Tryptophan were added to cells; and then the recombinant human interferon-gamma was added at the final concentration of 100 ng/mL to activate IDO signaling. The cells were incubated for 2 days in 37° C. incubator with 5% CO$_2$. After that, NFK Green was used to detect the N-formyl kynurenine level by following the commercial kit instruction. The fluorescent signal was measured by Envision plate Reader (excitation, 400/25; emission, 510/20). Curves are fit by XLFIT5 as % inhibition vs. log [compound concentration] using a 4 parameters logistic model 205.

Select compounds prepared as described above were assayed according to the biological procedures described herein. The results are given in the table 3.

TABLE 3

| Example | IC$_{50}$ (nM) |
| --- | --- |
| 17 | 10.6 |
| 18 | 23.2 |
| 19 | 13.3 |
| 20 | 12.2 |
| 21 | 16.3 |
| 22 | 27.5 |
| 23 | 33.2 |
| 24 | 8.2 |
| 25 | 17.5 |
| 26 | 14.0 |
| 27 | 16.5 |
| 28 | 14.5 |
| 29 | 26.5 |
| 30 | 63.6 |
| 31 | 112 |
| 32 | 64.4 |
| 33 | 23.9 |
| 34 | 9.7 |
| 35 | 33.7 |
| 36 | 46.7 |
| 37 | 20.5 |
| 38 | 13.3 |

TABLE 3-continued

| Example | IC$_{50}$ (nM) |
| --- | --- |
| 39 | 52.3 |
| 40 | 39.1 |
| 41 | 20.9 |
| 42 | 196 |
| 43 | 238 |
| 44 | 73.5 |

Rat PK

Each test compounds was suspended in 0.5% methylcellulose in water.

Grouping male SD rats was administered with test compound at a dose of 5 mg/kg by oral. After administering, blood samples were collected at time points of 0.50, 1.0, 2.0, 4.0, 6.0, 8.0 and 24.0 h. Standard curve was plotted based on concentrations of the samples in a suitable range, and the concentration of test compounds in plasma samples were determined by using LC-MS/MS. Pharmacokinetic parameters were calculated according to plasma concentration-time curve by Phoenix WinNonLin 6.1 software.

Results were given in table 4.

TABLE 4

| Example | Route | T$_{1/2}$ (h) | C$_{max}$ (ng/mL) | AUC$_{0-last}$ (ng · h/mL) | AUC$_{0-inf}$ (ng · h/mL) |
| --- | --- | --- | --- | --- | --- |
| 1 | p.o. | 3.83 | 1502 | 3840 | 4028 |
| 7 | p.o. | 3.47 | 496 | 1437 | 1452 |
| 28 | p.o. | 1.19 | 469 | 1102 | 1116 |
| Reference Compound 1 | p.o. | 2.48 | 169 | 880 | 924 |

The results demonstrated that compounds disclosed herein have much better C$_{max}$ and AUCs than Reference Compound 1.

What is claimed is:

1. A compound of formula (I)

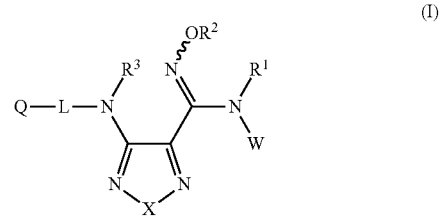

or a pharmaceutically acceptable salt thereof, wherein:
Q is selected from

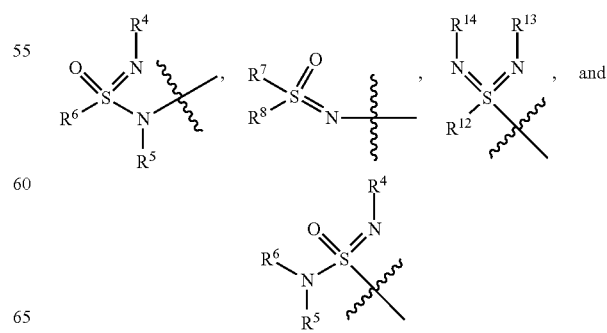

L is selected from —(CR$^{C1}$R$^{D1}$)$_t$— and —(CR$^{C1}$R$^{D1}$)$_t$O(CR$^{C1}$R$^{D1}$)$_u$—;

X is O;

W is selected from aryl and heteroaryl, wherein the aryl and heteroaryl are each unsubstituted or substituted with at least one substituent independently selected from R$^x$;

R$^1$ is hydrogen;

R$^2$ is hydrogen;

R$^3$ is hydrogen;

R$^4$, R$^5$, R$^{13}$ and R$^{14}$ are independently selected from hydrogen, C$_{1-10}$ alkyl, and C$_{3-10}$ cycloalkyl, wherein the alkyl and cycloalkyl are independently unsubstituted or substituted with at least one substituent independently selected from R$^x$;

R$^6$, R$^7$, R$^8$, and R$^{12}$ are independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein the alkyl, alkenyl, alkynyl, cycloalkyl, heterocyclyl, aryl and heteroaryl are each unsubstituted or substituted with at least one substituent independently selected from R$^x$;

or R$^7$ and R$^8$ together with the sulfur atom to which they are attached form a 4-12 membered ring containing, 0, 1 or 2 additional heteroatoms independently selected from oxygen, sulfur and nitrogen, and optionally substituted with 1, 2 or 3 R$^x$ groups;

each R$^{C1}$ and R$^{D1}$ are independently selected from hydrogen, halogen, C$_{1-10}$ alkyl, C$_{2-10}$ alkenyl, C$_{3-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein the alkyl, alkenyl, alkynyl, cycloalkyl, heterocyclyl, aryl and heteroaryl are each unsubstituted or substituted with at least one substituent independently selected from R$^x$;

or R$^{C1}$ and R$^{D1}$ together with the carbon atom(s) to which they are attached form a ring of 3 to 12 members containing 0, 1, or 2 heteroatoms independently selected from oxygen, sulfur and nitrogen, and optionally substituted with 1 2, or 3 R$^x$ groups;

each R$^x$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c1}$R$^{d1}$)$_t$NR$^{a1}$R$^{b1}$, —(CR$^{c1}$R$^{d1}$)$_t$OR$^{b1}$, —(CR$^{c1}$R$^{d1}$)$_t$S(O)$_r$R$^{b1}$, —(CR$^{c1}$R$^{d1}$)$_t$S(O)$_2$OR$^{b1}$, —(CR$^{c1}$R$^{d1}$)$_t$OS(O)$_2$R$^{b1}$, —(CR$^{c1}$R$^{d1}$)$_t$P(O)R$^{a1}$R$^{b1}$, —(CR$^{c1}$R$^{d1}$)$_t$P(O)(OR$^{a1}$)(OR$^{b1}$), —(CR$^{c1}$R$^{d1}$)$_t$C(O)R$^{a1}$, —(CR$^{c1}$R$^{d1}$)$_t$C(O)OR$^{b1}$, —(CR$^{c1}$R$^{d1}$)$_t$OC(O)R$^{b1}$, —(CR$^{c1}$R$^{d1}$)$_t$C(O)NR$^{a1}$R$^{b1}$, —(CR$^{c1}$R$^{d1}$)$_t$NR$^{a1}$C(O)R$^{b1}$, —(CR$^{c1}$R$^{d1}$)$_t$OC(O)NR$^{a1}$R$^{b1}$, —(CR$^{c1}$R$^{d1}$)$_t$NR$^{a1}$C(O)OR$^{b1}$, —(CR$^{c1}$R$^{d1}$)$_t$NR$^{a1}$C(O)NR$^{a1}$R$^{b1}$, —(CR$^{c1}$R$^{d1}$)$_t$NR$^{a1}$C(S)NR$^{a1}$R$^{b1}$, —(CR$^{c1}$R$^{d1}$)$_t$S(O)$_r$NR$^{a1}$R$^{b1}$, —(CR$^{c1}$R$^{d1}$)$_t$NR$^{a1}$S(O)$_r$R$^{b1}$, —(CR$^{c1}$R$^{d1}$)$_t$NR$^{a1}$S(O)$_2$NR$^{a1}$R$^{b1}$, —(CR$^{c1}$R$^{d1}$)$_t$S(O)(=NR$^{e1}$)R$^{b1}$, —(CR$^{c1}$R$^{d1}$)$_t$N=S(O)R$^{a1}$R$^{b1}$, —(CR$^{c1}$R$^{d1}$)$_t$NR$^{a1}$S(O)(=NR$^{e1}$)R$^{b1}$, —(CR$^{c1}$R$^{d1}$)$_t$S(O)(=NR$^{e1}$)NR$^{a1}$R$^{b1}$, —(CR$^{c1}$R$^{d1}$)$_t$NR$^{a1}$S(O)(=NR$^{e1}$)NR$^{a1}$R$^{b1}$, —(CR$^{c1}$R$^{d1}$)$_t$C(=NR$^{e1}$)R$^{a1}$, —(CR$^{c1}$R$^{d1}$)$_t$C(=N—OR$^{b1}$)R$^{a1}$, —(CR$^{c1}$R$^{d1}$)$_t$C(=NR$^{e1}$)NR$^{a1}$R$^{b1}$, —(CR$^{c1}$R$^{d1}$)$_t$NR$^{a1}$C(=NR$^{e1}$)R$^{b1}$ and —(CR$^{c1}$R$^{d1}$)$_t$NR$^{a1}$C(=NR$^{e1}$)NR$^{a1}$R$^{b1}$, wherein the alkyl, alkenyl, alkynyl, cycloalkyl, heterocyclyl, aryl and heteroaryl are each unsubstituted or substituted with at least one substituent independently selected from R$^Y$;

each R$^{a1}$ and each R$^{b1}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl -C$_{1-4}$ alkyl, aryl, aryl-C$_{1-4}$ alkyl, heteroaryl and heteroaryl-C$_{1-4}$ alkyl, wherein the alkyl, alkenyl, alkynyl, cycloalkyl, heterocyclyl, aryl and heteroaryl are each unsubstituted or substituted with at least one substituent independently selected from R$^Y$;

or Ra$^{a1}$ and R$^{b1}$ together with the atom(s) to which they are attached form a heterocyclic ring of 4 to 12 members containing 0, 1 or 2 additional heteroatoms independently selected from oxygen, sulfur and nitrogen, and optionally substituted with 1, 2 or 3 R$^Y$ groups;

each R$^{c1}$ and each R$^{d1}$ are independently selected from hydrogen, halogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, and heteroaryl-C$_{1-4}$ alkyl, wherein the alkyl, alkenyl, alkynyl, cycloalkyl, heterocyclyl, aryl and heteroaryl are each unsubstituted or substituted with at least one substituent independently selected from R$^Y$;

or R$^{c1}$ and R$^{d1}$ together with the carbon atom(s) to which they are attached form a ring of 3 to 12 members containing 0, 1 or 2 heteroatoms independently selected from oxygen, sulfur and nitrogen, and optionally substituted with 1, 2 or 3 R$^Y$ groups;

each R$^{e1}$ is independently selected from hydrogen, C$_{1-10}$ alkyl, C$_{3-10}$ cycloalkyl, C$_{3-10}$ cycloalkyl-C$_{1-4}$ alkyl, CN, NO$_2$, OR$^{a2}$, SR$^{a2}$, —S(O)$_r$R$^{a2}$, —S(O)$_r$NR$^{a2}$R$^{b2}$, —C(O)R$^{a2}$, —C(O)OR$^{a2}$ and —C(O)NR$^{a2}$R$^{b2}$;

each R$^Y$ is independently selected from C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, heterocyclyl, heterocyclyl-C$_{1-4}$ alkyl, aryl, aryl-C$_{1-4}$ alkyl, heteroaryl, heteroaryl-C$_{1-4}$ alkyl, halogen, —CN, —NO$_2$, —(CR$^{c2}$R$^{d2}$)$_t$NR$^{a2}$R$^{b2}$, —(CR$^{c2}$R$^{d2}$)$_t$OR$^{b2}$, —(CR$^{c2}$R$^{d2}$)$_t$S(O)$_r$R$^{b2}$, —(CR$^{c2}$R$^{d2}$)$_t$S(O)$_2$OR$^{b2}$, —(CR$^{c2}$R$^{d2}$)$_t$OS(O)$_2$R$^{b2}$, —(CR$^{c2}$R$^{d2}$)$_t$P(O)R$^{a2}$R$^{b2}$, —(CR$^{c2}$R$^{d2}$)$_t$P(O)(OR$^{a2}$)(OR$^{b2}$), —(CR$^{c2}$R$^{d2}$)$_t$C(O)R$^{a2}$, —(CR$^{c2}$R$^{d2}$)$_t$C(O)OR$^{b2}$, —(CR$^{c2}$R$^{d2}$)$_t$OC(O)R$^{b2}$, —(CR$^{c2}$R$^{d2}$)$_t$C(O)NR$^{a2}$R$^{b2}$, —(CR$^{c2}$R$^{d2}$)$_t$NR$^{a2}$C(O)R$^{b2}$, —(CR$^{c2}$R$^{d2}$)$_t$OC(O)NR$^{a2}$R$^{b2}$, —(CR$^{c2}$R$^{d2}$)$_t$NR$^{a2}$C(O)OR$^{b2}$, —(CR$^{c2}$R$^{d2}$)$_t$NR$^{a2}$R$^{b2}$, —(CR$^{c2}$R$^{d2}$)$_t$NR$^{a2}$C(S)NR$^{a2}$R$^{b2}$, —(CR$^{c2}$R$^{d2}$)$_t$S(O)$_r$NR$^{a2}$R$^{b2}$, —(CR$^{c2}$R$^{d2}$)$_t$NR$^{a2}$S(O)$_r$R$^{b2}$, —(CR$^{c2}$R$^{d2}$)$_t$NR$^{a2}$S(O)$_2$NR$^{a2}$R$^{b2}$, —(CR$^{c2}$R$^{d2}$)$_t$S(O)(=NR$^{e2}$)R$^{b2}$, —(CR$^{c2}$R$^{d2}$)$_t$N=S(O)R$^{a2}$R$^{b2}$, —(CR$^{c2}$R$^{d2}$)$_t$NR$^{a2}$S(O)(=NR$^{e2}$)R$^{b2}$, —(CR$^{c2}$R$^{d2}$)$_t$S(O)(=NR$^{e2}$)NR$^{a2}$R$^{b2}$, —(CR$^{c2}$R$^{d2}$)$_t$NR$^{a2}$S(O)(=NR$^{e2}$)NR$^{a2}$R$^{b2}$, —(CR$^{c2}$R$^{d2}$)$_t$C(=NR$^{e2}$)R$^{a2}$, —(CR$^{c2}$R$^{d2}$)$_t$C(=N—OR$^{b2}$)R$^{a2}$, —(CR$^{c2}$R$^{d2}$)$_t$C(=NR$^{e2}$)NR$^{a2}$R$^{b2}$, —(CR$^{c2}$R$^{d2}$)$_t$NR$^{a2}$C(=NR$^{e2}$)R$^{b2}$ and —(CR$^{c2}$R$^{d2}$)$_t$NR$^{a2}$C(=NR$^{e2}$)NR$^{a2}$R$^{b2}$, wherein the alkyl, alkenyl, alkynyl, cycloalkyl, heterocyclyl, aryl and heteroaryl are each unsubstituted or substituted with at least one substituent independently selected from OH, CN, amino, halogen, C$_{1-10}$ alkyl, C$_{2-10}$ alkenyl, C$_{2-10}$ alkynyl, C$_{3-10}$ cycloalkyl, C$_{1-10}$ alkoxy, C$_{3-10}$ cycloalkoxy, C$_{1-10}$ alkylthio, C$_{3-10}$ cycloalkylthio, C$_{1-10}$ alkylamino, C$_{3-10}$ cycloalkylamino and di(C$_{1-10}$ alkyl)amino;

each Ra$^{a2}$ and each R$^{b2}$ are independently selected from hydrogen, C$_{1-10}$ alkyl, C$_{2-10}$ alkenyl, C$_{2-10}$ alkynyl, C$_{3-10}$ cycloalkyl, C$_{3-10}$ cycloalkyl-C$_{1-4}$ alkyl, C$_{1-10}$ alkoxy, C$_{3-10}$ cycloalkoxy, C$_{1-10}$ alkylthio, C$_{3-10}$ cycloalkylthio, C$_{1-10}$ alkylamino, C$_{3-10}$ cycloalkylamino, di(C$_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein the alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{a1}$ and $R^{b2}$ together with the atom(s) to which they are attached form a heterocyclic ring of 4 to 12 members containing 0, 1, or 2 additional heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{c2}$ and each $R^{d2}$ are independently selected from hydrogen, halogen, $C_{1-10}$ alkyl, $C_{2-10}$ alkenyl, $C_{2-10}$ alkynyl, $C_{3-10}$ cycloalkyl, $C_{3-10}$ cycloalkyl-$C_{1-4}$ alkyl, $C_{1-10}$ alkoxy, $C_{3-10}$ cycloalkoxy, $C_{1-10}$ alkylthio, $C_{3-10}$ cycloalkylthio, $C_{1-10}$ alkylamino, $C_{3-1}$ cycloalkylamino, di($C_{1-10}$ alkyl)amino, heterocyclyl, heterocyclyl-$C_{1-4}$ alkyl, aryl, aryl-$C_{1-4}$ alkyl, heteroaryl, and heteroaryl-$C_{1-4}$ alkyl, wherein the alkyl, alkenyl, alkynyl, cycloalkyl, alkoxy, cycloalkoxy, alkylthio, cycloalkylthio, alkylamino, cycloalkylamino, heterocyclyl, aryl and heteroaryl are each unsubstituted or substituted with at least one substituent independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

or $R^{c2}$ and $R^{d2}$ together with the carbon atom(s) to which they are attached form a ring of 3 to 12 members containing 0, 1, or 2 heteroatoms independently selected from oxygen, sulfur and nitrogen, and optionally substituted with 1 or 2 substituents, independently selected from halogen, CN, $C_{1-10}$ alkyl, $C_{2-10}$ alkenyl, $C_{2-10}$ alkynyl, $C_{3-10}$ cycloalkyl, OH, $C_{1-10}$ alkoxy, $C_{3-10}$ cycloalkoxy, $C_{1-10}$ alkylthio, $C_{3-10}$ cycloalkylthio, amino, $C_{1-10}$ alkylamino, $C_{3-10}$ cycloalkylamino and di($C_{1-10}$ alkyl)amino;

each $R^{e2}$ is independently selected from hydrogen, CN, $NO_2$, $C_{1-10}$ alkyl, $C_{3-10}$ cycloalkyl, $C_{3-10}$ cycloalkyl-$C_{1-4}$ alkyl, $C_{1-10}$ alkoxy, $C_{3-10}$ cycloalkoxy, —C(O)$C_{1-4}$ alkyl, —C(O)$C_{3-10}$ cycloalkyl, —C(O)O$C_{1-4}$ alkyl, —C(O)O$C_{3-10}$ cycloalkyl, —C(O)$NH_2$, —C(O)NH($C_{1-4}$ alkyl), —C(O)N($C_{1-4}$ alkyl)$_2$, —C(O)NH($C_{3-10}$ cycloalkyl), —C(O)N($C_{3-10}$ cycloalkyl)$_2$, —S(O)$_2 C_{1-4}$ alkyl, —S(O)$_2 C_{3-10}$ cycloalkyl, —S(O)$_2 NH_2$, —S(O)$_2$NH($C_{1-4}$ alkyl), —S(O)$_2$N($C_{1-4}$ alkyl)$_2$, S(O)$_2$NH($C_{3-10}$ cycloalkyl) and —S(O)$_2$N($C_{3-10}$ cycloalkyl)$_2$;

each r is independently selected from 0, 1 and 2;
each t is independently selected from 0, 1, 2, 3 and 4; and
each u is independently selected from 0, 1, 2, 3 and 4.

2. The compound of claim 1 or a pharmaceutically acceptable salt thereof, wherein L is selected from —(CH$_2$)$_2$—, —CHCH$_3$CH$_2$—, —CH$_2$CHCH$_3$—, —(CH$_2$)$_3$— and —(CR$^{C1}$R$^{D1}$)$_t$O(CR$^{C1}$R$^{D1}$)$_u$—.

3. The compound of claim 1 or a pharmaceutically acceptable salt thereof, wherein W is aryl, wherein the aryl is unsubstituted or substituted with at least one substituent independently selected from $R^x$.

4. The compound of claim 3 or a pharmaceutically acceptable salt thereof, wherein W is phenyl, wherein the phenyl is unsubstituted or substituted with at least one substituent independently selected from halogen, ethynyl, CN and —CF$_3$.

5. The compound of claim 1 or a pharmaceutically acceptable salt thereof, wherein W is heteroaryl, wherein the heteroaryl is unsubstituted or substituted with at least one substituent independently selected from $R^x$.

6. The compound of claim 1 or a pharmaceutically acceptable salt thereof, wherein $R^4$ is selected from hydrogen and methyl.

7. The compound of claim 1 or a pharmaceutically acceptable salt thereof, wherein $R^5$ is hydrogen.

8. The compound of claim 1 or a pharmaceutically acceptable salt thereof, wherein $R^{13}$ and $R^{14}$ are hydrogen.

9. The compound of claim 1 or a pharmaceutically acceptable salt thereof, wherein $R^6$, $R^7$, $R^8$ and $R^{12}$ are independently selected from $C_{1-10}$ alkyl, wherein the alkyl is independently unsubstituted or substituted with at least one substituent independently selected from $R^x$.

10. The compound of claim 9 or a pharmaceutically acceptable salt thereof, wherein $R^6$, $R^7$ and $R^8$ are independently selected from methyl and ethyl.

11. The compound of claim 1 or a pharmaceutically acceptable salt thereof, wherein $R^{12}$ is selected from $C_{1-10}$ alkyl and $C_{3-10}$ cycloalkyl, wherein the alkyl and cycloalkyl are independently unsubstituted or substituted with at least one substituent independently selected from $R^x$.

12. The compound of claim 1 or a pharmaceutically acceptable salt thereof, wherein $R^7$ and $R^8$ together with the sulfur atom to which they are attached form a 4-6 membered ring containing 0, 1 or 2 additional heteroatoms independently selected from oxygen, sulfur and nitrogen, and optionally substituted with 1, 2 or 3 $R^x$ groups.

13. The compound of claim 1 or a pharmaceutically acceptable salt thereof, wherein each instance of at least one substituent is independently 1, 2, 3 or 4 substituents.

14. The compound of claim 11 or a pharmaceutically acceptable salt thereof, wherein $R^{12}$ is selected from methyl, ethyl, isopropyl, cyclopropyl, hydroxyethyl and methoxyethyl.

15. The compound of claim 1, selected from

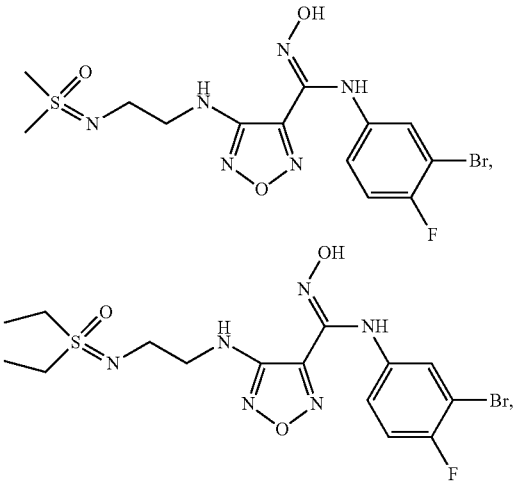

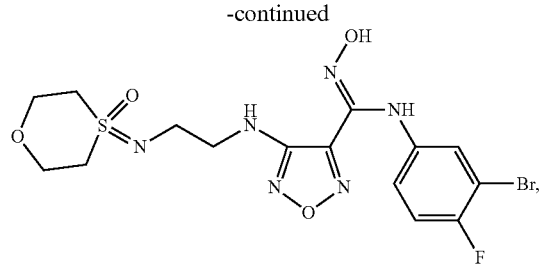
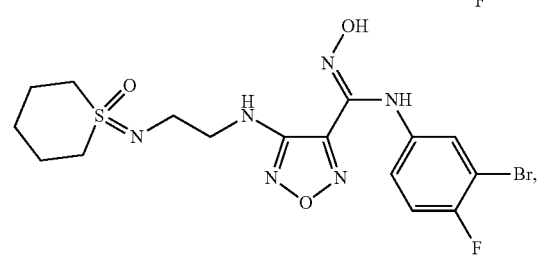
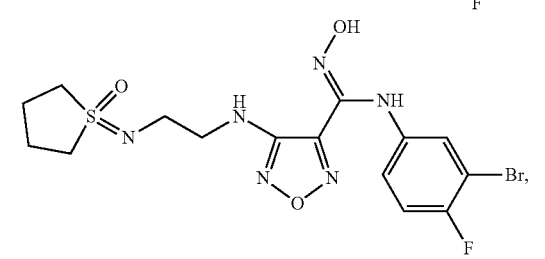
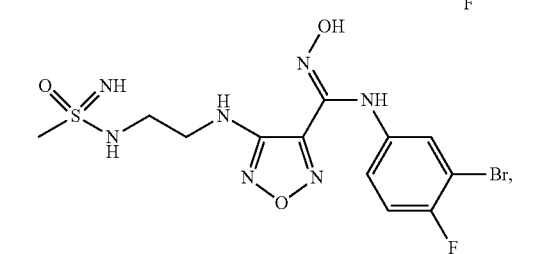
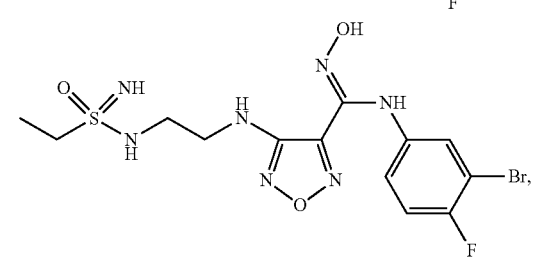
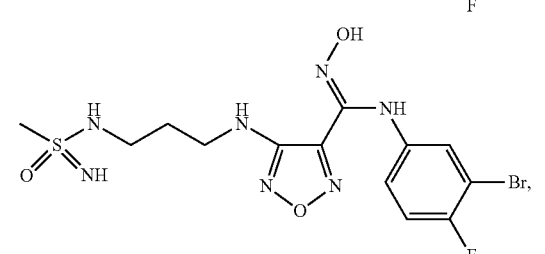
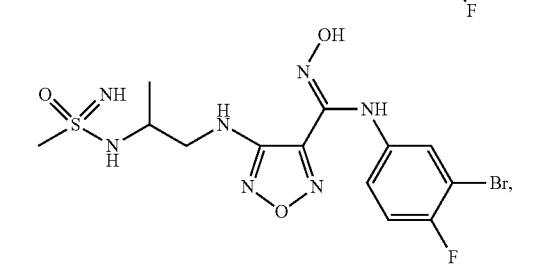
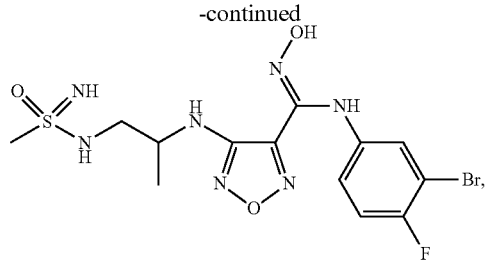
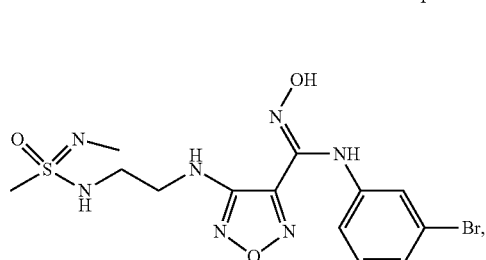
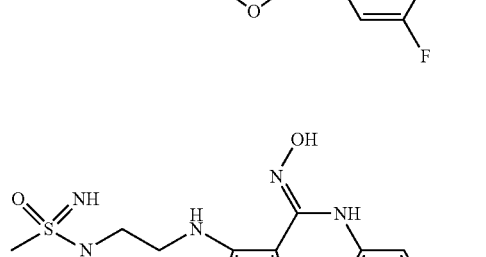
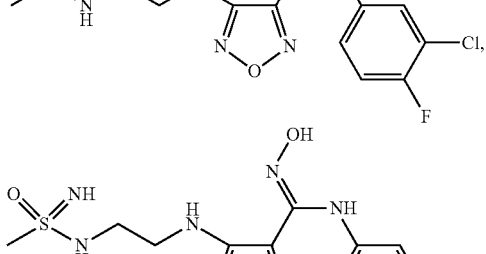
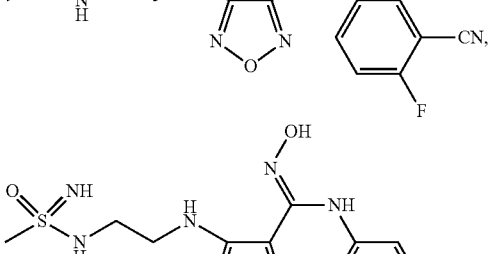
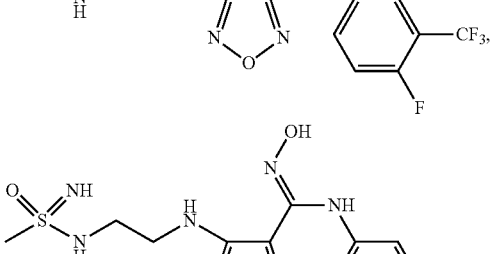
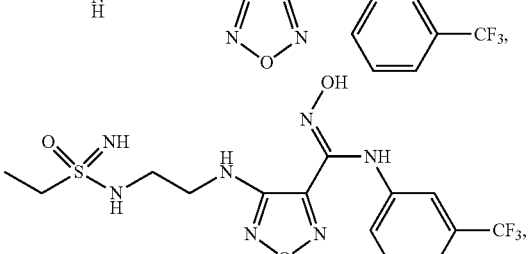

85
-continued
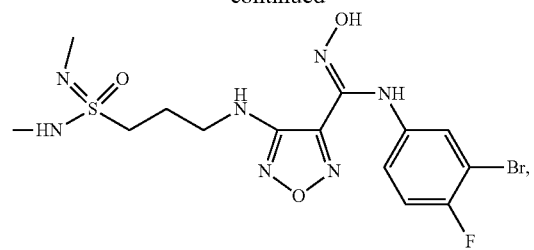
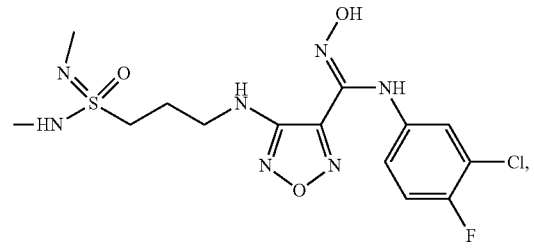
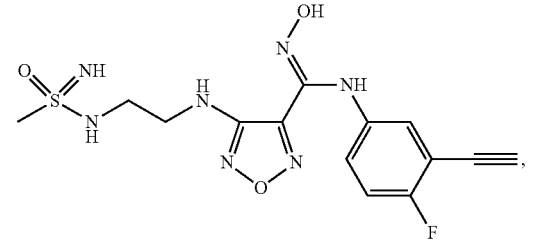
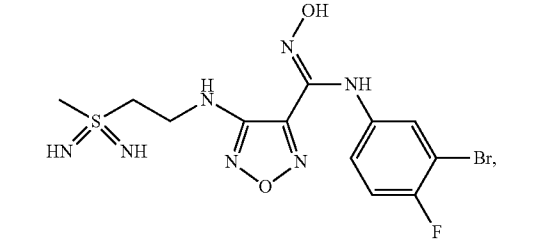
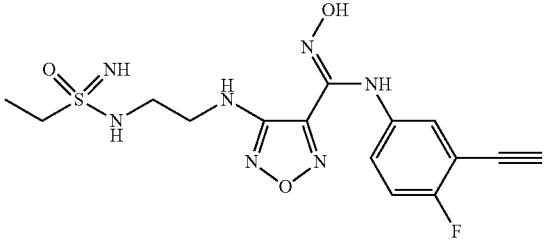
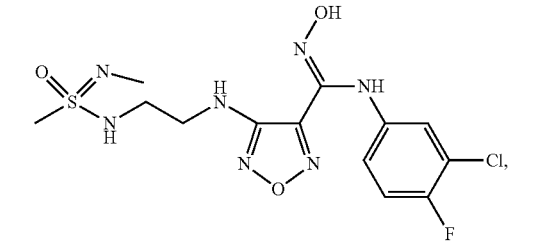
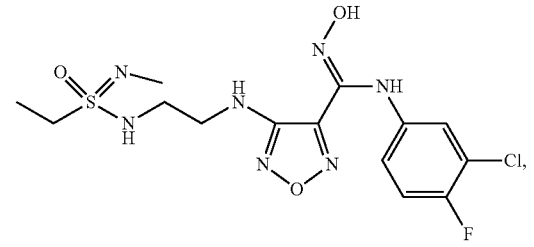
86
-continued
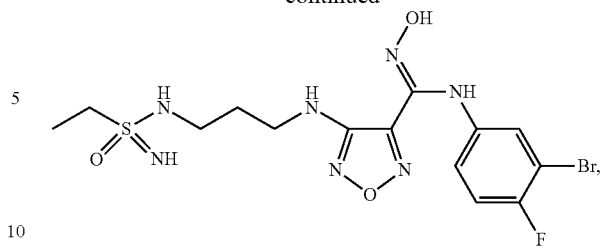
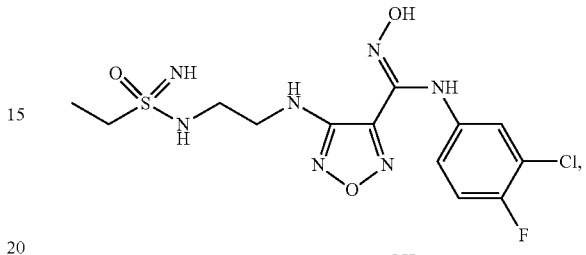
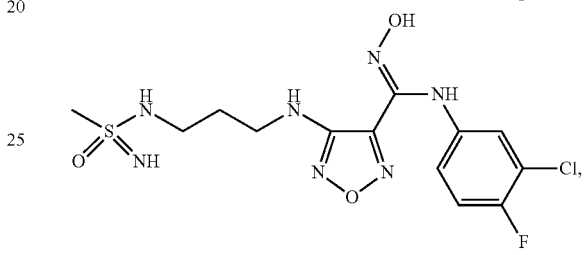
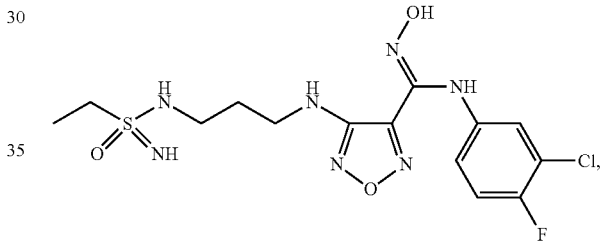
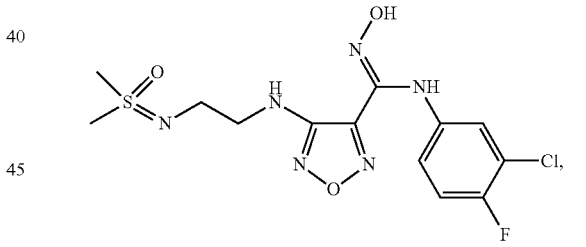
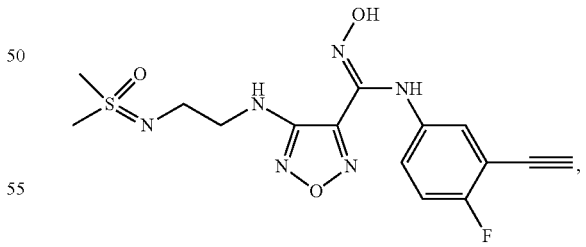
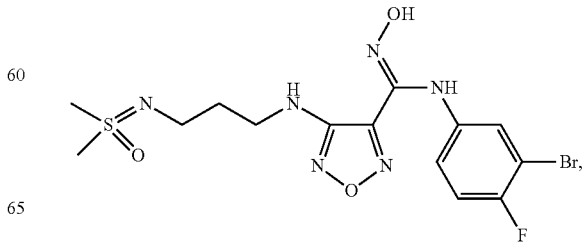

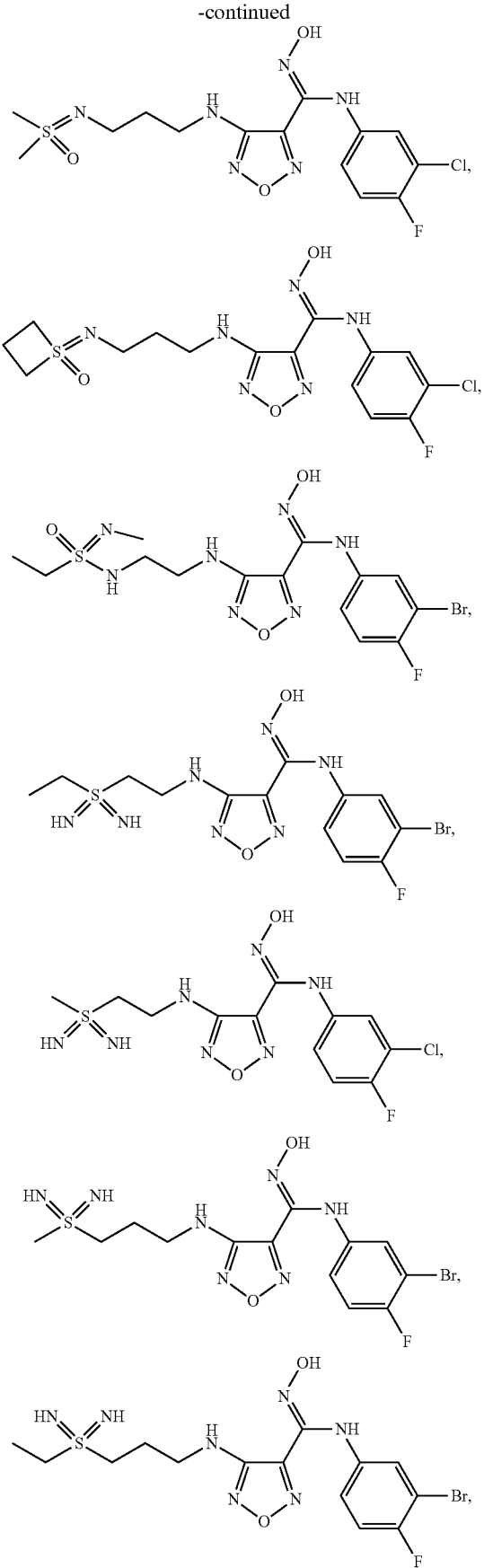
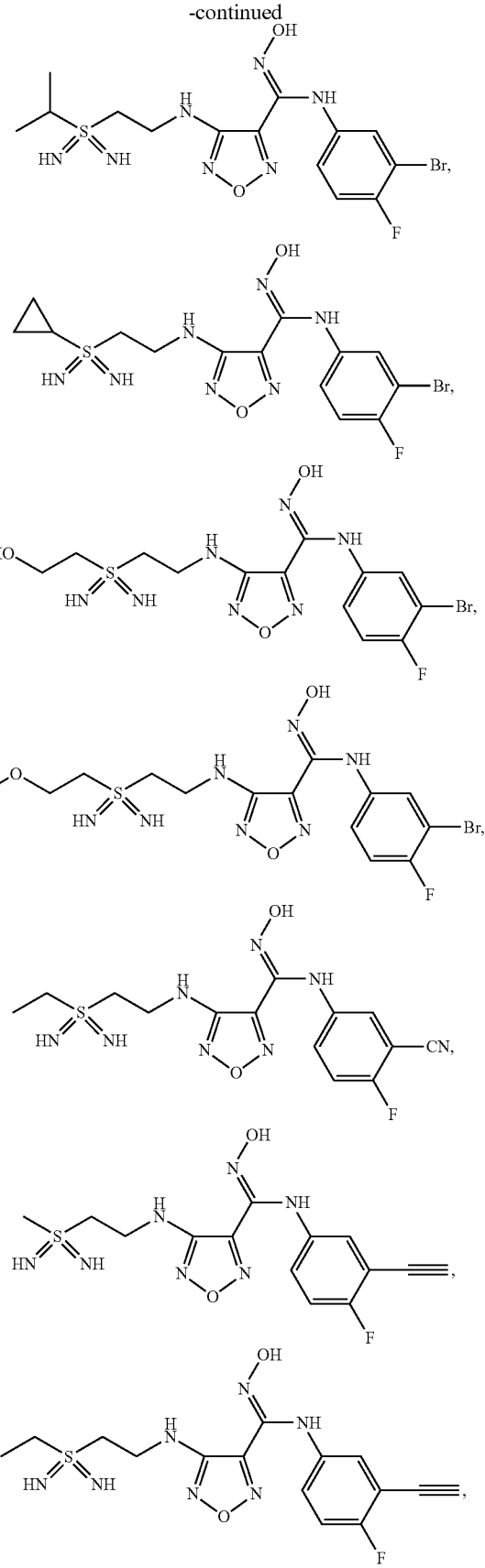
and pharmaceutically acceptable salts thereof.

16. A pharmaceutical composition, comprising the compound of claim 1, or a pharmaceutically acceptable salt thereof, and at least one pharmaceutically acceptable carrier.

17. A method of treating a cell-proliferative disorder, comprising administering to a subject in need of such treatment an effective amount of athe compound of claim 1 or a pharmaceutically acceptable salt thereof.

* * * * *